(12) United States Patent
Chen et al.

(10) Patent No.: US 12,161,733 B2
(45) Date of Patent: *Dec. 10, 2024

(54) CHEMICAL CONJUGATES OF EVANS BLUE DERIVATIVES AND THEIR USE AS RADIOTHERAPY AND IMAGING AGENTS FOR TARGETING PROSTATE CANCER

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Xiaoyuan Chen, Potomac, MD (US); Orit Jacobson Weiss, Silver Spring, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

(*) Notice: Subject to any disclaimer, the term of this patent is extended or adjusted under 35 U.S.C. 154(b) by 1065 days.

This patent is subject to a terminal disclaimer.

(21) Appl. No.: 16/969,673

(22) PCT Filed: Feb. 22, 2019

(86) PCT No.: PCT/US2019/019140
§ 371 (c)(1),
(2) Date: Aug. 13, 2020

(87) PCT Pub. No.: WO2019/165200
PCT Pub. Date: Aug. 29, 2019

(65) Prior Publication Data
US 2021/0008232 A1    Jan. 14, 2021

Related U.S. Application Data

(60) Provisional application No. 62/633,648, filed on Feb. 22, 2018.

(51) Int. Cl.
| | | |
|---|---|---|
| A61K 51/04 | (2006.01) |
| A61K 31/40 | (2006.01) |
| A61K 31/4025 | (2006.01) |
| A61K 45/06 | (2006.01) |
| A61K 47/54 | (2017.01) |
| A61K 49/00 | (2006.01) |

(52) U.S. Cl.
CPC ...... *A61K 51/0497* (2013.01); *A61K 31/4025* (2013.01); *A61K 45/06* (2013.01); *A61K 47/547* (2017.08); *A61K 49/0052* (2013.01)

(58) Field of Classification Search
CPC ........ A61K 51/00; A61K 51/04; A61K 51/08; A61K 49/00; A61P 35/04
See application file for complete search history.

(56) References Cited

U.S. PATENT DOCUMENTS

| | | | |
|---|---|---|---|
| 7,368,099 B2 | 5/2008 | Katayama et al. | |
| 10,981,866 B2 * | 4/2021 | Chen | A61P 35/04 |

(Continued)

FOREIGN PATENT DOCUMENTS

| | | |
|---|---|---|
| CN | 103242255 A | 8/2013 |
| CN | 104650217 A | 5/2015 |
| CN | 107629016 A | 1/2018 |

(Continued)

OTHER PUBLICATIONS

Cindy J. Choy et al., "Lu-Labeled Phosphoramidate-Based PSMA Inhibitors: The Effect of an Albumin Binder on Biodistribution and Therapeutic Efficacy in Prostate Tumor-Bearing Mice", Theranostics, vol. 7, Issue 7, 2017, 12 pages.

(Continued)

*Primary Examiner* — Michael G. Hartley
*Assistant Examiner* — Jagadishwar R Samala
(74) *Attorney, Agent, or Firm* — CANTOR COLBURN LLP

(57) ABSTRACT

A compound of Formula I or a pharmaceutically acceptable ester, amide, solvate, or salt thereof, or a salt of such an ester or amide or a solvate of such an ester amide or salt:

Formula I (Continued)

wherein the definitions of $R_1$-$R_{13}$ and $L_1$-$L_4$ are provided in the disclosure, and wherein $R_{14}$ is a group capable of binding to prostate-specific membrane antigen (PSMA).

20 Claims, 32 Drawing Sheets

(56) References Cited

U.S. PATENT DOCUMENTS

| | | | |
|---|---|---|---|
| 2016/0045626 | A1 | 2/2016 | McBride et al. |
| 2016/0052894 | A1 | 2/2016 | Chong |
| 2016/0287730 | A1 | 10/2016 | Chen et al. |
| 2019/0084931 | A1 | 3/2019 | Chen et al. |
| 2019/0201537 | A1 | 7/2019 | Chen et al. |
| 2020/0231543 | A1 | 7/2020 | Chen et al. |

FOREIGN PATENT DOCUMENTS

| | | | | |
|---|---|---|---|---|
| JP | 2010539163 | A | 12/2010 | |
| JP | 2011513241 | A | 4/2011 | |
| JP | 2014051442 | A | 3/2014 | |
| WO | 2004075925 | A1 | 9/2004 | |
| WO | 2006025304 | A1 | 3/2006 | |
| WO | 2010045598 | A2 | 4/2010 | |
| WO | WO-2016209795 | A1 * | 12/2016 | ............. A61K 38/12 |
| WO | 2017192874 | A1 | 11/2017 | |
| WO | WO-2017196806 | A1 * | 11/2017 | ......... A61K 51/0497 |
| WO | 2019070236 | A1 | 4/2019 | |
| WO | 2020160222 | A2 | 8/2020 | |

OTHER PUBLICATIONS

Extended European Search Report issued in Application No. 17928082.1 on Mar. 10, 2021, 6 pages.

Wang, et al, "Single Low-Dose Injection of Evans Blue Modified PSMA-617 Radioligand Therapy Eliminates Prostate-Specific Membrane Antigen Positive Tumors" Bioconjugate Chemistry, 2018, 29, (3213-3221).

Wang, et al., "Radioligand Therapy of Prostate Cancer with a Long-Lasting Prostate-Specific Membrance Antigen Targeting Agent 90Y-DOTA-EB-MCG" Bioconjugate Chem. 2018, 29, (2309-2315).

Extended European Search Report issued in EP Application No. 17796666.0 on Oct. 10, 2019, 5 pages.

Gang Niu et al., "In Vivo Labeling of Serum Albumin for PET" The Journal of Nuclear Medicine (2014), vol. 55, No. 7, p. 1150-1156.

Haojun Chen et al., "Chemical Conjugation of Evans Blue Derivative: A Strategy to Develop Long-Acting Therapeutics through Albumin Binding", Theranostics, vol. 6, Issue 2, Jan. 1, 2016, 11 pages.

Haojun Chen et al., "Novel molecular "add-on" based on Evans Blue confers superior pharmacokinetics and transforms drugs to theranostic agents", Journal of Nuclear Medicine, vol. 58, No. 4, Nov. 22, 2016, 10 pages.

International Search Report issued in Application No. PCT/US2019/019140 on Jun. 10, 2019, 6 pages.

Jinlong Wang et al., "Synthesis and mutagenic properties of direct dyes from 4,4'-diamino-p-terphenyl and 4,4'-diamino-p-quaterphenyl" Coloration Technology, Society of Dyers and Colourists, vol. 123, No. 1, Feb. 1, 2007, 7 pages.

Kaspar, A., Reicher, J., "Future directions for peptide therapeutics development" Drug Discovery Today (2013) vol. 18, No. 17, p. 807-817.

Rui Tian et al., "An Albumin Sandwich Enhances in Vivo Circulation and Stability of Metabolically Labile Peptides" Bioconjugate Chemistry, vol. 30, No. 6, May 13, 2019, 13 pages.

Satheesh Chandran M. et al., "Preparation and Characterization of Chain-Extended Bismaleimide/Carbon Fibre Composites" Hindawi Publishing Corporation, International Journal of Polymer Science, vol. 2010, 2010, 9 pages.

Wang, Y. et al., "In vivo albumin labeling and lymphatic imaging" PNAS (2015) vol. 112, No. 1, p. 208-213.

Written Opinion of the International Searching Authority issued in Application No. PCT/US2019/019140 on Jun. 10, 2019, 8 pages.

Yi Liu et al., "Stable Evans Blue Derived Exendin-4 Peptide for Type 2 Diabetes Treatment", Bioconjugate Chemistry, vol. 27, No. 1, Jan. 20, 2016, 12 pages.

Zhibo Liu et al., "Simple bioconjugate chemistry serves great clinical advances: albumin as a versatile platform for diagnosis and precision therapy", Chemical Society Reviews, vol. 45, No. 5, Mar. 7, 2016, 48 pages.

Benesova, M. et al.; "Preclinical Evaluation of a Tailor-Made DOTA-Conjugated PSMA Inhibitor with Optimized Linker Moiety for Imaging and Endroadtiotherapy of Prostate Cancer", J Nucl Med 2015; 56; 914-920.

* cited by examiner $IC_{50}$ (EB-PSMA-617) = 7.2 nM $IC_{50}$ (PSMA-617) = 68.5 nM Saline ⁹⁰Y-EB-PSMA-617
3.7 MBq ¹⁷⁷Lu-EB-PSMA-617
7.4 MBq $IC_{50}$ (EB-MCG) = 18.5 nM $IC_{50}$ (DOTA-MCG) = 104.7 nM

* Tumor recurrence

CHEMICAL CONJUGATES OF EVANS BLUE DERIVATIVES AND THEIR USE AS RADIOTHERAPY AND IMAGING AGENTS FOR TARGETING PROSTATE CANCER

CROSS REFERENCE TO RELATED APPLICATIONS

This Application is a U.S. National Stage Application of PCT/US2019/019140 filed Feb. 22, 2019 which claims priority to U.S. Provisional Application No. 62/633,648 filed Feb. 22, 2018 both of which re incorporated herein by reference in their entireties.

FIELD OF THE INVENTION

The present invention relates to functionalized derivatives of Evans Blue dye, and more particularly, to functionalized derivatives of Evans Blue dye that are useful as radiotherapy and imaging agents for targeting prostate cancer.

BRIEF DESCRIPTION OF THE ART

Prostate cancer is the most frequent malignant tumor in men worldwide. Prostate-specific membrane antigen (PSMA) is a surface molecule shown to be specifically expressed by prostate tumor cells. PSMA expression levels correlate with disease stage and by hormone-refractory cancers. Although most PSMA expression appears to be restricted to the prostate cancer, low levels of expression can also be detected in the brain, kidneys, salivary glands, and small intestine. The antigen was also shown to be expressed by neovascular tumor vessels of multiple other cancers.

Because expression of PSMA is substantially increased in advanced stages of prostate cancer and metastatic castration-resistant prostate cancer (mCRPC), the antigen has become a popular target for imaging and therapeutical treatment. The unique attributes of PSMA have led to multiple strategies targeting the antigen as a therapy for the disease, including vaccines, specific antibodies, drug-conjugated-antibodies, and radiotherapy.

In human patients, anti-PSMA antibody labeled with $^{177}$Lu, was shown to be an effective agent, but it had some bone marrow and hematology toxicity issues, possibly due to its long half-life in the blood (days). An $^{111}$In radiolabeled anti-PSMA antibody capromab pendetide (ProstaScint; EUSA Pharma), which targets the intracellular epitoe (7E11 of PSM), was approved by the U.S. Food and Drug Administration. However, the large molecular structure of the antibody together with the limited availability of the intracellular domain of PSMA resulted in very low rates of detection of viable tumor lesions and false-positive findings after successful diagnostic/radiotherapy.

It has been reported that PSMA is highly homologous to N-acetyl-L-aspartyl-L-glutamate peptidase I, a neuropeptidase that produces the neurotransmitter glutamate and N-acetylaspartate (NAA) through the hydrolysis of N-acetylaspartylglutamate (NAAG). This finding led to the design and development of various classes of small molecules based on different structural motifs, such as phosphorous esters, carbamates or ureas. The urea-based ligands have had the most success in imaging and radiotherapy. PSMA urea-based ligands consist of three components: the binding motif (of which glutamate-urea-lysine [Glu-urea-Lys] is the most widely used scaffold), a linker, and a radiolabel-bearing moiety (chelator molecule for radiolabeling). Upon binding to PSMA, the ligands are internalized. Inside the cells, endosomal recycling increases the deposition, leading to enhanced tumor uptake, retention, and subsequent high image quality for diagnostic procedures and high local dose for therapeutic applications. However, similarly to other small-molecule based imaging tracers, these PSMA ligands display rapid clearance from the circulation, which confers low background early after injection and significantly limits accumulation in prostate cancer tumors.

Several small molecules targeting PSMA were evaluated in prostate cancer patients labeled with betta emitters such as $^{177}$Lu. The most commonly used small molecule, $^{177}$Lu-PSMA-617, is currently under clinical evaluation in many countries. Usual treatment in patients in most clinical trials was composed of up to 3 cycles of $^{177}$Lu-PSMA-617. The limited available data suggests partial response rates of up to 70%-80% that was limited to as few as several weeks in some of the patients. Encouragingly, only stage 1-2 hematologic toxicities and sporadically mild xerostomia and fatigue were reported as side effects, but the long-term toxicity of the drug candidate is yet unknown.

To date, however, no PSMA small molecule has been approved by the U.S. Food and Drug Administration as a diagnostic/therapeutical agent. Therefore, there still remains a need in efficacious and safe small molecule for treatment of prostate cancer.

SUMMARY

In an aspect, the invention is directed to a compound of Formula I or a pharmaceutically acceptable ester, amide, solvate, or salt thereof, or a salt of such an ester or amide or a solvate of such an ester amide or salt,

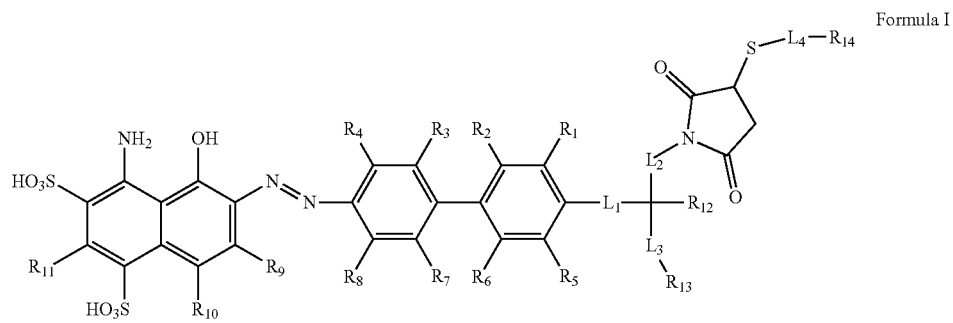

Formula I wherein:
R$_1$, R$_2$, R$_3$, R$_4$, R$_5$, R$_6$, R$_7$, R$_8$, R$_9$, R$_{10}$, and R$_{11}$ are chosen independently from hydrogen, halogen, hydroxyl, cyano, C$_1$-C$_6$alkyl, C$_1$-C$_6$alkoxy, C$_1$-C$_6$haloalkyl, and C$_1$-C$_6$haloalkoxy;
R$_{12}$ is hydrogen, C$_1$-C$_6$alkyl, or C$_1$-C$_6$haloalkyl;
L$_1$ is —(CH$_2$)$_m$— wherein m is an integer from 0 to 12, wherein each CH$_2$ can be individually replaced with —O—, —NH(CO)—, or —(CO)—NH—, provided that no two adjacent CH$_2$ groups are replaced;
L$_2$ is —(CH$_2$)$_n$— wherein n is an integer from 0 to 12, wherein each CH$_2$ can be individually replaced with —O—, —NH(CO)—, or —(CO)—NH—, provided that no two adjacent CH$_2$ groups are replaced;
L$_3$ is —(CH$_2$)$_p$— wherein p is an integer from 0 to 12, wherein each CH$_2$ can be individually replaced with —O—, —NH(CO)—, or —(CO)—NH—, provided that no two adjacent CH$_2$ groups are replaced; and
L$_4$ is a C$_1$-C$_{60}$ linking group, optionally including —O—, —S—, —S(O)—, —S(O)$_2$—, —N(R)—, —C(=O)—, —C(=O)O—, —OC(=O)—, —N(R) C(=O)—, —C(=O)N(R)—, —OC(=O)O—, —N(R)C(=O) O—, or —OC(=O)N(R)—, wherein each R is H or C$_1$-C$_6$ alkyl;
R$_{13}$ is a chelating group; and
R$_{14}$ is a group capable of binding to prostate-specific membrane antigen (PSMA).

In another aspect, the present invention is directed to a pharmaceutical composition comprising one of the above-described compounds, the compound further comprising a radionuclide, together with a pharmaceutically acceptable carrier.

In yet another aspect, the present invention is directed to a method of treating or diagnosing prostate cancer in a mammal, comprising administering to said mammal a therapeutically effective amount of one of the above-described compounds, optionally in combination with one or more additional active ingredients.

These and other aspects will become apparent upon reading the following detailed description of the invention.

BRIEF DESCRIPTION OF THE DRAWINGS

The following description of the invention will be better understood when taken in conjunction with the following drawings in which.

DETAILED DESCRIPTION

Terminology

Figure 1:
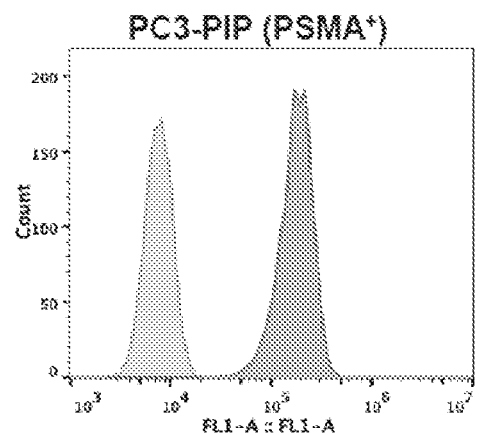
FIG. 1 is a set of graphs showing evaluation of PSMA levels expression by cells using flow cytometry.
Figure 1:
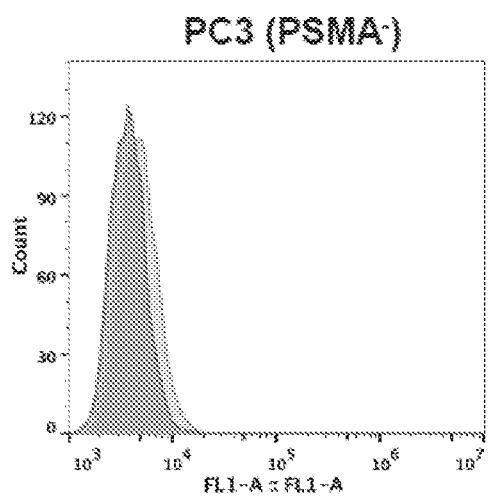
Figure 2:
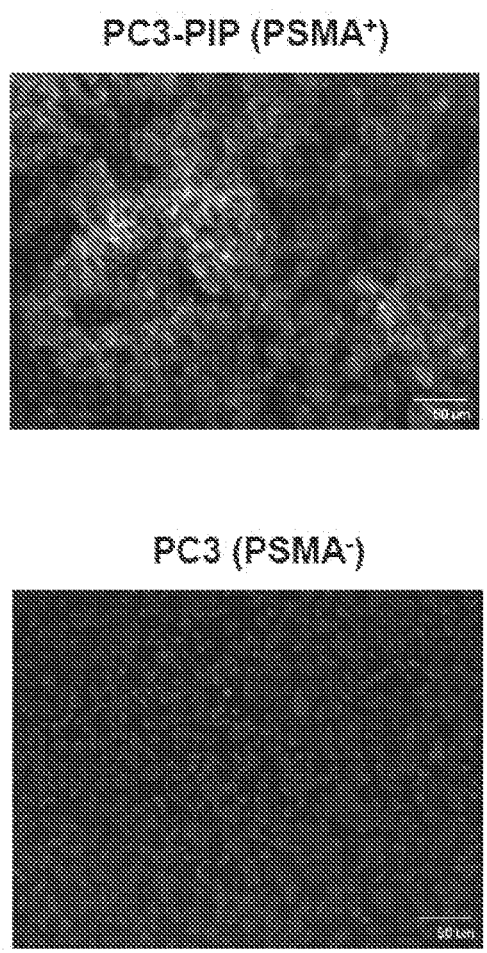
FIG. 2 is a set of images showing evaluation of PSMA levels by cells using immunofluorescence.
Figure 3:
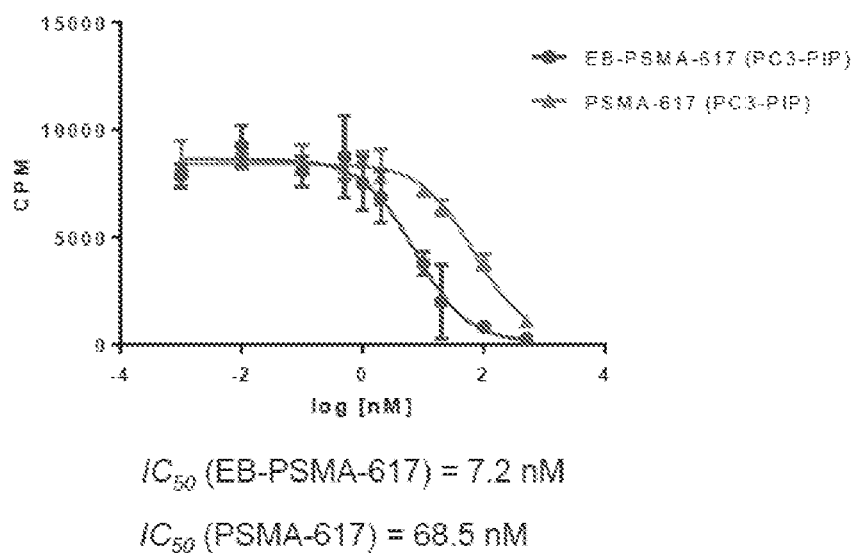
FIG. 3 is a set of graphs illustrating results of PSMA-617 and EB-PSMA-617 binding assays in PSMA$^+$ (PC3-PIP) and PSMA$^-$ (PC3) cells.
Figure 3:
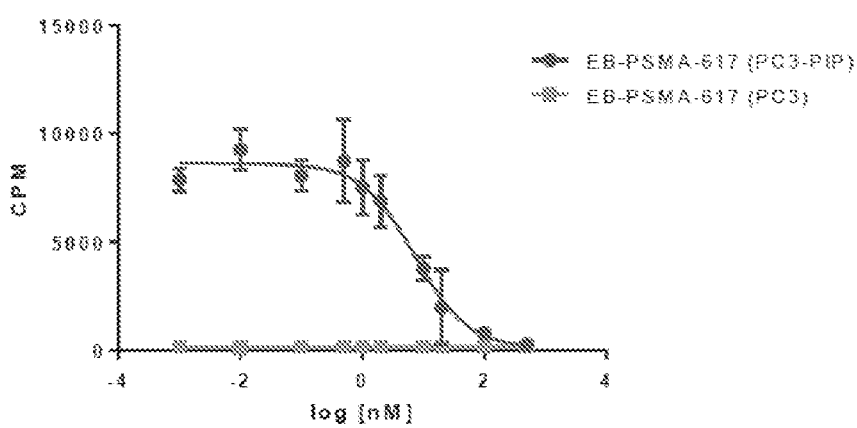
Figure 4:
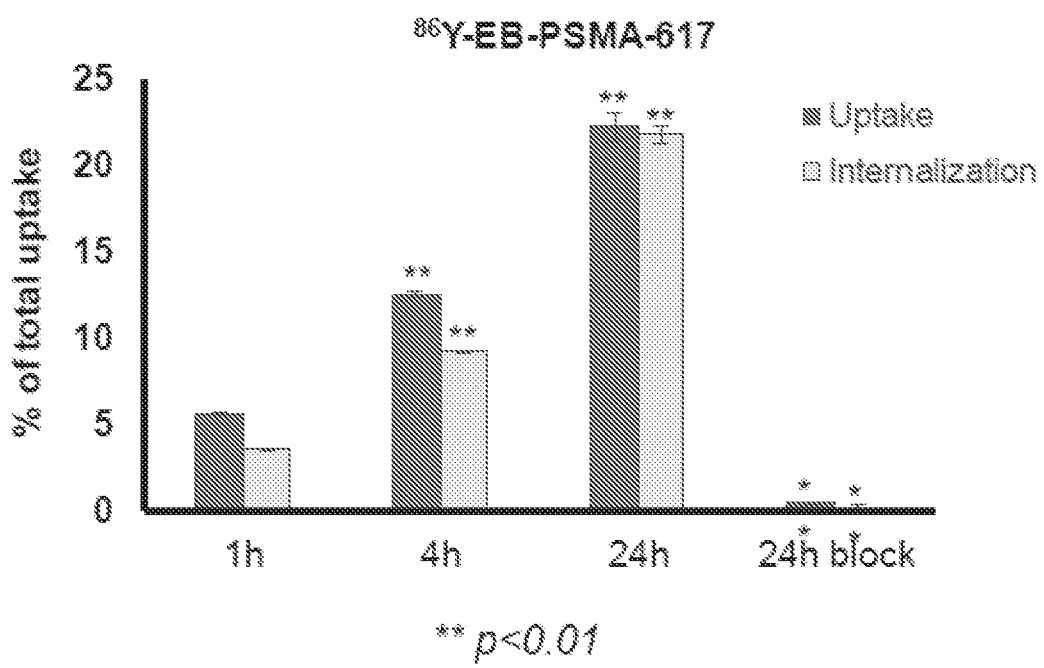
FIG. 4 is a set of diagrams illustrating results of $^{86}$Y-EB-PSMA-617 uptake/internalization/efflux studies in PSMA$^+$ cells.
Figure 4:
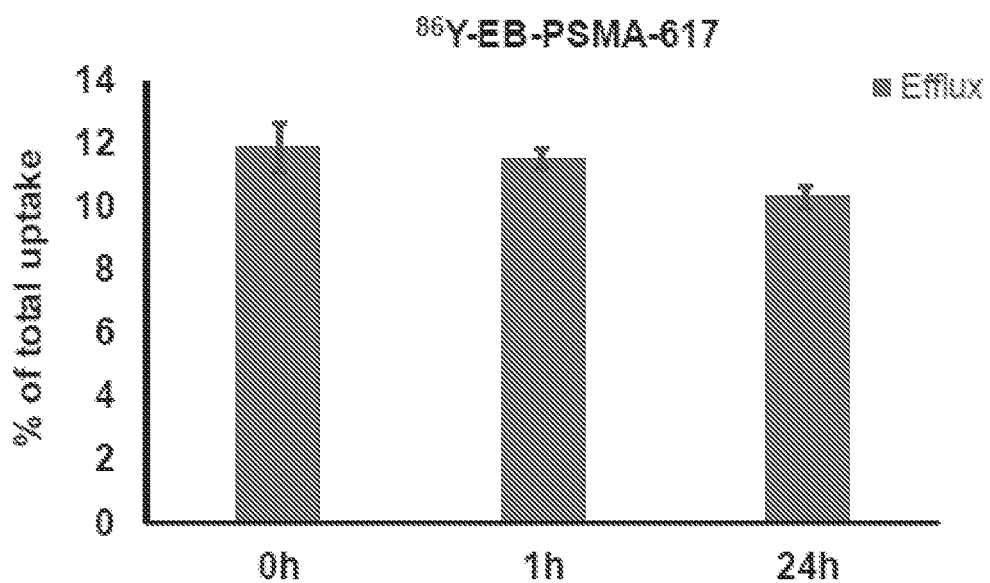
Figure 5:
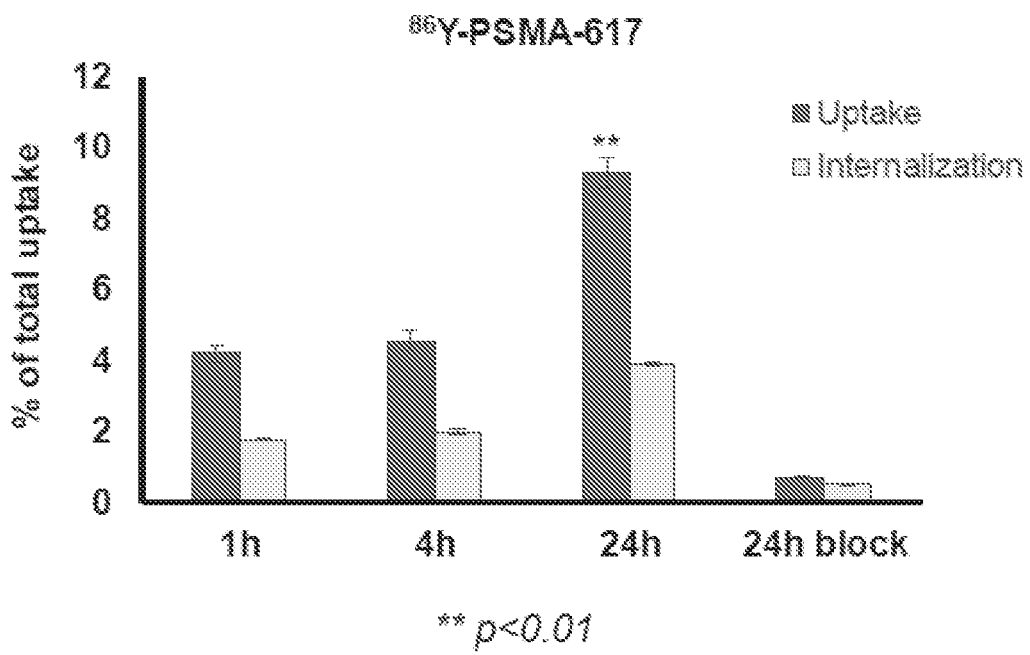
FIG. 5 is a set of diagrams illustrating results of $^{86}$Y-PSMA-617 uptake/internalization/efflux studies in PSMA$^+$ cells.
Figure 5:
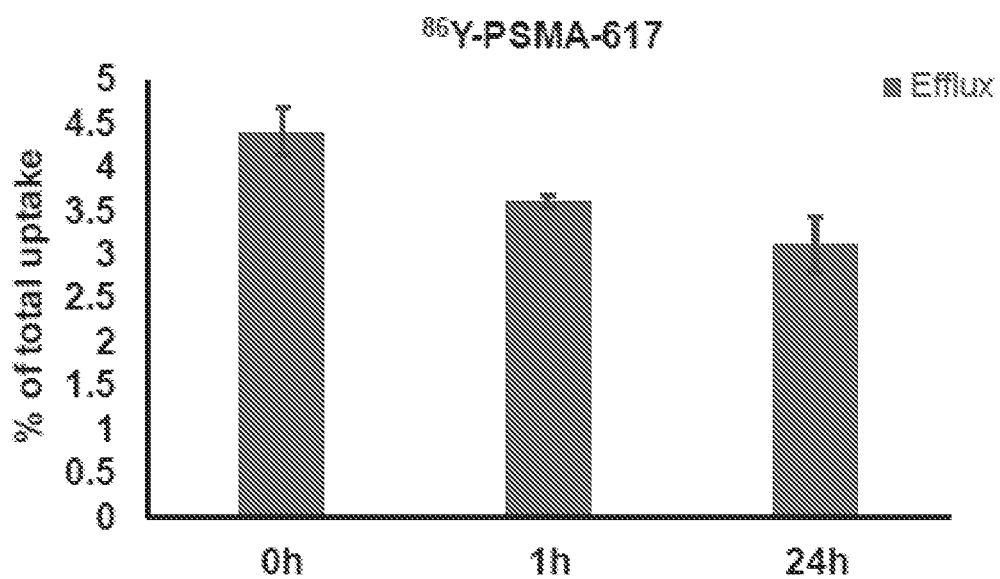
Figure 6:
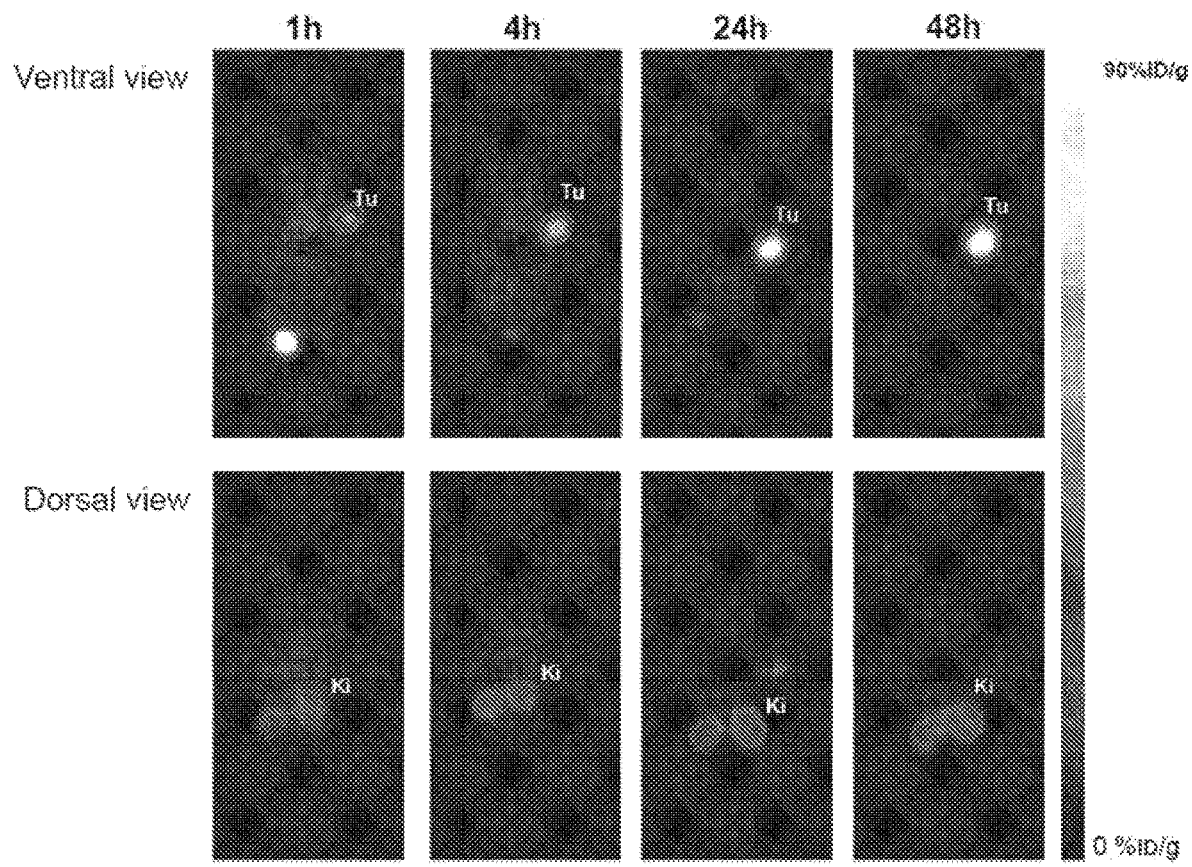
FIG. 6 is a set of images illustrating $^{86}$Y-EB-PSMA-617 PET binding studies and kidneys uptake in PSMA$^+$ tumor model.
Figure 6:
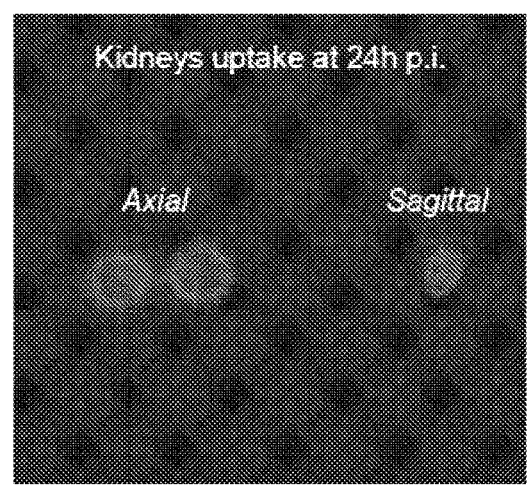
Figure 7:
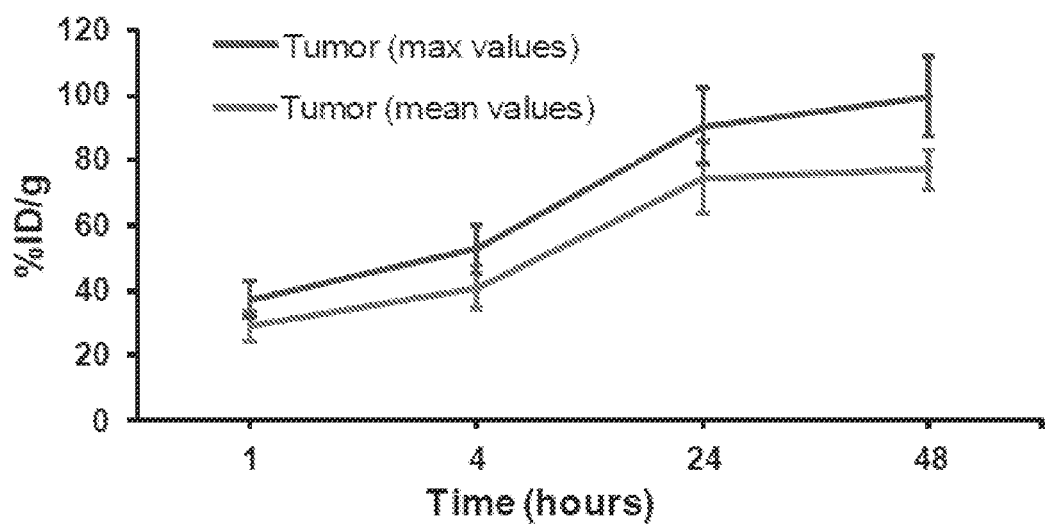
FIG. 7 is a set of graphs illustrating tumor and kidney quantification results obtained in the $^{86}$Y-EB-PSMA-617 PET binding studies.
Figure 7:
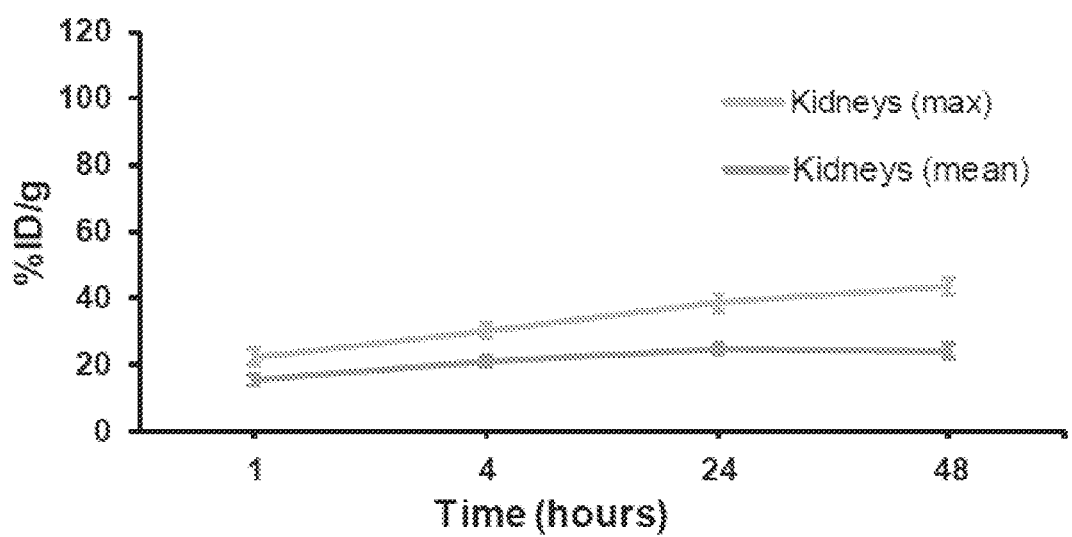
Figure 8:
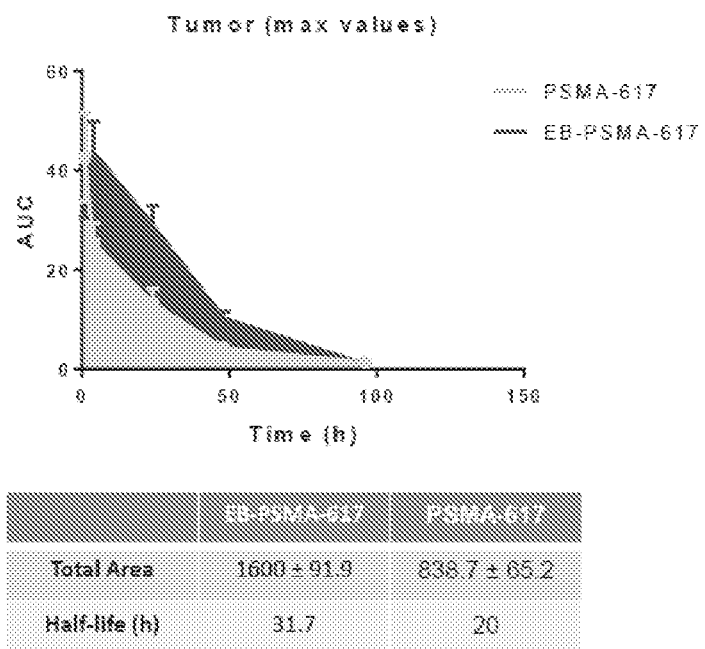
FIG. 8 is a set of graphs illustrating tumor uptake AUC of $^{86}$Y-EB-PSMA-617 and $^{86}$Y-PSMA-617.
Figure 8:
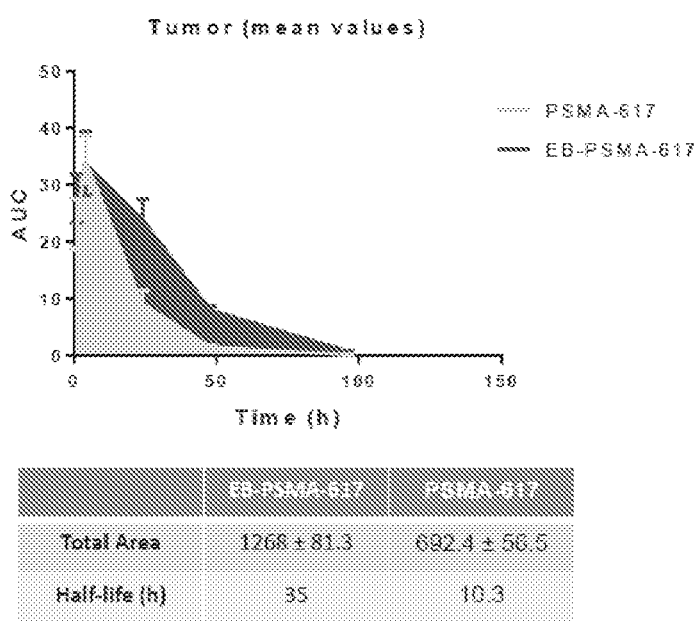
Figure 9:
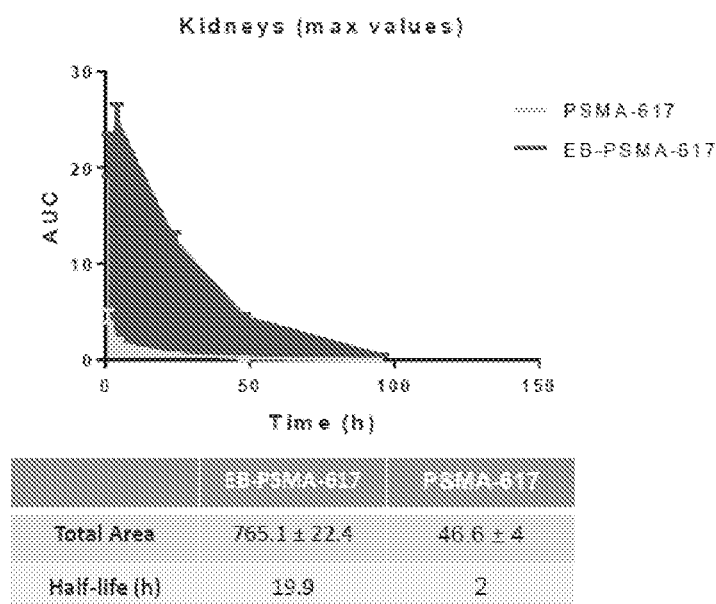
FIG. 9 is a set of graphs illustrating kidneys uptake AUC of $^{86}$Y-EB-PSMA-617 and $^{86}$Y-PSMA-617.
Figure 9:
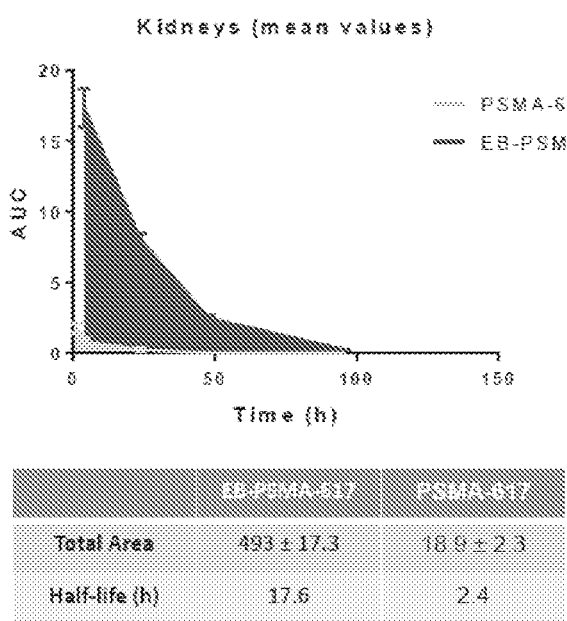
Figure 10:
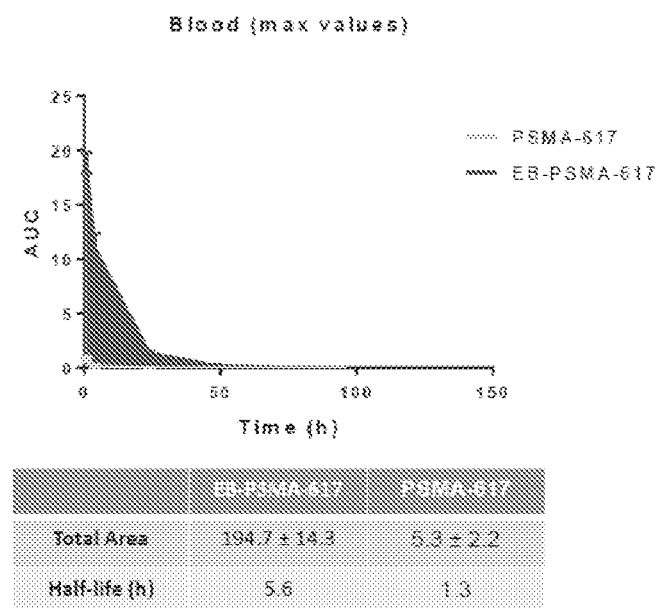
FIG. 10 is a set of graphs illustrating blood uptake AUC of $^{86}$Y-EB-PSMA-617 and $^{86}$Y-PSMA-617.
Figure 10:
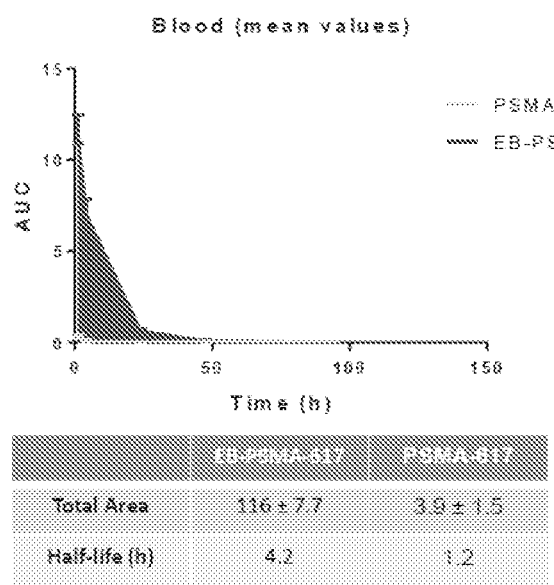
Figure 11:
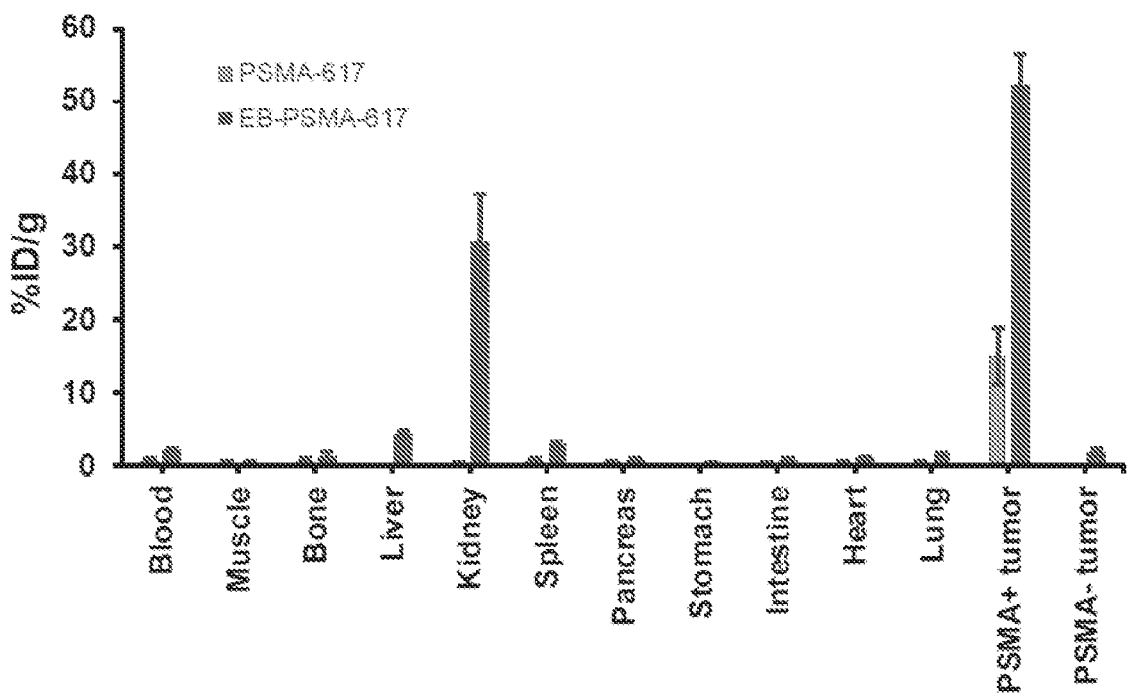
FIG. 11 is a diagram showing biodistribution of $^{86}$Y-EB-PSMA-617 and $^{86}$Y-PSMA-617.
Figure 12:
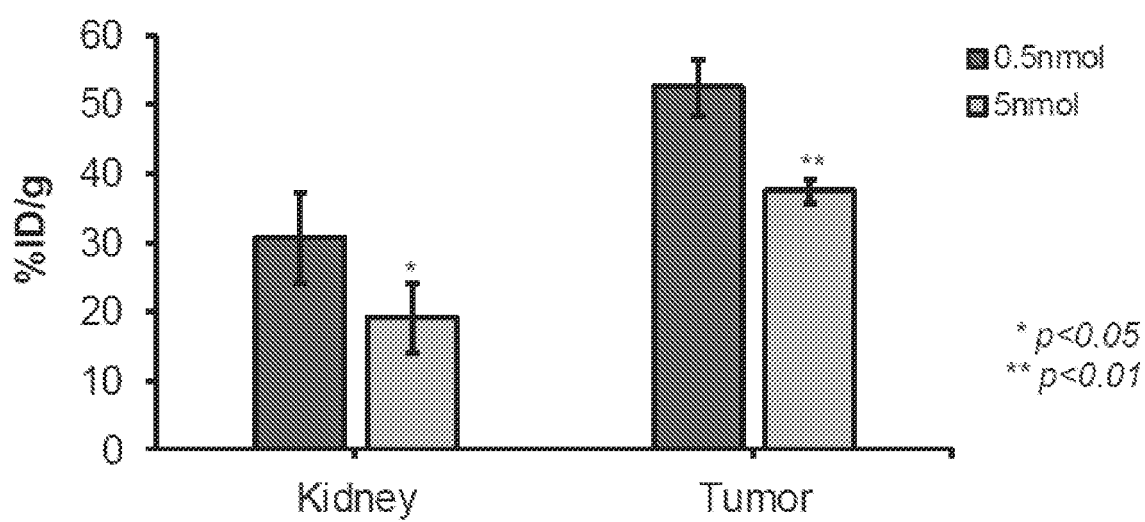
FIG. 12 is a diagram showing $^{86}$Y-EB-PSMA-617 tumor and kidney uptake at different specific activities.
Figure 13:
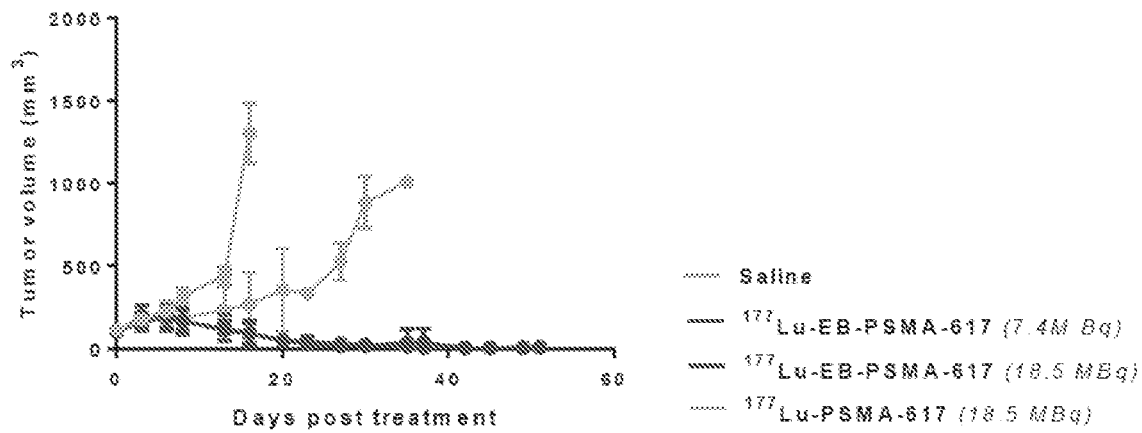
FIG. 13 is a set of diagrams showing $^{177}$Lu-EB-PSMA-617/$^{177}$Lu-PSMA-617 radiotherapy studies in mice bearing PC3-PIP (PSMA$^+$) tumor model.
Figure 13:
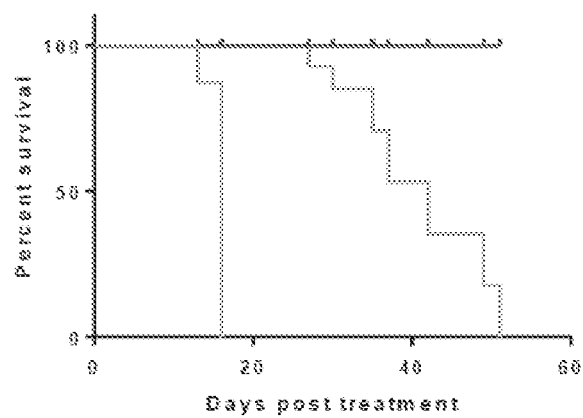
Figure 13:
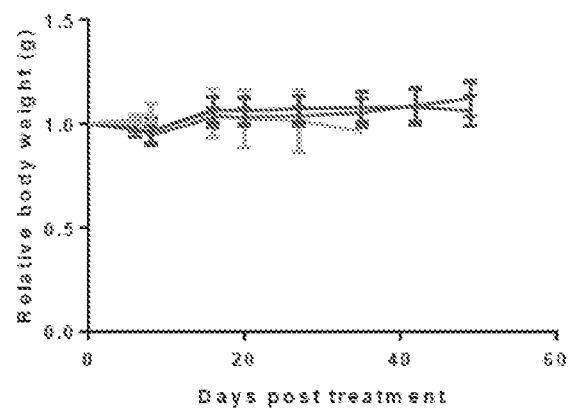
Figure 14:
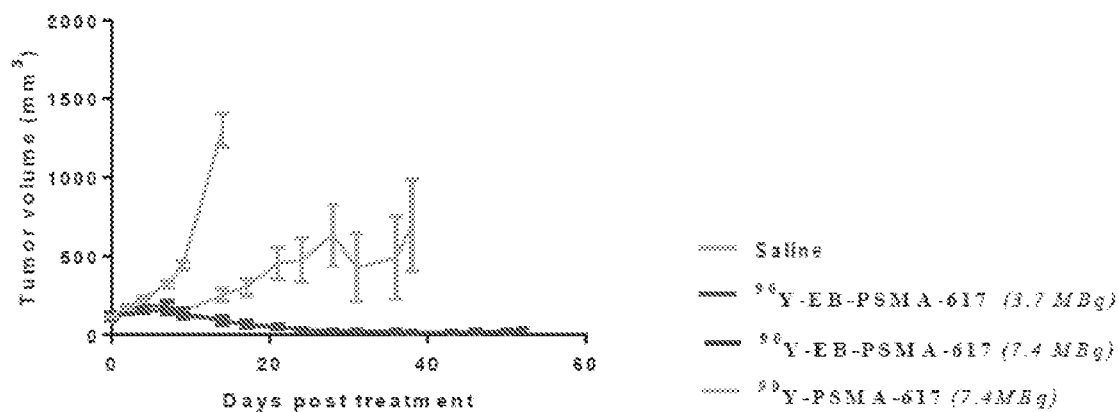
FIG. 14 is a set of diagrams showing $^{90}$Y-EB-PSMA-617/$^{90}$Y-PSMA-617 radiotherapy studies in mice bearing PC3-PIP (PSMA$^+$) tumor model.
Figure 14:
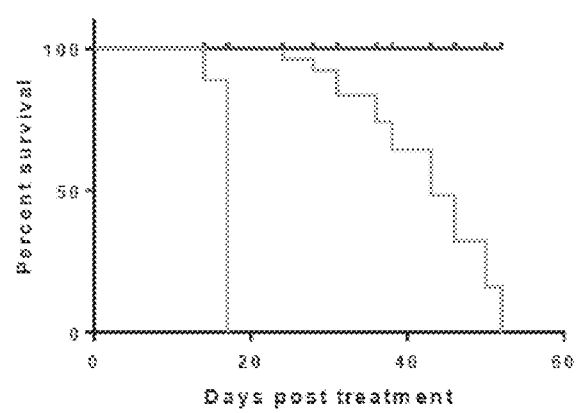
Figure 14:
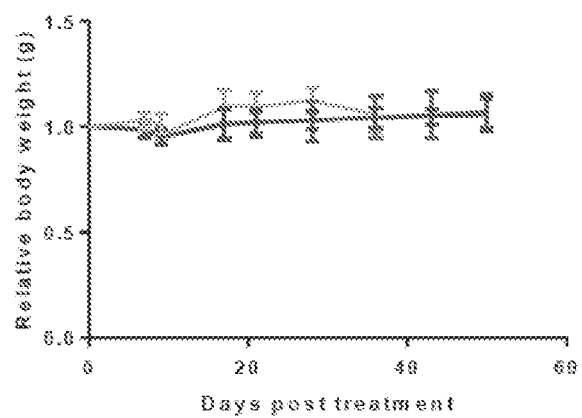
Figure 15:
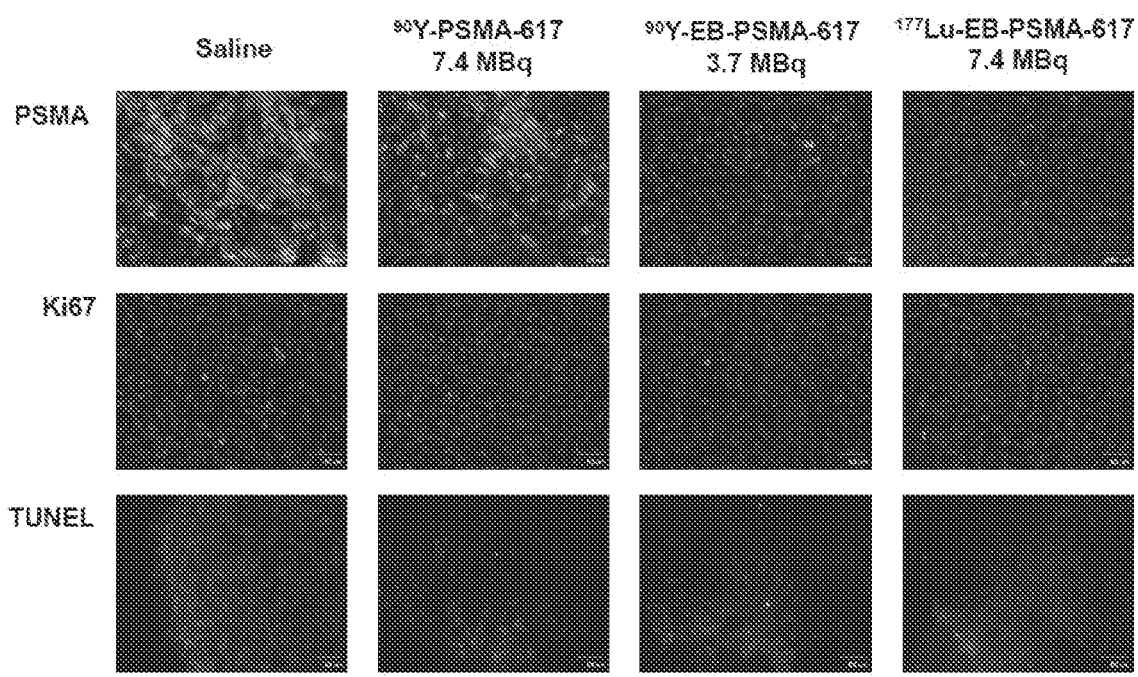
FIG. 15 is a set of images showing staining results after $^{90}$Y-PSMA-617, $^{90}$Y-EB-PSMA-617, and $^{177}$Lu-EB-PSMA-617 radiotherapy treatment.
Figure 16:
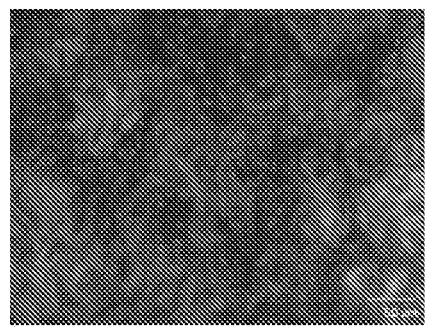
FIG. 16 is a set of images showing PSMA staining of kidneys after $^{90}$Y-EB-PSMA-617 and $^{177}$Lu-EB-PSMA-617 radiotherapy treatment.
Figure 16:
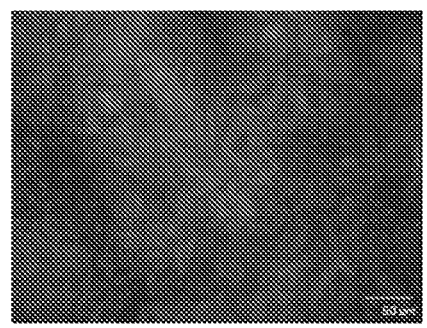
Figure 16:
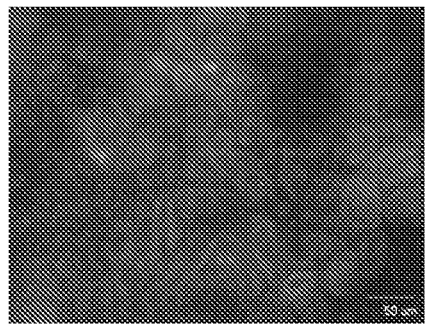
Figure 17:
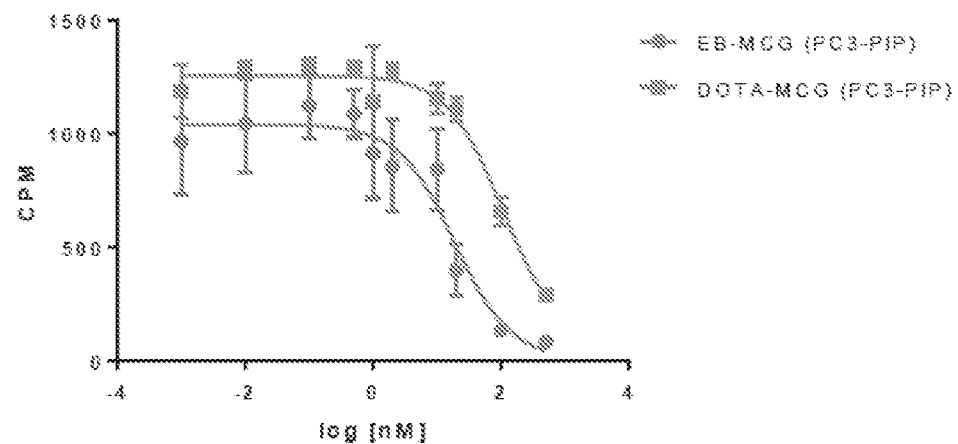
FIG. 17 is a set of graphs illustrating results of EB-MCG and DOTA-MCG binding assays in PSMA$^+$ (PC3-PIP) and PSMA (PC3) cells.
Figure 17:
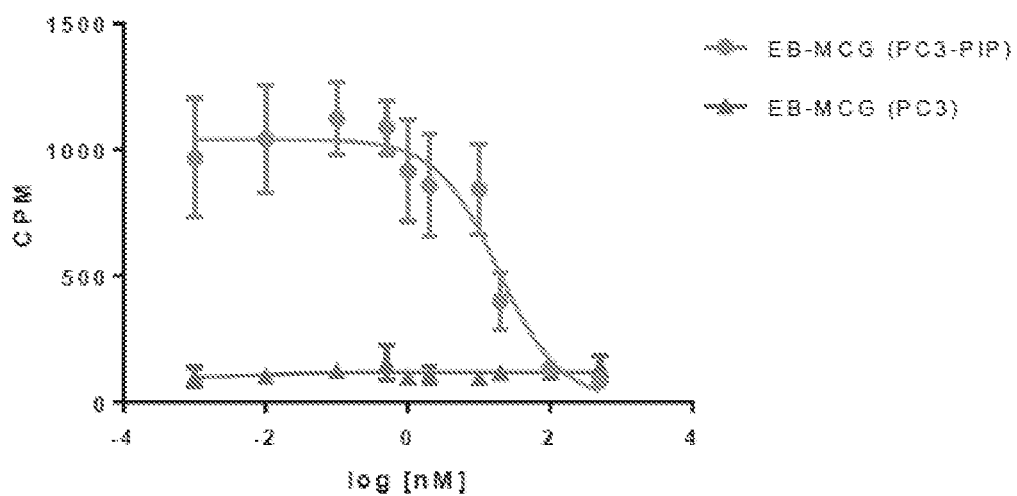
Figure 18:
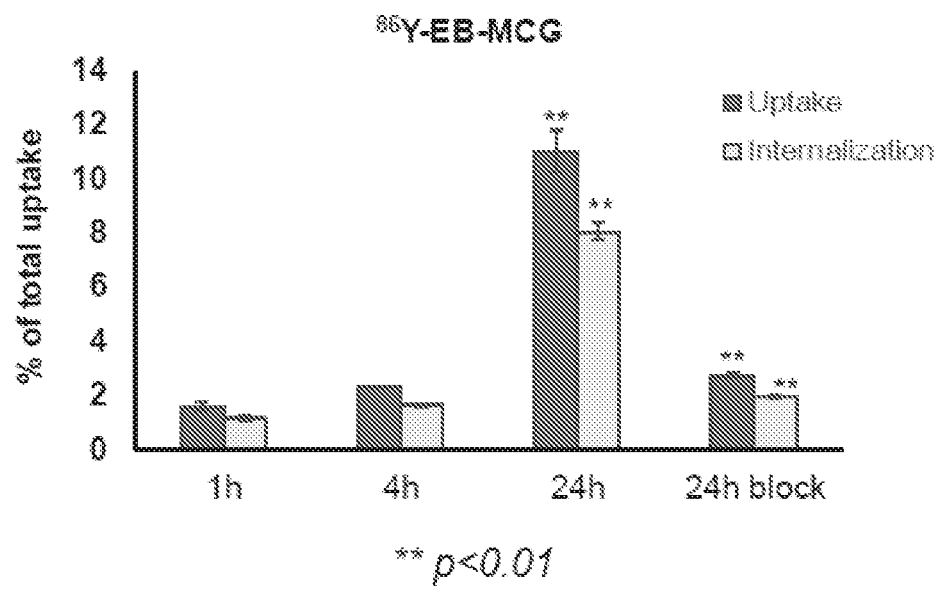
FIG. 18 is a set of diagrams illustrating results of $^{86}$Y-EB-MCG uptake/internalization/efflux studies in PSMA$^+$ cells.
Figure 18:
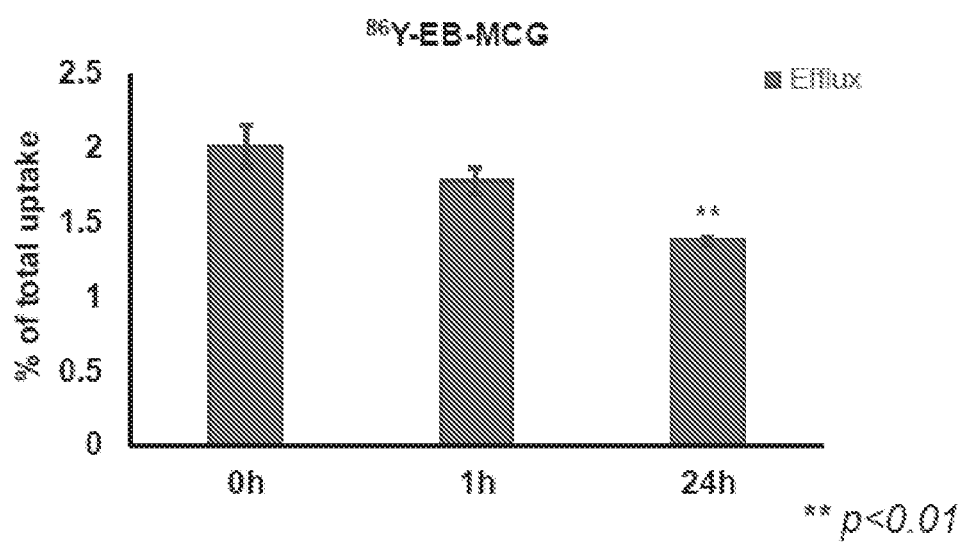
Figure 19:
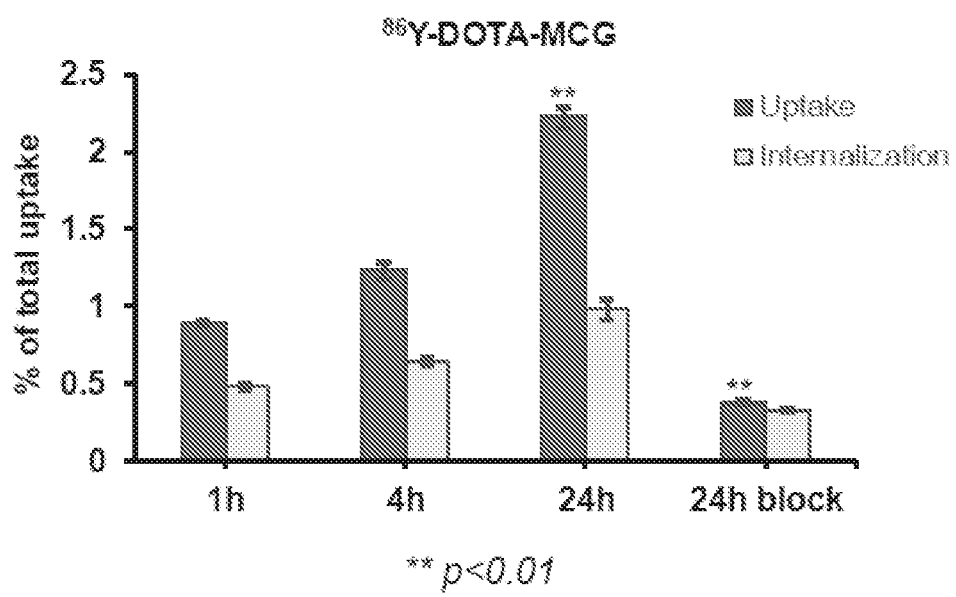
FIG. 19 is a set of diagrams illustrating results of $^{86}$Y-DOTA-MCG uptake/internalization/efflux studies in PSMA$^+$ cells.
Figure 19:
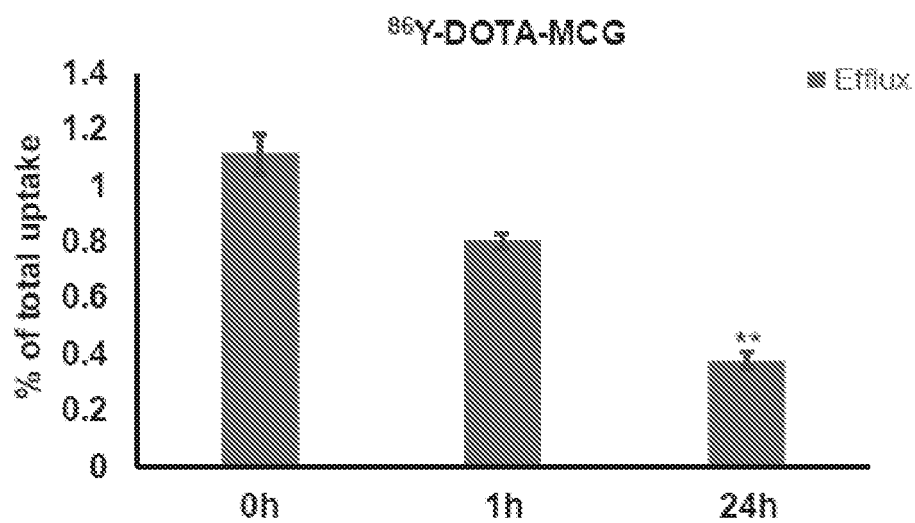
Figure 20:
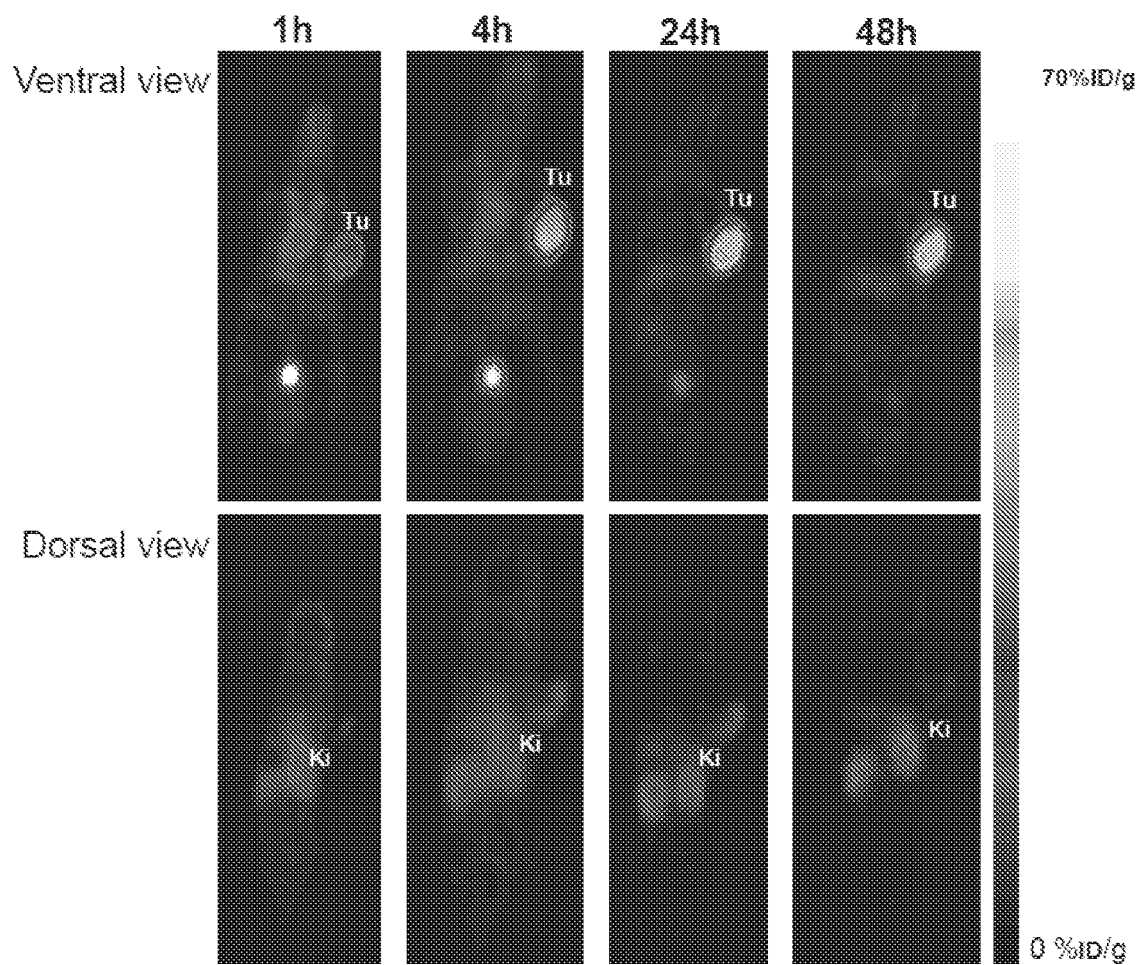
FIG. 20 is a set of images illustrating $^{86}$Y-EB-MCG PET binding studies and kidneys uptake in PSMA$^+$ tumor model.
Figure 21:
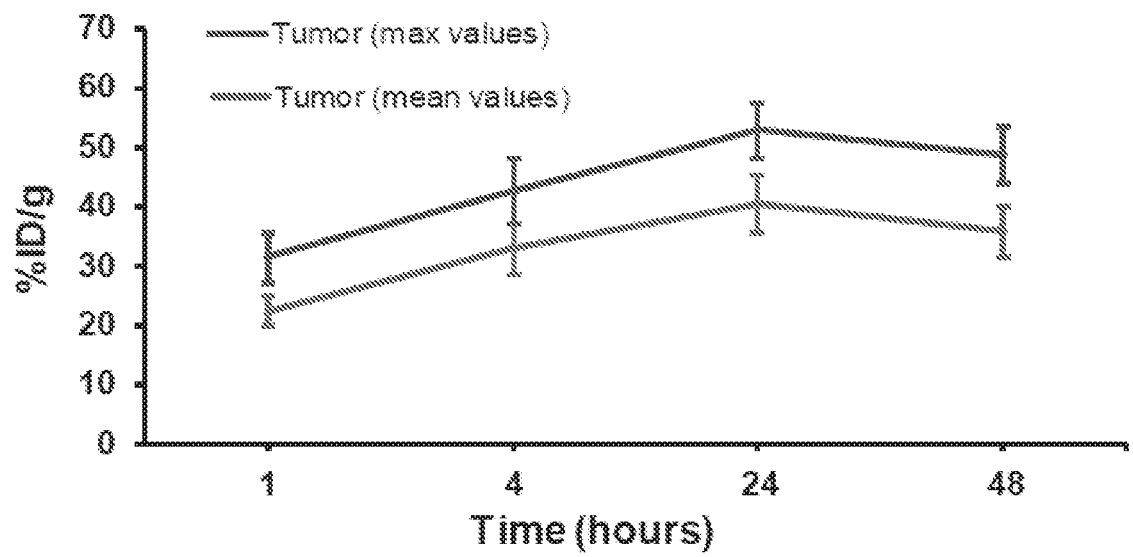
FIG. 21 is a set of graphs illustrating tumor and kidney quantification results obtained in the $^{86}$Y-EB-MCG PET binding studies.
Figure 21:
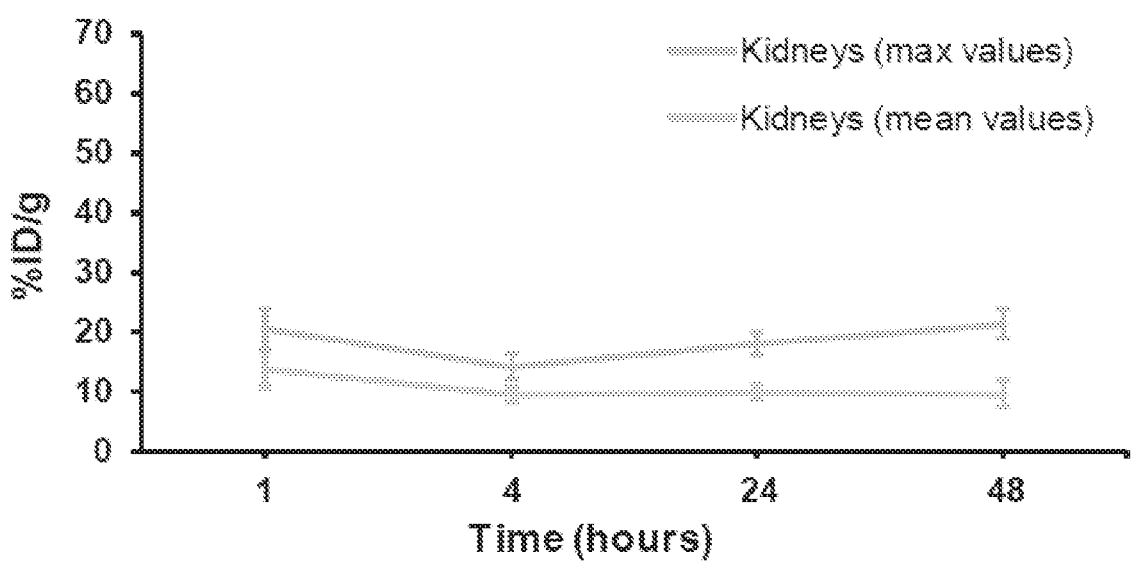
Figure 22:
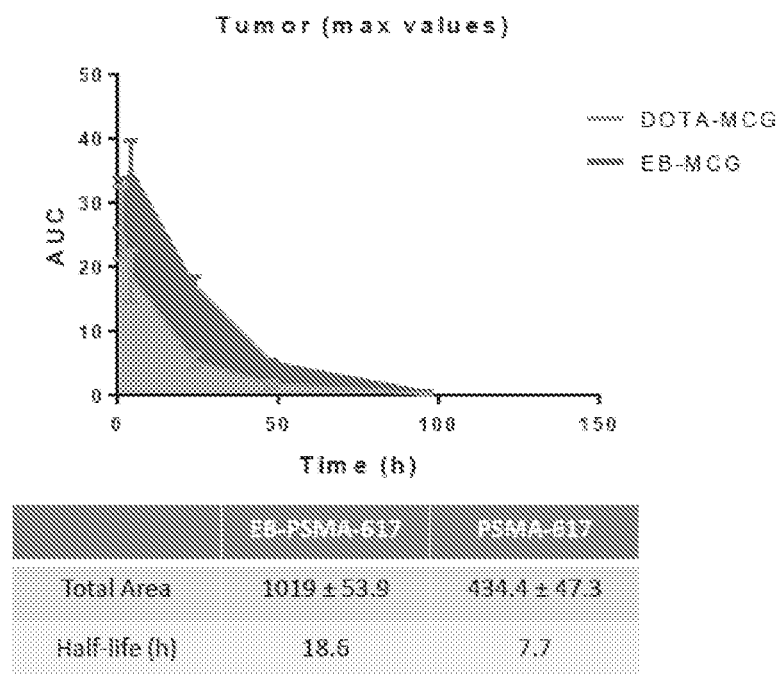
FIG. 22 is a set of graphs illustrating tumor uptake AUC of $^{86}$Y-EB-MCG and $^{86}$Y-DOTA-MCG.
Figure 22:
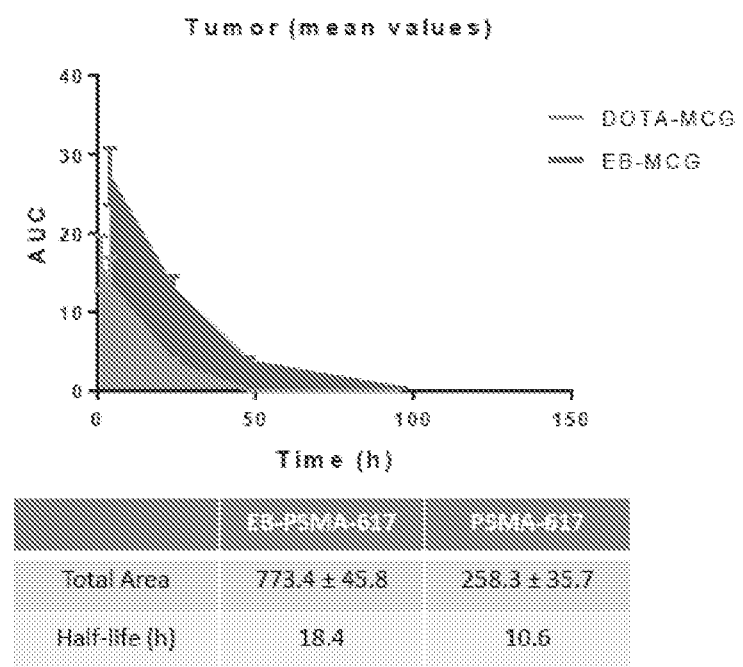
Figure 23:
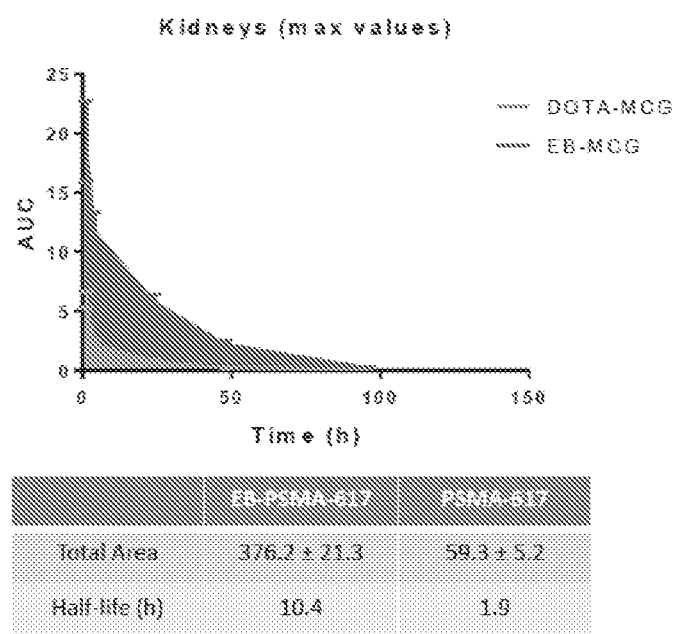
FIG. 23 is a set of graphs illustrating kidneys uptake AUC of $^{86}$Y-EB-MCG and $^{86}$Y-DOTA-MCG.
Figure 23:
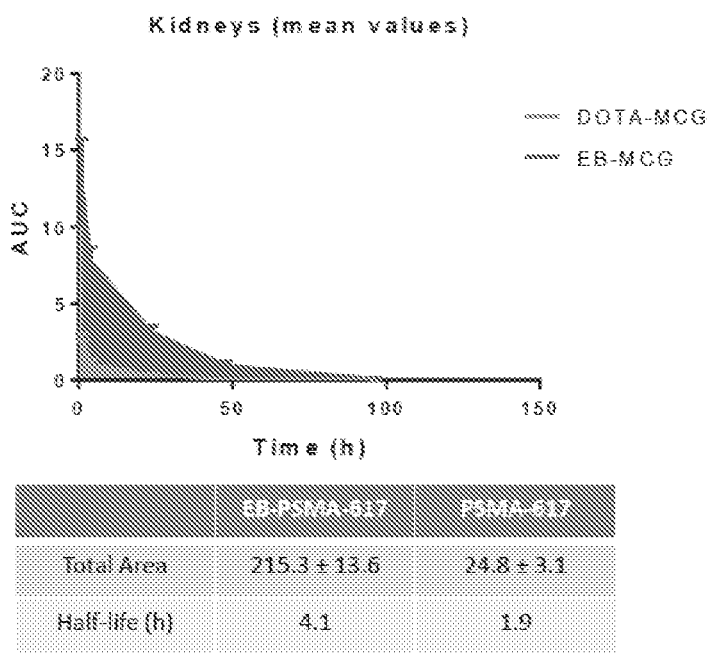
Figure 24:
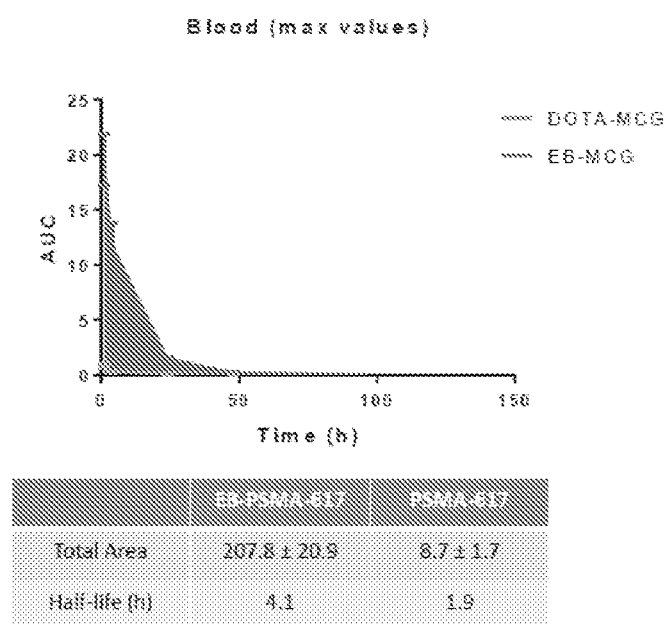
FIG. 24 is a set of graphs illustrating blood uptake AUC of $^{86}$Y-EB-MCG and $^{86}$Y-DOTA-MCG.
Figure 24:
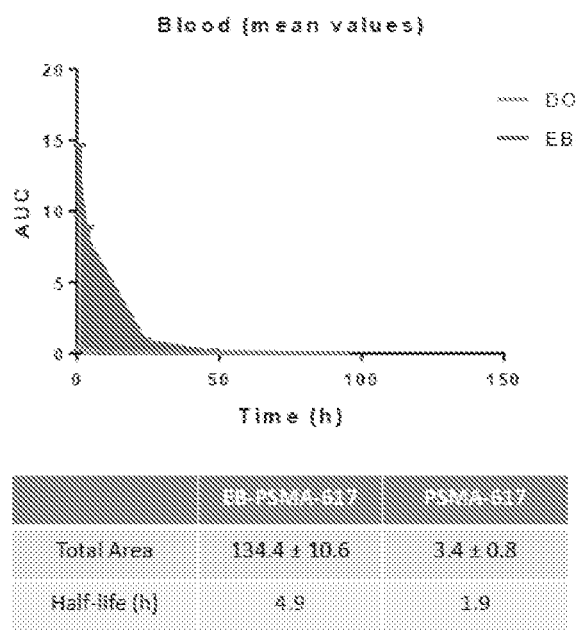
Figure 25:
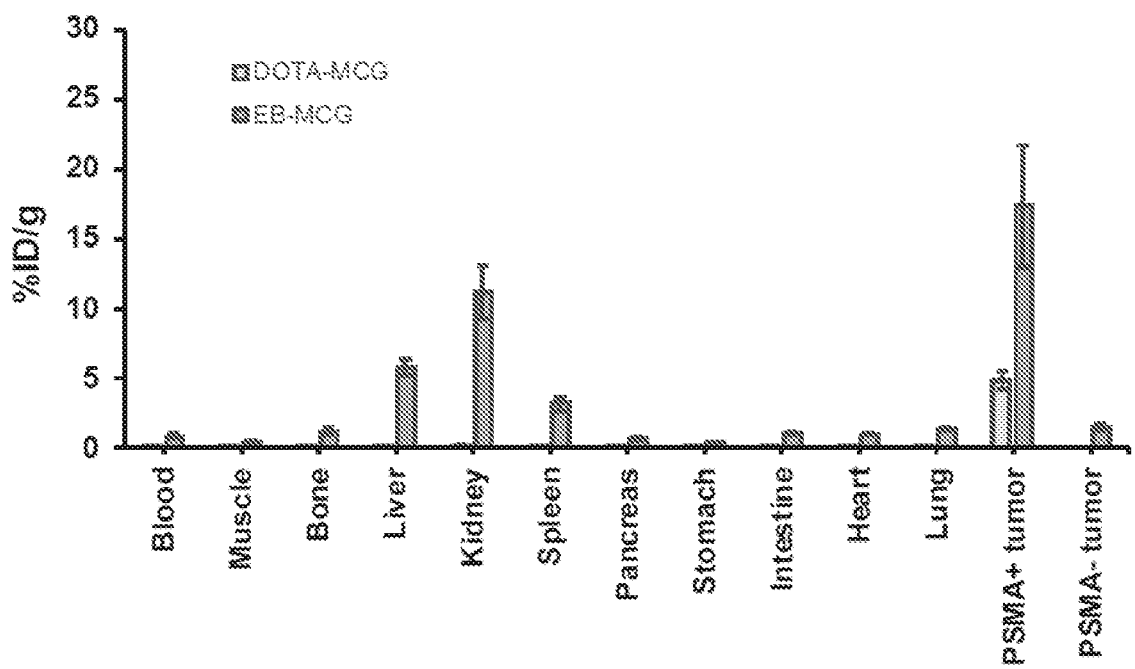
FIG. 25 is a diagram showing biodistribution of $^{86}$Y-EB-MCG and $^{86}$Y-DOTA-MCG.
Figure 26:
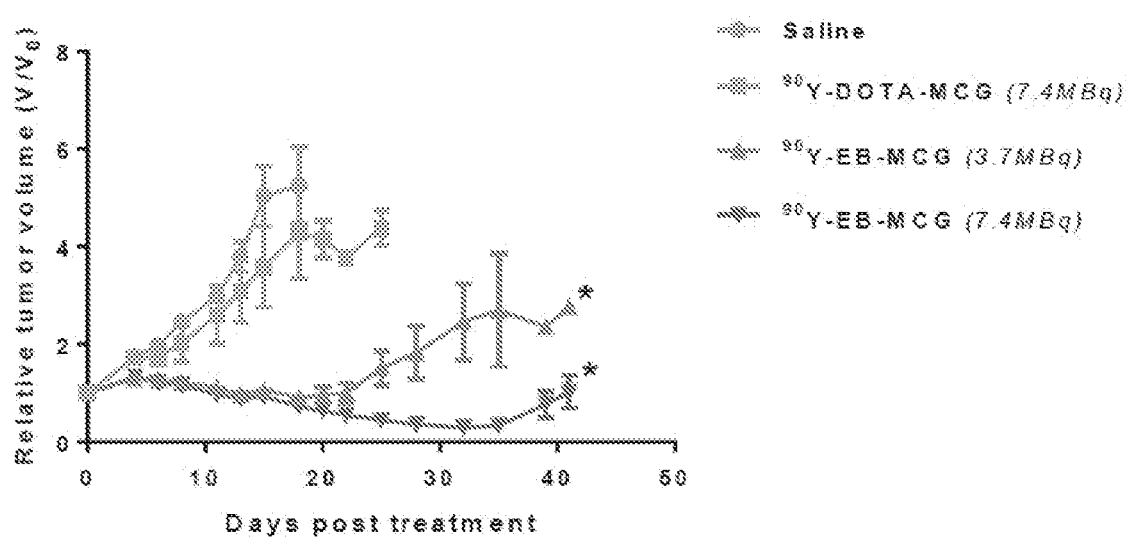
FIG. 26 is a diagram showing $^{90}$Y-EB-MCG and $^{90}$Y-DOTA-MCG radiotherapy studies in mice bearing PC3-PIP (PSMA$^+$) tumor model.
Figure 27:
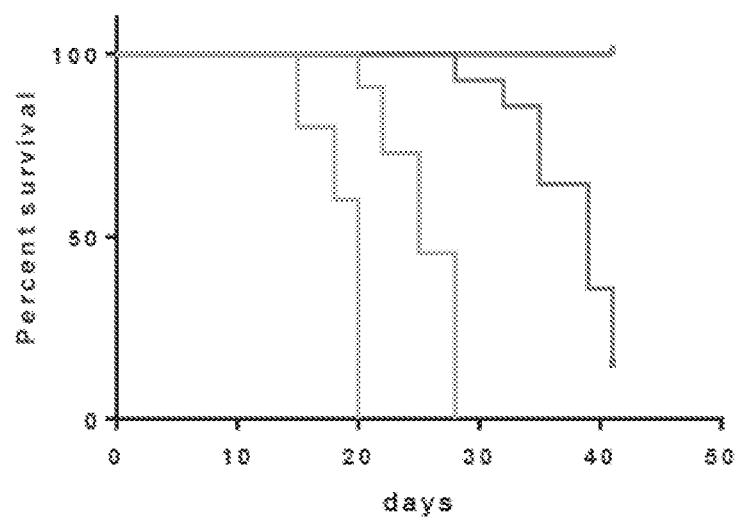
FIG. 27 is a set of images showing $^{90}$Y-EB-MCG and $^{90}$Y-DOTA-MCG survival and body weight changes.
Figure 27:
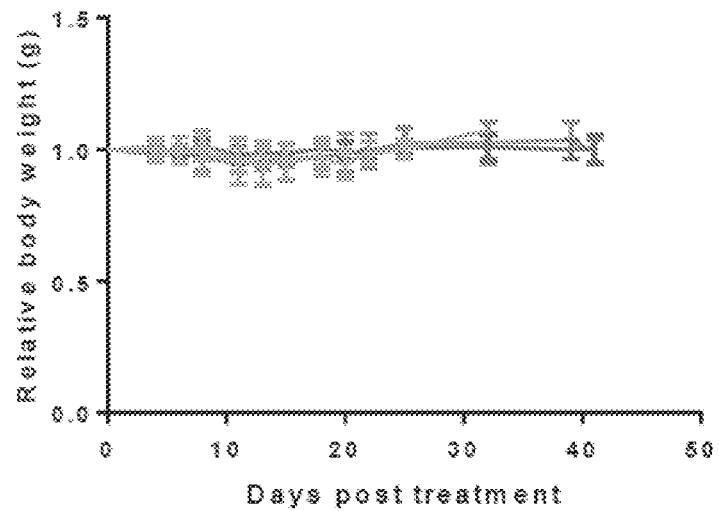
Figure 28:
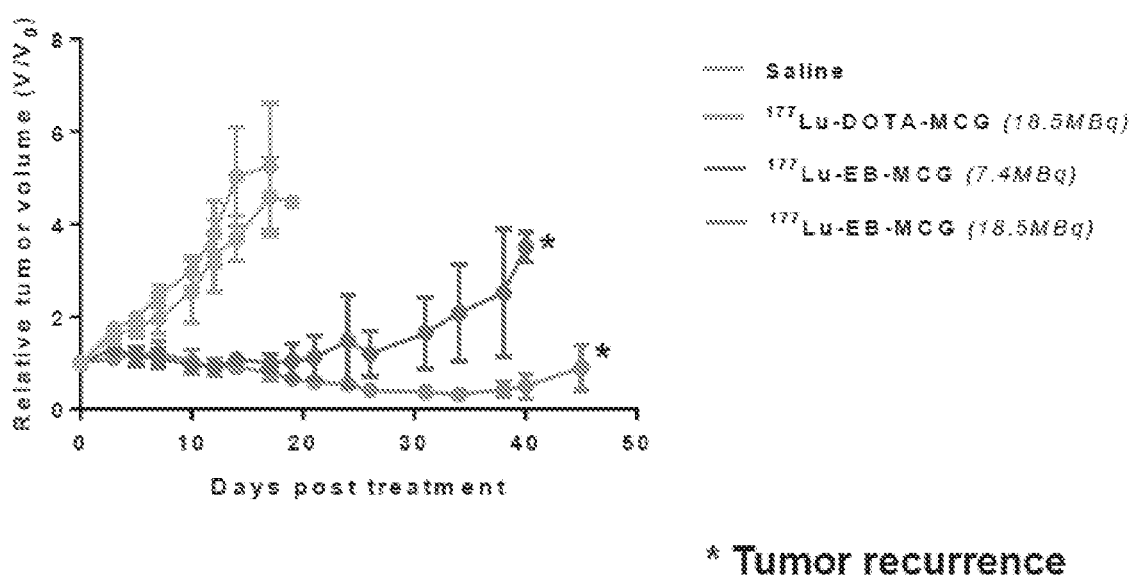
FIG. 28 is a set of diagrams showing $^{177}$Lu-EB-MCG/$^{177}$Lu-DOTA-MCG radiotherapy studies in mice bearing PC3-PIP (PSMA$^+$) tumor model.
Figure 29:
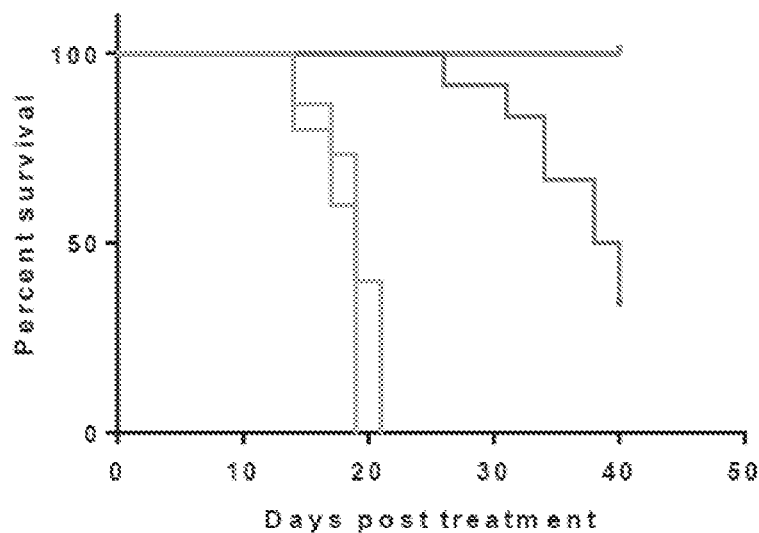
FIG. 29 is a set of images showing $^{177}$Lu-EB-MCG/$^{177}$Lu-DOTA-MCG survival and body weight changes.
Figure 29:
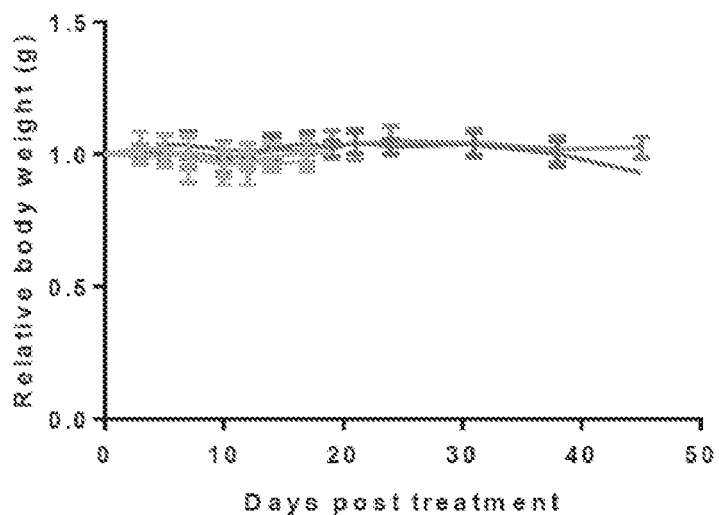
Figure 30:
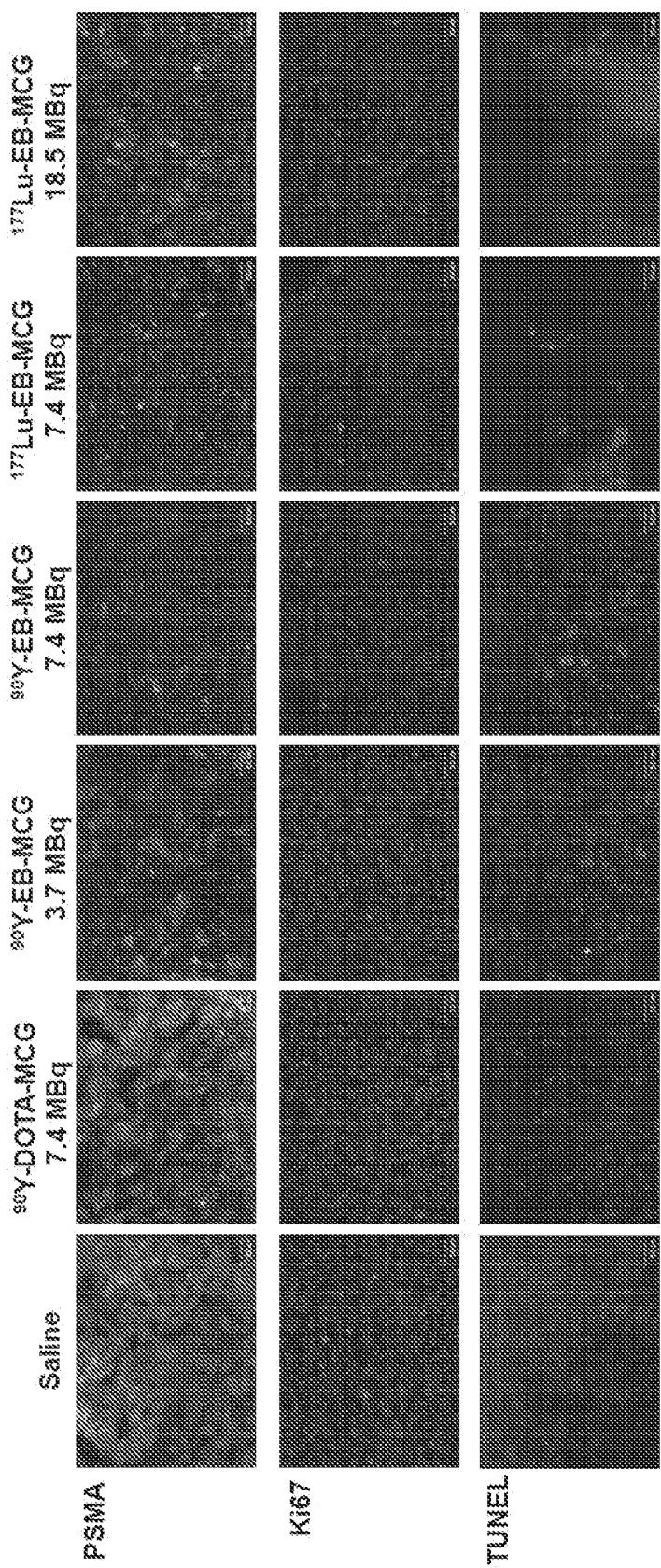
FIG. 30 is a set of images showing staining results after $^{90}$Y-DOTA-MCG, $^{90}$Y-EB-MCG, and $^{177}$Lu-EB-MCG radiotherapy treatment.
Figure 31:
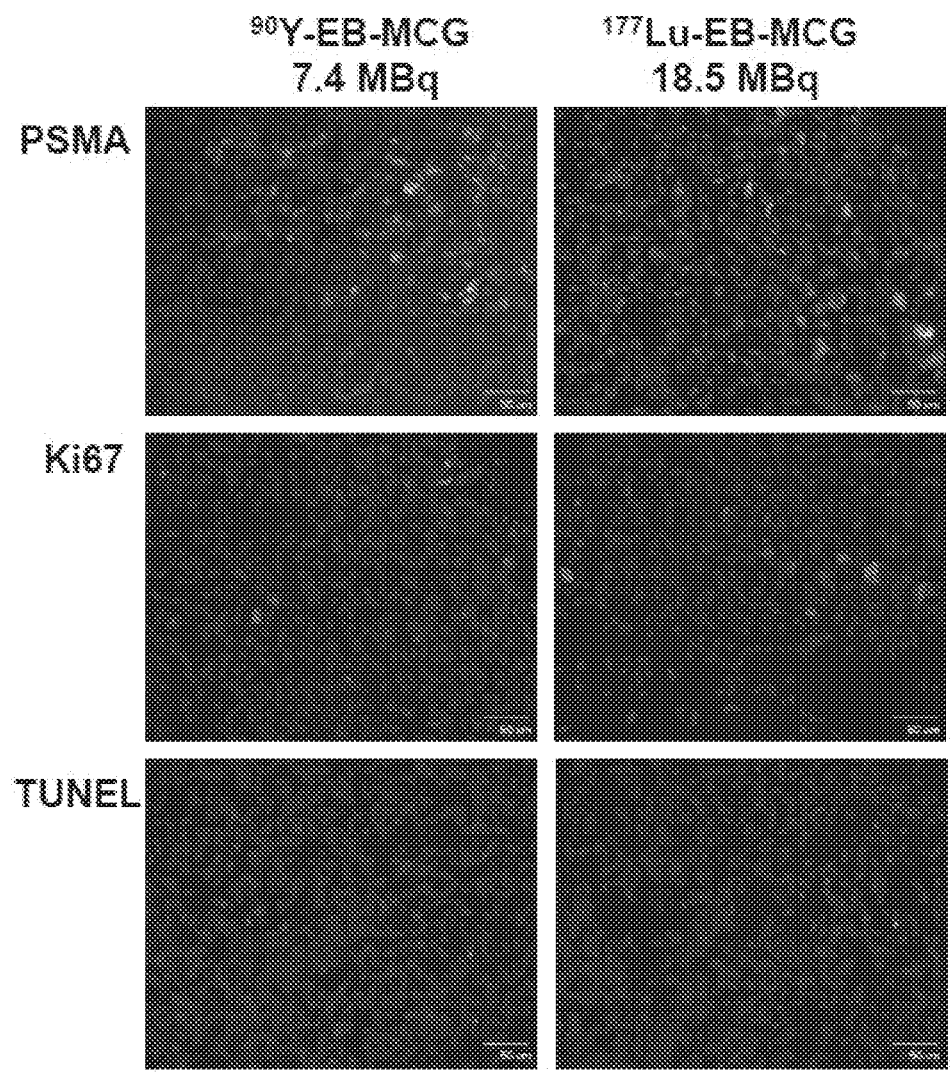
FIG. 31 is a set of images showing $^{90}$Y-EB-MCG and $^{177}$Lu-EB-MCG staining results after tumor recurrence.
Figure 32:
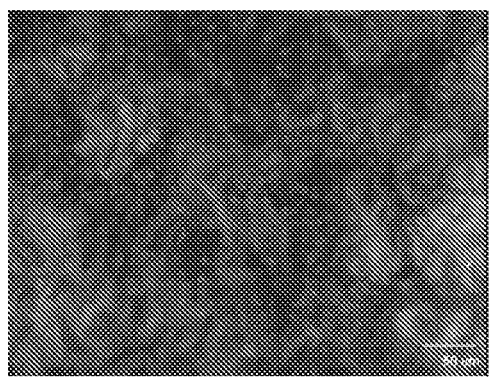
FIG. 32 is a set of images showing PSMA staining of kidneys after $^{90}$Y-EB-MCG and $^{177}$Lu-EB-MCG radiotherapy treatment.
Figure 32:
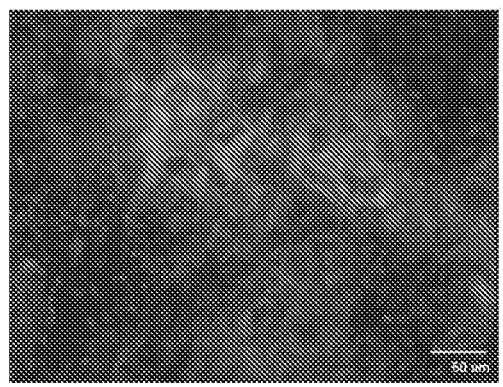
Figure 32:
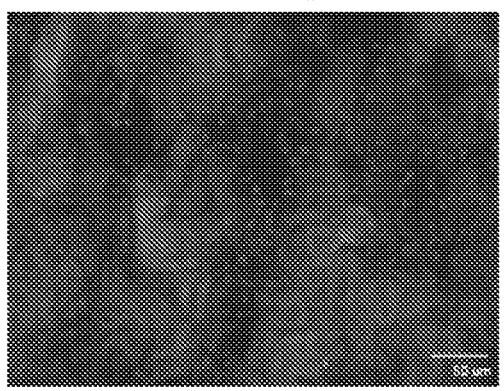

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers and encompass heavy isotopes and radioactive isotopes. By way of general example, and without limitation, isotopes of hydrogen include tritium and deuterium, and isotopes of carbon include $^{11}C$, $^{13}C$, and $^{14}C$. Accordingly, the compounds disclosed herein may include heavy or radioactive isotopes in the structure of the compounds or as substituents attached thereto. Examples of useful heavy or radioactive isotopes include $^{18}F$, $^{15}N$, $^{18}O$, $^{76}Br$, $^{125}I$ and $^{131}I$.

Formulae I and II include all pharmaceutically acceptable salts of Formulae I and II.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent.

"Alkyl" includes both branched and straight chain saturated aliphatic hydrocarbon groups, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g., $C_1$-$C_8$alkyl, $C_1$-$C_4$alkyl, and $C_1$-$C_2$alkyl. When $C_0$-$C_n$ alkyl is used herein in conjunction with another group, for example, —$C_0$-$C_2$alkyl (phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$—$C_4$alkyl ($C_3$-$C_7$cycloalkyl). Examples of alkyl include, but are not limited to, methyl, ethyl, n-propyl, iso-propyl, n-butyl, 3-methylbutyl, 1-butyl, n-pentyl, and sec-pentyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, iso-propoxy, n-butoxy, 2-butoxy, 1-butoxy, n-pentoxy, 2-pentoxy, 3-pentoxy, iso-pentoxy, neo-pentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound to the group it substitutes by a sulfur bridge (—S—). Similarly, "alkenyloxy", "alkynyloxy", and "cycloalkyloxy" refer to alkenyl, alkynyl, and cycloalkyl groups, in each instance covalently bound to the group it substitutes by an oxygen bridge (—O—).

"Halo" or "halogen" means fluoro, chloro, bromo, or iodo, and are defined herein to include all isotopes of same, including heavy isotopes and radioactive isotopes. Examples of useful halo isotopes include $^{18}F$, $^{76}Br$, and $^{131}I$. Additional isotopes will be readily appreciated by one of skill in the art.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined above attached through an oxygen bridge (oxygen of an alcohol radical).

"Peptide" means a molecule which is a chain of amino acids linked together via amide bonds (also called peptide bonds).

"Pharmaceutical compositions" means compositions comprising at least one active agent, such as a compound or salt of Formula I, and at least one other substance, such as a carrier. Pharmaceutical compositions meet the U.S. Food and Drug Administration's good manufacturing practice (GMP) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any disease symptom, slow disease progression or cause disease regression. In certain embodiments treatment of the disease may be commenced before the patient presents symptoms of the disease.

A "therapeutically effective amount" of a pharmaceutical composition means an amount effective, when administered to a patient, to provide a therapeutic benefit such as an amelioration of symptoms, decrease disease progression, or cause disease regression.

A "therapeutic compound" means a compound which can be used for diagnosis or treatment of a disease. The compounds can be small molecules, peptides, proteins, or other kinds of molecules.

A significant change is any detectable change that is statistically significant in a standard parametric test of statistical significance such as Student's T-test, where $p<0.05$.

Chemical Description

Compounds of Formulae I and II may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

A "chelating group" or "chelator" is a ligand group which can form two or more separate coordinate bonds to a single central atom, which is usually a metal ion. Chelating groups as disclosed herein are organic groups which possess multiple N, O, or S heteroatoms, and have a structure which allows two or more of the heteroatoms to form bonds to the same metal ion.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, iso-propanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like. Lists of additional suitable salts may be found, e.g., in G. Steffen Paulekuhn, et al., Journal of Medicinal Chemistry 2007, 50, 6665 and Handbook of Pharmaceutically Acceptable Salts: Properties, Selection and Use, P. Heinrich Stahl and Camille G. Wermuth, Editors, Wiley-VCH, 2002.

Embodiments

An aspect the present invention encompasses chemical conjugates of Evans Blue dye having the compound of Formula I illustrated below, or a pharmaceutically acceptable ester, amide, solvate, or salt thereof, or a salt of such an ester or amide or a solvate of such an ester amide or salt:

In yet another embodiment of Formula I, $R_1$ and $R_4$ are each methyl.

In yet another embodiment of Formula I, $R_{12}$ is hydrogen.

$R_{13}$ may be a chelating group. In some embodiments, the chelating group may be a macrocyclic moiety, such as a NOTA group, a DOTA group, mercaptoacetyltriglycine ($MAG_3$), dipicolylamine ethanoic acid (DPA), cyclodextrin, crown ether, or porphyrin, or may be a linear moiety such as a 1,4,7-triazaheptane-1,4,7,7-tetracetic acid group (DTPA), but is not limited thereto. Chemical structures of these and some other compounds and groups are shown below.

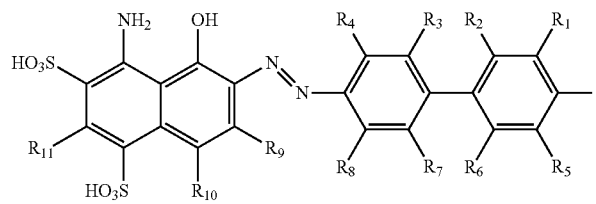
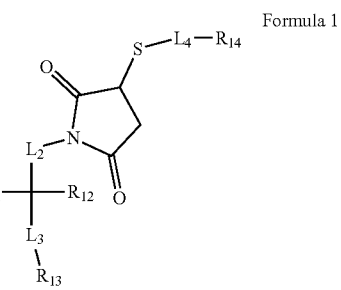

Formula 1

In Formula I, the substituents $R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy. $R_{12}$ is hydrogen, $C_1$-$C_6$alkyl, or $C_1$-$C_6$haloalkyl. $R_{13}$ is a chelating group. $R_{14}$ is group capable of binding to prostate-specific membrane antigen (PSMA).

Formula I may also include linking group $L_1$ which is —$(CH_2)_m$— wherein m is an integer from 0 to 12; linking group $L_2$ which is —$(CH_2)_n$— wherein n is an integer from 0 to 12; and linking group $L_3$ which is —$(CH_2)_p$— wherein p is an integer from 0 to 12. In each of $L_1$, $L_2$, and $L_3$, each $CH_2$ can be individually replaced with —O—, —NH(CO)—, or —(CO)—NH—, provided that no two adjacent $CH_2$ groups are replaced.

In some embodiments, the linking groups $L_1$-$L_3$ include polyethylene glycol segments —$CH_2CH_2O$—.

In an embodiment of Formula I, $L_1$ is —NH(CO)—. In another embodiment of Formula I, $L_2$ is —$(CH_2)_4$—NH(CO)—$(CH_2)_2$—. In yet another embodiment of Formula I, $L_3$ is —NH(CO)$CH_2$—.

Formula I may also include linking group La which is a $C_1$-$C_{60}$ linking group, optionally including —O—, —S—, —S(O)—, —S(O)$_2$—, —N(R)—, —C(=O)—, —C(=O)O—, —OC(=O)—, —N(R)C(=O)—, —C(=O)N(R)—, —OC(=O)O—, —N(R)C(=O)O—, or —OC(=O)N(R)—, wherein each R is H or $C_1$-$C_6$ alkyl. In an embodiment, $L_4$ may include —$(CH_2)_q$— wherein q is an integer from 0 to 12, wherein each $CH_2$ can be individually replaced with —O—, —NH(CO)—, or —(CO)—NH—, provided that no two adjacent $CH_2$ groups are replaced.

In yet another embodiment of Formula I, $R_1$ and $R_4$ are chosen independently from halogen, hydroxyl, cyano, $C_1$-$C_6$alkyl, $C_1$-$C_6$alkoxy, $C_1$-$C_6$haloalkyl, and $C_1$-$C_6$haloalkoxy.

In yet another embodiment of Formula I, $R_2$, $R_3$, $R_5$, $R_6$, $R_7$, $R_8$, $R_9$, $R_{10}$, and $R_{11}$ are each hydrogen.

In yet another embodiment of Formula I, $R_1$ and $R_4$ are chosen independently from $C_1$-$C_6$alkyl.

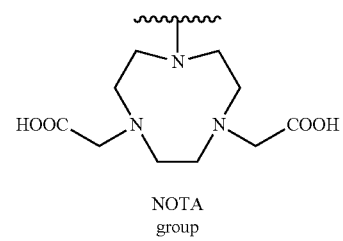

NOTA group

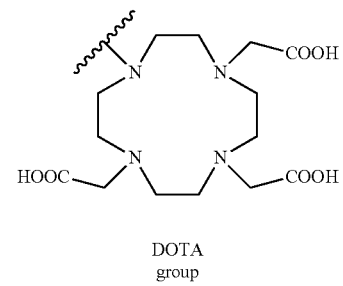

DOTA group

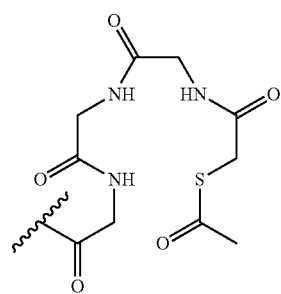

$MAG_3$ group

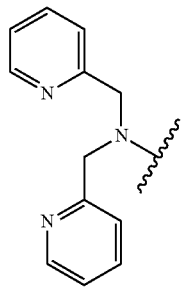

N-methyl-1-(pyridin-2-yl)-N-(pyridin-2-ylmethyl)methanamine "DPA group"

-continued

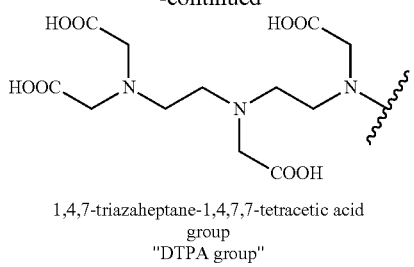

1,4,7-triazaheptane-1,4,7,7-tetracetic acid group
"DTPA group"

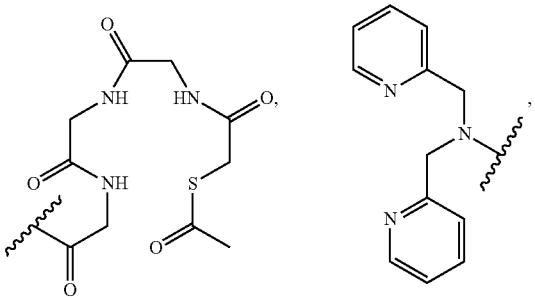

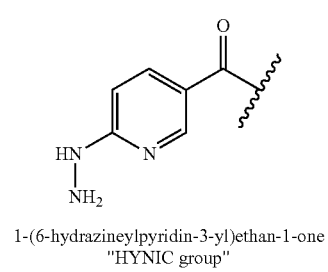

1-(6-hydrazineylpyridin-3-yl)ethan-1-one
"HYNIC group"

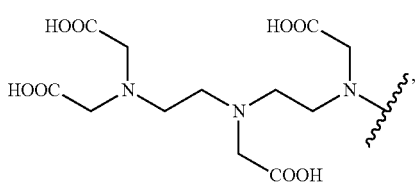

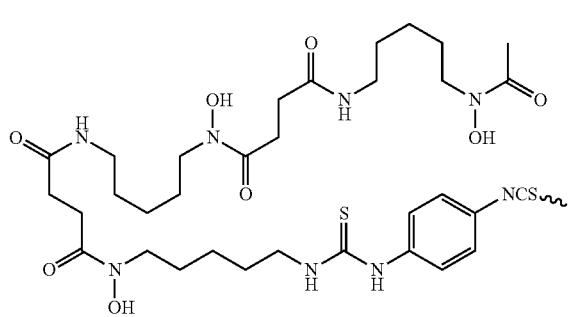

$N^1$-hydroxy-$N^1$-(5-(4-(hydroxy(5-(3-(4-isothiocyanatophenyl)thioureido)pentyl)amino)-4-oxobutanamido)pentyl)-$N^4$-(5-(N-hydroxyacetamido)pentyl)succinamide
"DFO-NCS derivative"

The symbol "⁓" denotes a point of attachment.

In yet another embodiment of Formula I, $R_{13}$ is selected from

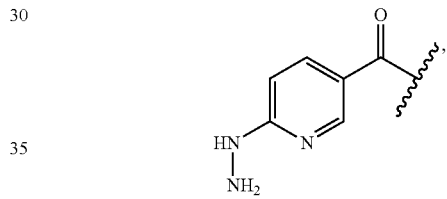

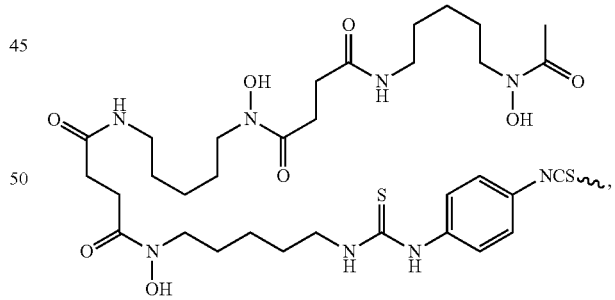

a crown ether, a cyclodextrin, or a porphyrin.

In yet another embodiment of Formula I, $R_{13}$ may be

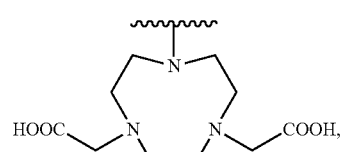

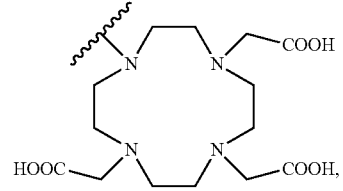

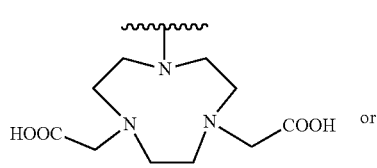 or

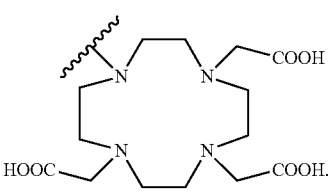

The ligand of $R_{14}$ may be a group derived from a ligand which can treat a disease or a group derived from a ligand which can be used to diagnose a disease. In an embodiment, $R_{14}$ may include

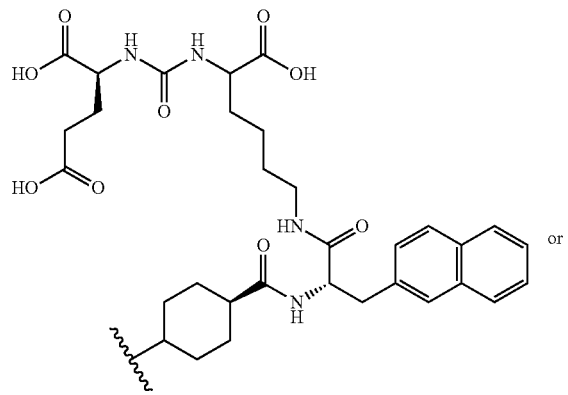

In another embodiment, $R_{14}$ may include

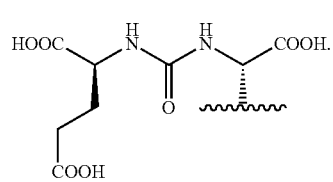

In yet another embodiment, $R_{14}$ may include

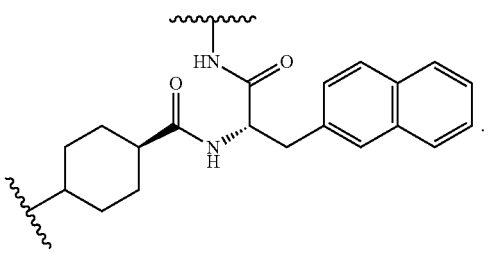

The group designated as $R_{14}$, derived from a ligand, may act to cause a biological effect while still attached as part of Formula I. Alternatively, group designated as $R_{14}$, derived from a ligand may be cleaved from Formula I, for example by an enzyme. The ligand may be a ligand which is capable of binding to a target cell or tissue, for example, the ligand may be capable of binding to a tumor. The binding may be via covalent or non-covalent binding.

In some embodiments, $R_{14}$ may be a group derived from a therapeutic compound. The therapeutic compound may be any compound having therapeutic properties, and may encompass small molecular therapeutic molecules, peptidic drugs, or protein-based therapeutics. For example, in an embodiment, R is selected for its ability to treat or diagnose prostate cancer. It should be understood that $R_{14}$ can be a native therapeutic molecule, or a therapeutically active fragment thereof.

In some embodiments, $R_{14}$ further comprises a radionuclide such as $^{18}F$, $^{76}Br$, $^{124}I$, $^{125}I$, or $^{131}I$. An example of a useful substituent of $R_{14}$ that contains a radionuclide is

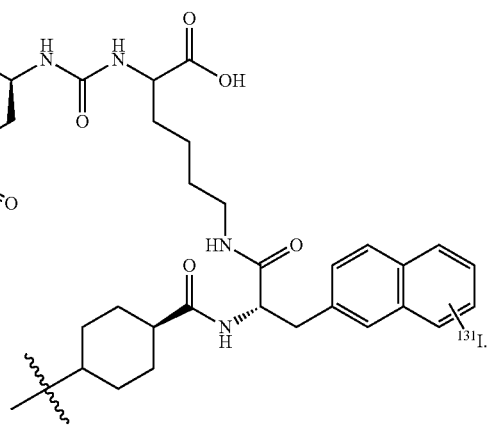

The compound represented by Formula I may be:
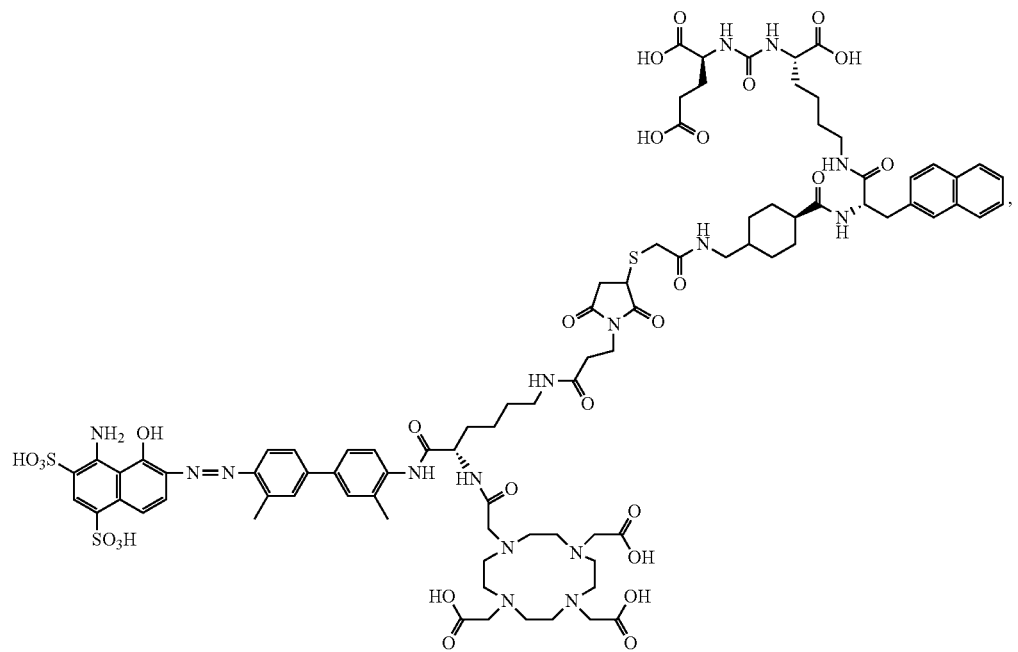
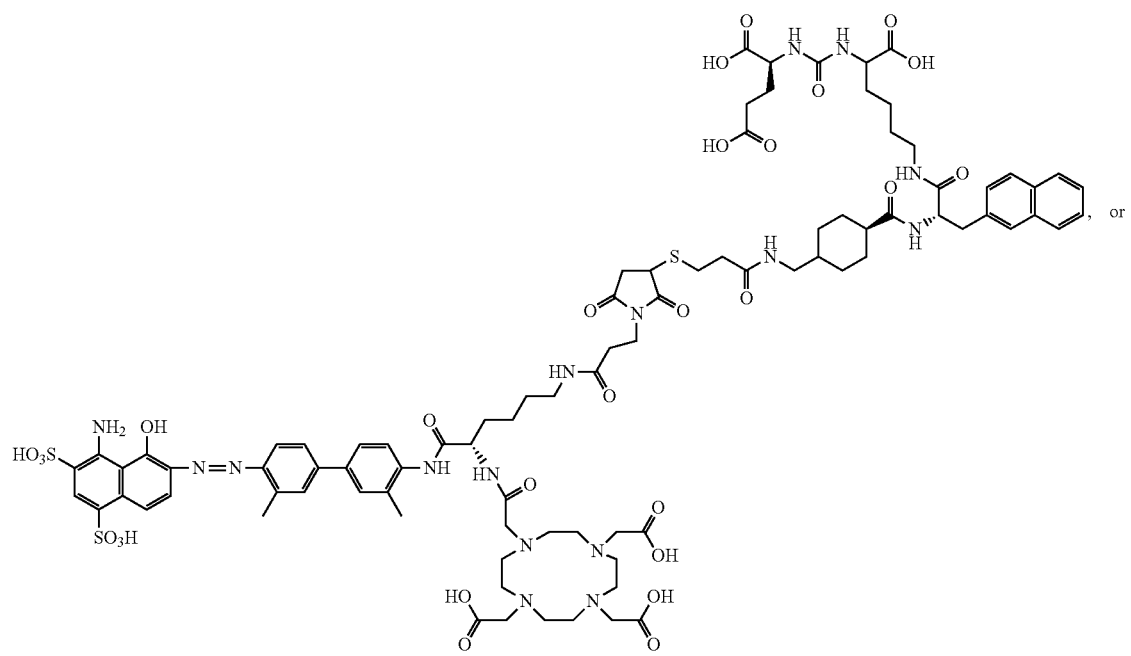

-continued

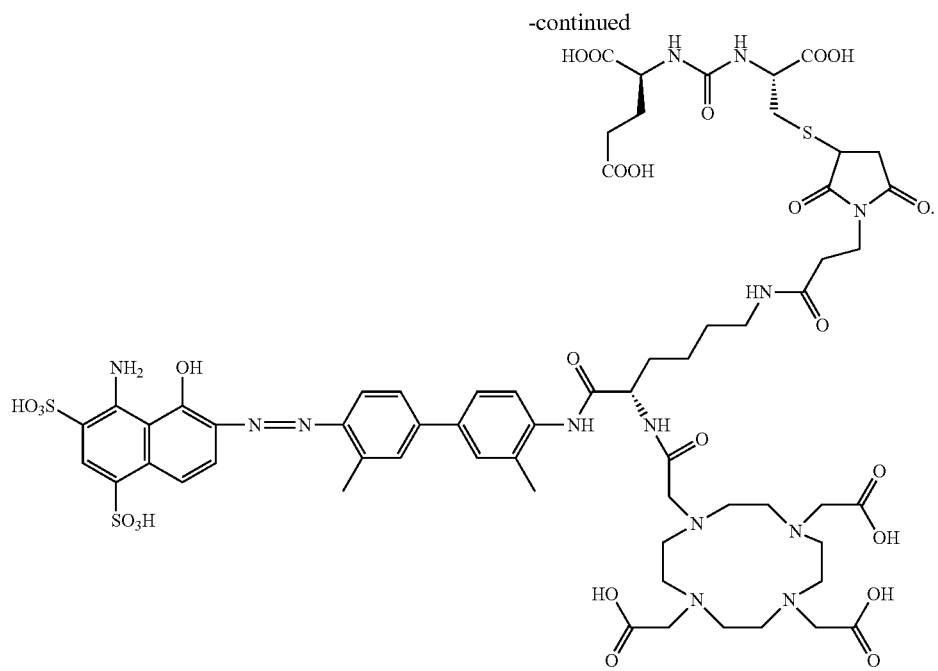

Radionuclide therapy directed against tumors that express prostate-specific membrane antigen (PSMA) has proven effective for treatment of prostate cancer tumors in the clinic. A number of imaging tracers and radiotherapy agents have been recently developed. In human patients, anti-PSMA antibody labeled with $^{177}$Lu, was shown to be effective but had some bone marrow and hematology toxicity possibly due to its long half-life in the blood (days). Several small molecules targeting PSMA were also evaluated in prostate cancer patients labeled with betta emitters such as $^{177}$Lu. The most common one is $^{177}$Lu-PSMA-617 which is under clinical evaluation in many countries. Usual treatment in patients in most clinical trials was composed of up to 3 cycles of $^{177}$Lu-PSMA-617. As stated above, the limited data available suggests partial response rates of up to 70%-80% that was limited to as few as several weeks in some of the patients. Encouragingly, only stage 1-2 hematologic toxicities and sporadically mild xerostomia and fatigue were reported as side effects, and long-term toxicity are yet unknown.

The inventors of the present invention set out to improve the effectiveness of PSMA radiotherapy by preparing a chemical analog that would clear more slowly through the urinary tract and, concomitantly, have increased blood circulation half-life and higher targeted accumulation in the tumors. This goal has been achieved by conjugation of a common, clinically-used ligands containing a residue derived from (((R-)-1-carboxy-2-mercaptoethyl) carbamoyl)-L-glutamic acid to an Evans blue analog (EB), which reversibly binds to circulating serum albumin, to provide a radiopharmaceutical that retained affinity and specificity to PSMA. The proposed modification results in significantly increased blood half-life, increased tumor uptake, and more effective anti-tumor radiotherapy, and may improve therapy of patients with PSMA-positive tumors.

The new designed molecules also retained the high internalization rate of the conjugated target ligand, and therefore, showed significantly higher accumulation in PSMA-positive tumors. Labeling of the novel EB-PSMA derivatives with the therapeutic, pure beta emitter, $^{90}$Y, $^{177}$Lu and other, resulted in improved tumor response and survival rates of mice bearing PSMA xenograft models and had long term efficacy when compared to the ligand itself. This approach may provide a more effective treatment strategy for patients with PSMA-containing tumors.

In some embodiments, the $R_{13}$ group in Formula I further includes a radionuclide such as $^{64}$Cu, $^{67}$Cu, $^{90}$Y, $^{86}$Y, $^{111}$In, $^{186}$Re, $^{188}$Re, $^{89}$Zr, $^{99}$Tc, $^{153}$Sm, $^{213}$Bi, $^{225}$Ac, $^{177}$Lu, $^{223}$Ra, or the like. In some embodiments, the radionuclide included in $R_{13}$ is $^{86}$Y, $^{90}$Y, or $^{177}$Lu. The radionuclide may be bound to $R_{13}$ by chelation, or by other means such as conventional covalent or ionic bonds known in the chemical arts. The radionuclide may be suitable purposes such as imaging or scanning, for example PET imaging, and the compound of Formula I may be a PET imaging agent. The radionuclide may be suitable for purposes of patient treatment, for example radiation treatment, and the compound of Formula I may be an agent for treatment of prostate cancer.

In another aspect, the present invention encompasses chemical conjugates of Evans Blue dye having the compound of Formula II illustrated below, or a pharmaceutically acceptable ester, amide, solvate, or salt thereof, or a salt of such an ester or amide or a solvate of such an ester amide or salt:

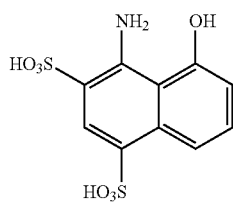
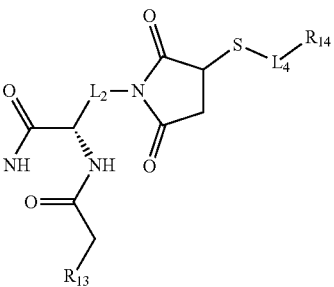

In Formula II, $R_{13}$ is a chelating group and $R_{14}$ is a group capable of binding to prostate-specific membrane antigen (PSMA).

Formula II may also include linking group $L_2$ which is —$(CH_2)_n$— wherein n is an integer from 0 to 12; and linking group $L_4$ which is a $C_1$-$C_{60}$ linking group, optionally including —O—, —S—, —S(O)—, —S(O)$_2$—, —N(R)—, —C(=O)—, —C(=O)O—, —OC(=O)—, —N(R)C(=O)—, —C(=O)N(R)—, —OC(=O)O—, —N(R)C(=O)O—, or —OC(=O)N(R)—, wherein each R is H or $C_1$-$C_6$ alkyl, provided that no two adjacent $CH_2$ groups are replaced.

In some embodiments, the linking groups $L_1$-$L_4$ include polyethylene glycol segments —$CH_2CH_2O$—.

In an embodiment, $L_2$ is —$(CH_2)_4$—NH(CO)—$(CH_2)_2$—; and $L_4$-$R_{14}$ is

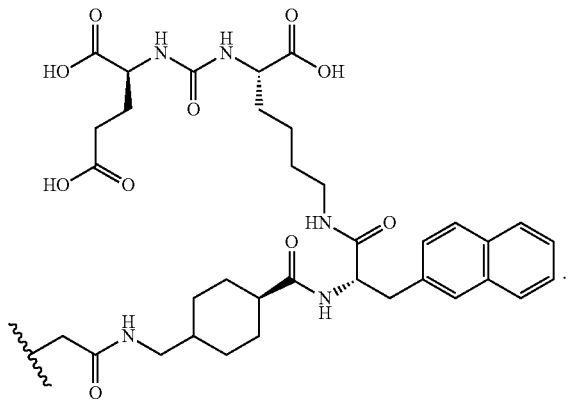

In another embodiment, $L_2$ is —$(CH_2)_4$—NH(CO)—$(CH_2)_2$—; and $L_4$-$R_{14}$ is

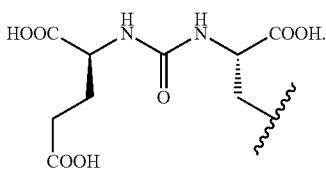 [SMILES: *C[C@H](NC(=O)N[C@@H](CCC(=O)O)C(=O)O)C(=O)O]

The description of embodiments of $R_{14}$ as given for compounds of Formula I also applies to compounds of Formula II. Also, $R_{13}$ and/or $R_{14}$ of Formula II may further include a radionuclide as described above, and the description of radionuclide embodiments as given for compounds of Formula I also applies to compounds of Formula II.

In some embodiments, the novel molecules in the disclosure include the truncated Evans Blue domain as an albumin-binding motif, a chelator for labeling with radionuclide, a spacer, a residue derived from maleimide as a linker, and a biomolecule binding motif.

Pharmaceutical Preparations

Reference to a formula includes references to all subformulae, for example, Formula I includes compounds of Formula II. Compounds disclosed herein can be administered as the neat chemical, but are preferably administered as a pharmaceutical composition. Accordingly, the invention encompasses pharmaceutical compositions comprising a compound or pharmaceutically acceptable salt of a compound, such as a compound of Formula I, together with at least one pharmaceutically acceptable carrier. The pharmaceutical composition may contain a compound or salt of Formula I as the only active agent, but is preferably contains at least one additional active agent. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound, such as a compound of Formula I, and an additional active agent. For example the pharmaceutical composition may contain a molar ratio of about 0.5:1, about 1:1, about 2:1, about 3:1 or from about 1.5:1 to about 4:1 of an additional active agent to a compound of Formula I.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula I and usually at least about 5 wt. % of a compound of Formula I. Some embodiments contain from about 25 wt % to about 50 wt % or from about 5 wt % to about 75 wt % of the compound of Formula I.

Treatment Methods

The compounds of Formula I, as well as pharmaceutical compositions comprising the compounds, are useful for diagnosis or treatment of diseases such as cancer. According to the present invention, a method of treating prostate cancer comprises providing to a patient in need of such treatment a therapeutically effective amount of a compound of Formula I. In an embodiment, the patient is a mammal, and more specifically a human. As will be understood by one skilled in the art, the invention also encompasses methods of treating non-human patients such as companion animals, e.g., cats, dogs, and livestock animals.

A therapeutically effective amount of a pharmaceutical composition is preferably an amount sufficient to reduce or ameliorate the symptoms of a disease or condition. In the case of prostate cancer, for example, a therapeutically effective amount may be an amount sufficient to reduce or ameliorate high blood sugar. A therapeutically effective amount of a compound or pharmaceutical composition described herein will also provide a sufficient concentration of a compound of Formula I when administered to a patient. A sufficient concentration is preferably a concentration of the compound in the patient's body necessary to prevent or combat the disorder. Such an amount may be ascertained experimentally, for example by assaying blood concentration of the compound, or theoretically, by calculating bioavailability.

According to the invention, the methods of treatment disclosed herein include providing certain dosage amounts of a compound of Formula I to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A compound of Formula I may be administered singularly (i.e., sole therapeutic agent of a regime) to treat or prevent diseases and conditions such as prostate cancer, or may be administered in combination with another active agent. One or more compounds of Formula I may be administered in coordination with a regime of one or more other active agents such as anticancer cytotoxic agents. In an embodiment, a method of treating or diagnosing prostate cancer in a mammal includes administering to said mammal a therapeutically effective amount of a compound of Formula I, optionally in combination with one or more additional active ingredients.

As will be appreciated by one skilled in the art, the methods of treatment provided herein are also useful for treatment of mammals other than humans, including for veterinary applications such as to treat horses and livestock, e.g., cattle, sheep, cows, goats, swine and the like, and pets (companion animals) such as dogs and cats.

For diagnostic or research applications, a wide variety of mammals will be suitable subjects including rodents (e.g., mice, rats, hamsters), rabbits, primates, and swine such as inbred pigs and the like. Additionally, for in vitro applications, such as in vitro diagnostic and research applications, body fluids (e.g., blood, plasma, serum, cellular interstitial fluid, saliva, feces, and urine) and cell and tissue samples of the above subjects will be suitable for use.

In an embodiment, the invention provides a method of treating prostate cancer in a patient identified as in need of such treatment, the method comprising providing to the patient an effective amount of a compound of Formula I. The compounds of Formula I provided herein may be administered alone, or in combination with one or more other active agents.

In another embodiment, the method of treating prostate cancer may additionally comprise administering the compound of Formula I in combination with one or more additional compounds, wherein at least one of the additional compounds is an active agent, to a patient in need of such treatment. The one or more additional compounds may include additional therapeutic compounds, including anticancer therapeutic compounds such as doxorubicin, paclitaxel, docetaxel, cisplatin, camptothecin, temozolomide, avastin, Herceptin, Erbitux, and the like.

The compositions of the present invention offer the advantage that many small molecules and biologics can be easily modified in one step with high yield and high purity. Due to the relatively strong binding of EB moiety with albumin, the in vivo biodistribution can be easily controlled to adjust the number of EB moieties and linkers. In addition, the relative small size of the EB moiety reduces the likelihood of any interference with the biological function of the small molecule or biologic. The addition of a chelator, such as NOTA or DOTA linked to the EB moiety allows for facile addition of further groups such as radionuclides, which can allow the present molecules to act as imaging agents and/or radiotherapeutic agents. The present invention therefore provides an efficient system for developing long lasting and long acting therapeutic and imaging agents with high efficacy.

EXAMPLES

The present invention is further described in detail by means of the following Examples. All parts and percentages are by weight and all temperatures are degrees Celsius unless explicitly stated otherwise.

Abbreviations

Boc tert-butoxycarbonyl
DIPEA diisopropylethylamine
DMF N,N-Dimethylformamide
DOTA 1,4,7,10-tetraazacyclododecane-1,4,7,10-tetraacetic acid
Fmoc fluorenylmethyloxycarbonyl chloride
HATU 1-[Bis (dimethylamino) methylene]-1H-1,2,3-triazolo[4,5-b]pyridinium 3-oxid hexafluorophosphate
HPLC High Performance Liquid Chromatography
LC-MS Liquid Chromatography/Mass Spectrometry
PET Positron Emission Tomography
RT Room Temperature
TFA Trifluoroacetic Acid

General Methods

Boc-Lysine-Fmoc amino acid was purchased from AppTech. DOTA-NHS ester) was purchased from Macrocyclics. All other solvents and chemicals were purchased from Sigma-Aldrich or Fisher Scientific.

Chemical purities were determined on analytical high performance liquid chromatography (HPLC) using a Phenomenex Luna C18 column (5 μm, 4.60×150 mm) with two gradient systems; system 1-gradient starting from 95% of solvent A 0.1% TFA in H$_2$O and 5% of solvent B (CH$_3$CN) for 5 min and increasing to 65% of solvent B in 30 min and then to 90% in 5 min at flow rate of 1 mL/min. System 2-Same gradient as system 1 using solvent A (50 mM NH$_4$OAc) and solvent B (CH$_3$CN). The ultraviolet (uv) absorbance was monitored at 254 and 600 nm. Compounds were purified on Biotage system (C-18, SNAP 120 g) using gradient system of 95% solvent A (0.1% TFA in H$_2$O) and 5% of solvent B (CH$_3$CN) for 5 min and increasing to 65% of solvent B in 66 min at flow rate of 40 mL/min.

LC-MS analysis was done similar to the reported procedure (1). $^{86}$YCl$_3$ was acquired from NIH cyclotron facility. $^{90}$YCl$_3$ was purchased from Perkin-Elmer. $^{177}$LuCl$_3$ was purchased from University of Missouri Research Reactor (MURR).

Example 1: Synthesis of Dota-Maleimide-Eb (Dmeb)

Steps 1-2: Synthesis of Tolidine-Lys-Boc

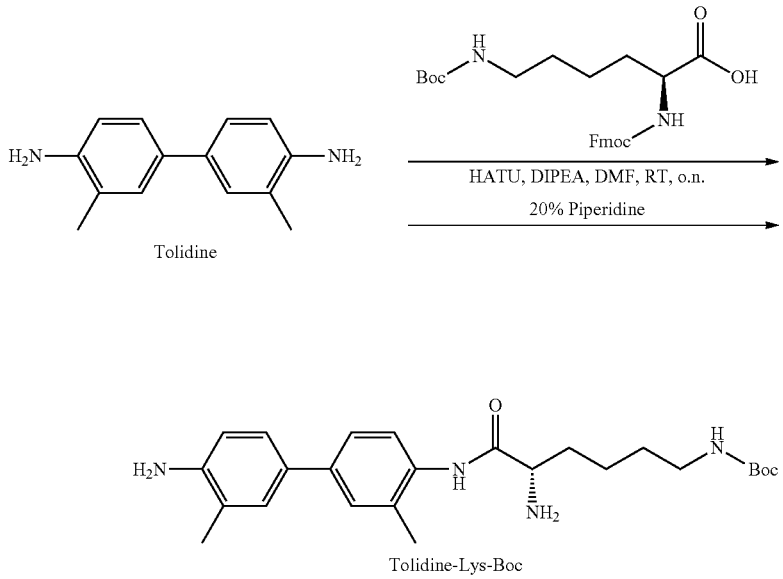

To a 100 mL round flask containing 1.1 g of Boc-Lysine-Fmoc amino acid (1 eq) and anhydrous N,N-dimethylformamide (DMF) (10 mL) was added HATU (0.94 g, 1.05 eq) under Argon. The mixture was stirred for 10-15 min at room temperature (RT). Then diisopropylethylamine (DIPEA) (4 mL, 10 eq) was added followed by addition of tolidine (0.75 g, 1.5 eq) in 10 mL DMF. The reaction mixture was stirred over-night. Conversion to the desired product was evaluated by analytical HPLC, using system 1 (retention time of 32.3 min). The solvents were removed by rotary evaporator using an oil vacuum pump. The remaining oil was re-dissolved in 5-10 mL DMF and then 20% of piperidine (v/v) were added. The mixture was stirred for 15-20 at RT and de-protection of the Fmoc was evaluated by injection to analytical HPLC system 1 (retention time of 18.7 min). The crude mixture was purified on Biotage system using the gradient system describe above and the collected pure desired fractions were lyophilized. Chemical purity of the desired Tolidine-Lys-Boc was above 95% with yield ranging from 68-72% of white powder. LC-MS: [MH]$^-$=439.18 (m/z), calc: 440.2.

Step 3: Synthesis of Dota-Tolidine-Lys-Boc

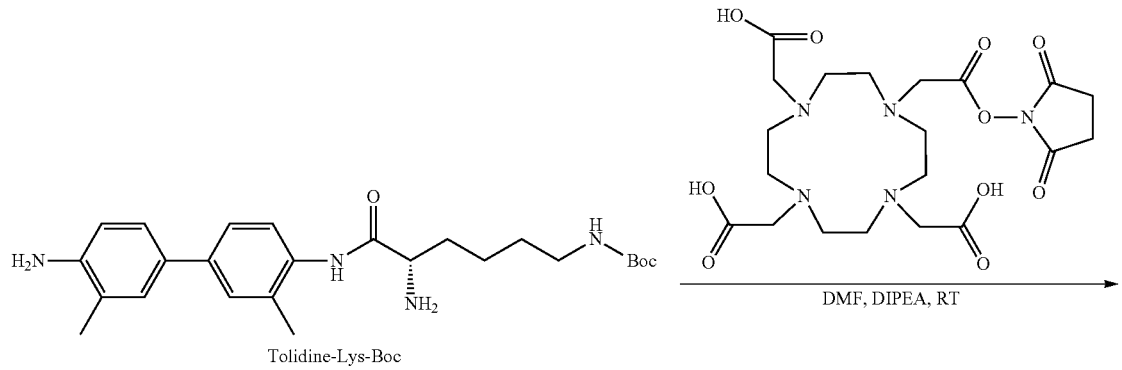

Tolidine-Lys-Boc

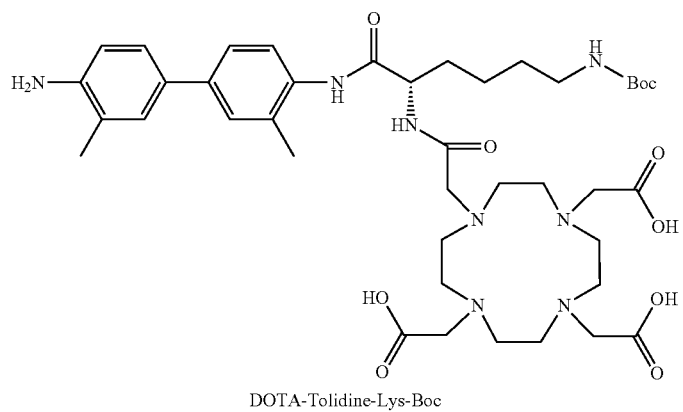

DOTA-Tolidine-Lys-Boc

Tolidine-Lys-Boc (0.52 g, 1 eq) was dissolved in 5 mL DMF. Then DOTA-NHS ester (1 g, 1.1 eq) in 2-3 mL DMF were added followed by addition of DIPEA (1 mL, 5 eq). The mixture was stirred for 2-3 h at RT. Conversion to the desired product was evaluated on analytical HPLC system 1 (retention time of 18.1 min). Purification was done on Biotage system and the collected pure desired fractions were lyophilized to give 76% yield of white powder with a chemical purity greater than 95%. LC-MS: $[MH]^-$=825.5 (m/z), calc: 826.4.

Step 4: Synthesis of Dota-Tolidine-Lys

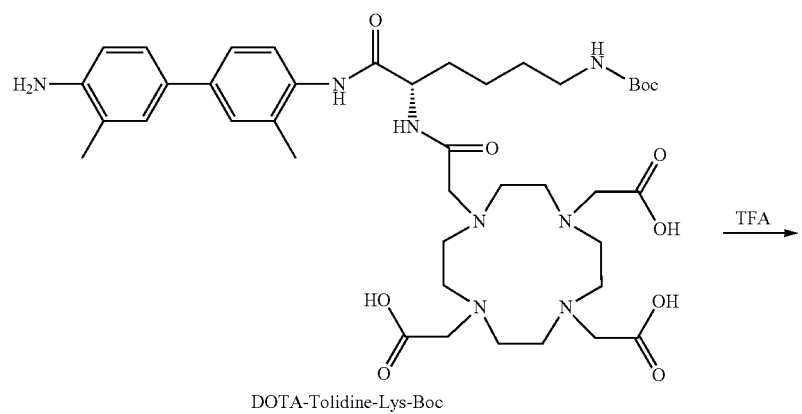

DOTA-Tolidine-Lys-Boc

-continued

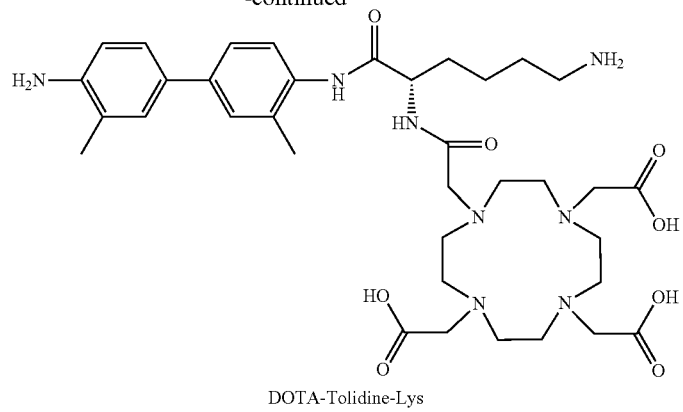
DOTA-Tolidine-Lys 5 mL of neat TFA were added to DOTA-Tol-Lys-Boc. The mixture was incubated at RT for 15-20 min. Then TFA was evaporated to dryness and water were added. Analytical HPLC system 1 confirmed the deprotection of Boc (retention time of 10.4 min). The mixture with the water was lyophilized to give pure desired product with a chemical yield greater than 80%. LC-MS: [MH]=725.2 (m/z), calc: 726.4.

Step 5: Synthesis of Dota-Tolidine-Lys-Maleimide

DOTA-Tolidine-Lys-Boc (0.57 g, 1 eq) was dissolved in 5 mL of dimethyl sulfoxide (DMSO). Then 3-(maleimido) propionic acid N-hydroxysuccinimide ester (0.23 g, 1.1 eq) in 3 mL DMSO were added, followed by addition of triethylamine ($Et_3N$, 0.56 mL, 5 eq). The mixture was stirred at RT for 2 h. Analytical HPLC confirmed full conversion to the desired product (retention time of 14.0 min). Purification was done on Biotage system and the collected pure desired fractions were lyophilized to give 76% yield of white

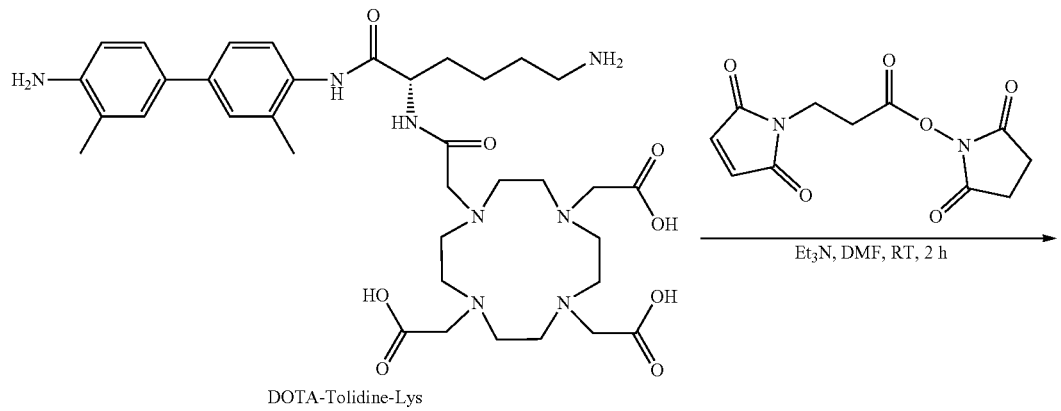
DOTA-Tolidine-Lys $Et_3N$, DMF, RT, 2 h

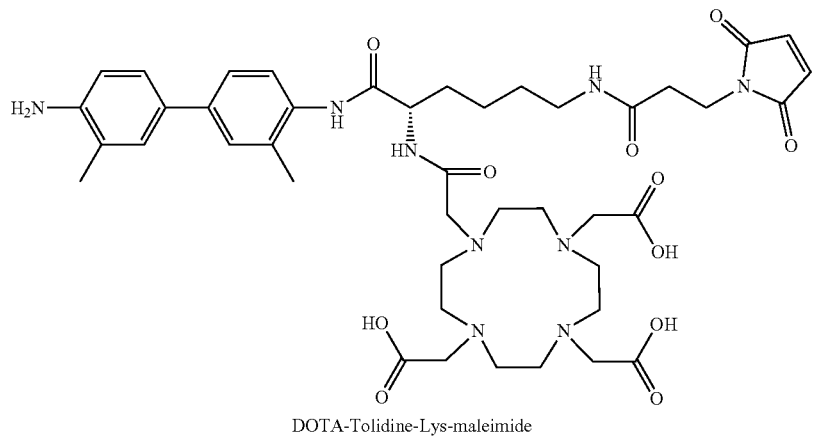
DOTA-Tolidine-Lys-maleimide powder with a chemical purity greater than 95%. LC-MS: [MH]⁻=876.4 (m/z), calc: 877.4.

Step 5: Synthesis of Dota-Maleimide-Eb (Dmeb)

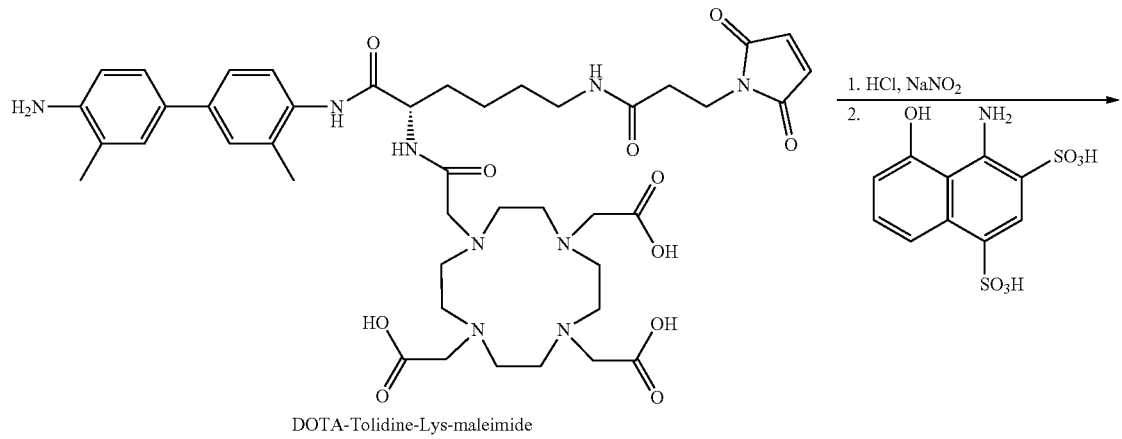

DOTA-Tolidine-Lys-maleimide

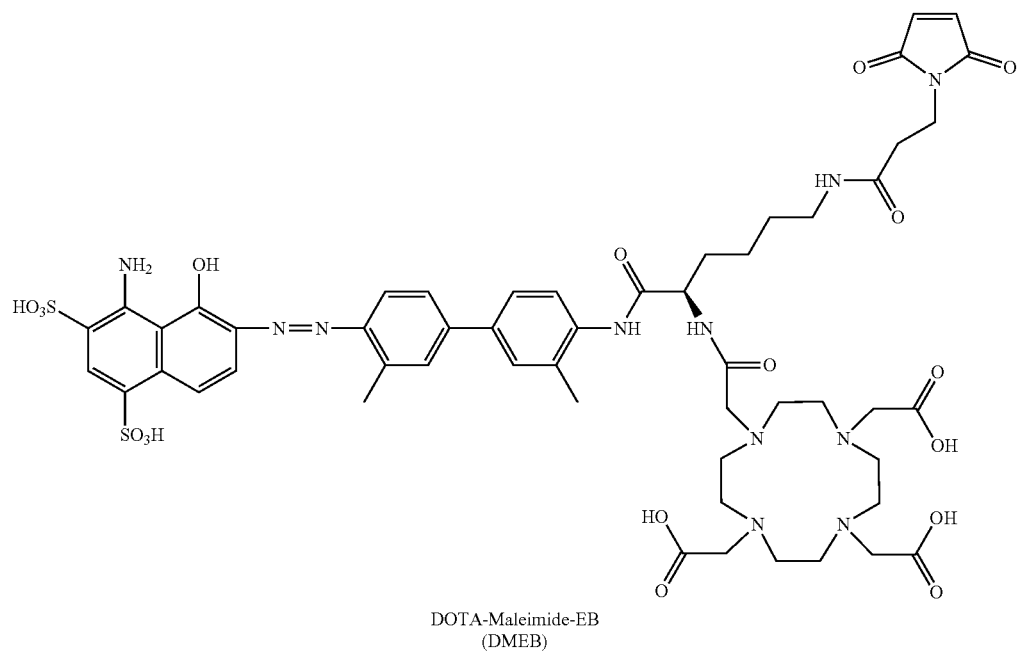

DOTA-Maleimide-EB
(DMEB)

DOTA-Tolidine-Lys-maleimide (0.5 g) was dissolved in 1 mL CH₃CN and 1 mL of H₂O in a glass vial. Then 3 eq (0.062 g, 0.054 mL) of 30% HCl were added in 1 mL of H₂O. The solution was cooled in an ice bath and after few minutes, cold NaNO₂ solution in 1 mL H₂O (3 eq, 0.12 g) was added. The crude mixture was stirred in ice for 30 min. The solution turned yellow which indicates the formation of diazonium salt.

The above diazonium salt solution was added by small portions, to a glass vial containing 1-amino-8-naphtol-2,4-disulfonic acid monosodium salt (1 eq, 0.2 g) and sodium bicarbonate (4-5 eq, 0.2 g) in 1 mL H₂O. The mixture was stirred for additional hour in ice and formation of DMEB was analyzed by analytical HPLC system 2 (retention time of 16.8 min). Purification was done on Biotage system and the collected pure desired fractions were lyophilized to give 60% yield of white powder with a chemical purity greater than 90%. LC-MS: [MH]⁻=1206.2 (m/z), calc: 1207.7.

Example 2: Alternative Synthesis of Dota-Maleimide-Eb (Dmeb)

Step 1: Preparation of Evans Blue Amine (Eb-Nh₂)

To a 100 ml round bottom flask containing 2-tolidine (4.3 g) and methylene chloride (40 ml) was added di-t-butyldicarbonate (4.4 g). The mixture was stirred at room temperature overnight. The reaction was concentrated and the residue was purified by chromatography on silica gel to give 3.2 g of N-Boc-2-tolidine. LC-MS: [MH]⁺=313.4135 (m/z), calc: 312.1838.

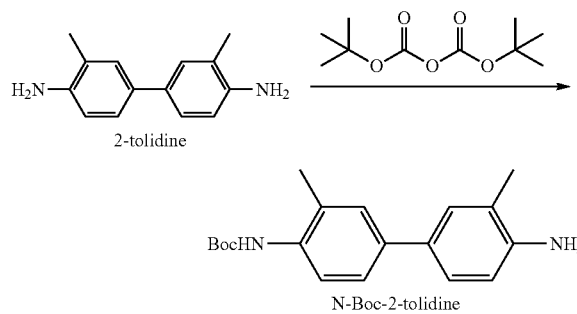

N-Boc-2-tolidine (0.46 g, 1.47 mmol) was dissolved in acetonitrile (10 ml) in a glass vial, was cooled to 0° C., then hydrochloric acid (0.3 M, 15 ml) was added. Cold sodium nitrite solution (0.31 g in 5 ml water) was added dropwise and stirred for 20 min, and the solution turned bright yellow. This solution was added dropwise to another glass vial containing 1-amino-8-naphthol-2,4-disulfonic acid monosodium salt (0.59 g) and sodium bicarbonate (0.49 g) in water (20 ml) at 0° C. The reaction was deemed complete by LC/MS and the reaction was lyophilized without further purification to provide the Boc-EB product. [M-H]⁻=541.4425, calc: 542.0930.

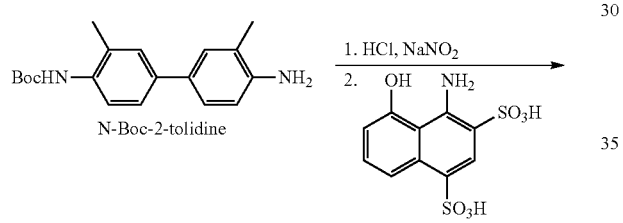

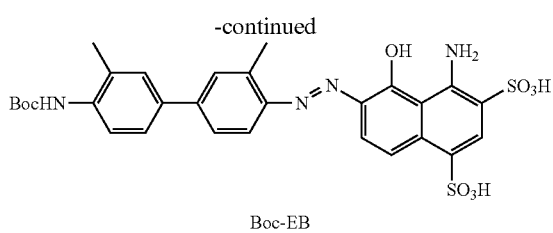

The Boc EB product was added to a solution of 80% TFA, 10% 1,2-ethanedithiol and 10% thioanisole and stirred until reaction was complete. The mixture was diluted with water (100 ml) and loaded on a C-18 chromatography cartridge (3×15 cm). The column was washed with water and then with 80% ethanol to elute the desired product. After evaporation of the solvent in the eluent, 0.6 g of 80% pure product EB-NH$_2$ was obtained. A small amount of product was further purified by HPLC. LC-MS: [M-H]⁻=541.4425, calc: 542.0930.

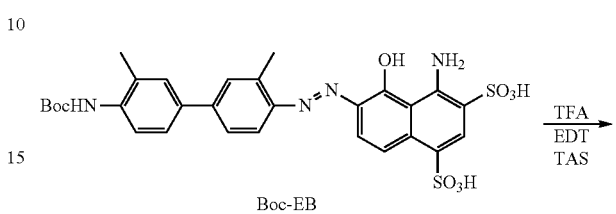

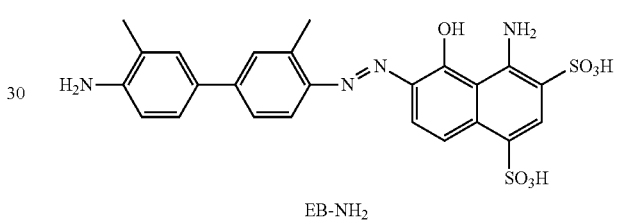

Step 2: Synthesis of Eb-Lys-Boc

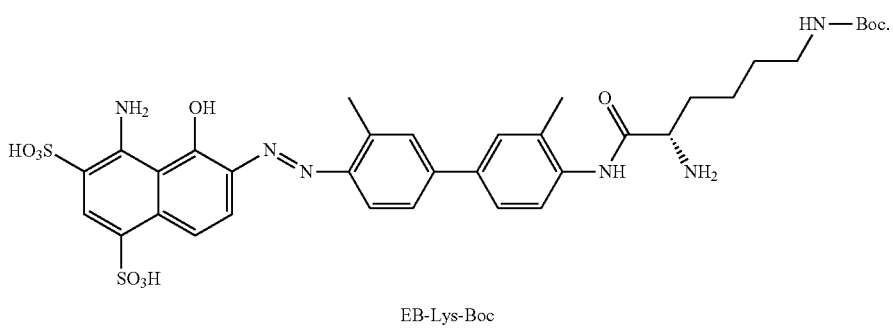 [SMILES: Cc1cc(-c2ccc(NC(=O)[C@@H](N)CCCCNC(=O)OC(C)(C)C)c(C)c2)ccc1/N=N/c1ccc2c(S(=O)(=O)O)cc(S(=O)(=O)O)c(N)c2c1O]

To a solution of Boc-Lys-Fmoc amino acid (3.6 eq) in anhydrous N,N-dimethylformamide (DMF) (2-3 mL) were added (1-[Bis (dimethylamino) methylene]-1H-1,2,3-triazolo[4,5-b]pyridinium 3-oxid hexafluorophosphate) (HATU, 4.2 eq) under Argon. The solution was stirred for 10 min at room temperature (RT). Then 10 eq of diisopropylethylamine (DIPEA) were added followed by addition of EB-NH$_2$ in 5-7 mL DMF. The reaction was stirred overnight at RT. Conversion of the EB-NH$_2$ to EB-conjugated to protected Fmoc-Lys-Boc was monitored using analytical HPLC system 1. Retention time of EB-NH$_2$ was 7.7 min and conjugated EB-protected Lys was 11 min. After conversion completion, 20% of piperidine (v/v) were added and the reaction was stirred for an additional hour. DMF was removed by high vacuum oil pump and the reaction was re-dissolved in methanol/H₂O (2:1) and purified on Biotage system. The collected HPLC fractions were re-injected onto an analytical HPLC to determine purity greater than 90% and were further lyophilized. EB-Lys-Boc retention time (r.t.) was 8.3 min (system 1) or 23.2 min (system 2). LC-MS analysis confirmed mass of 769 [MH]⁻.

Step 3: Synthesis of Dota-Eb-Lys-Boc

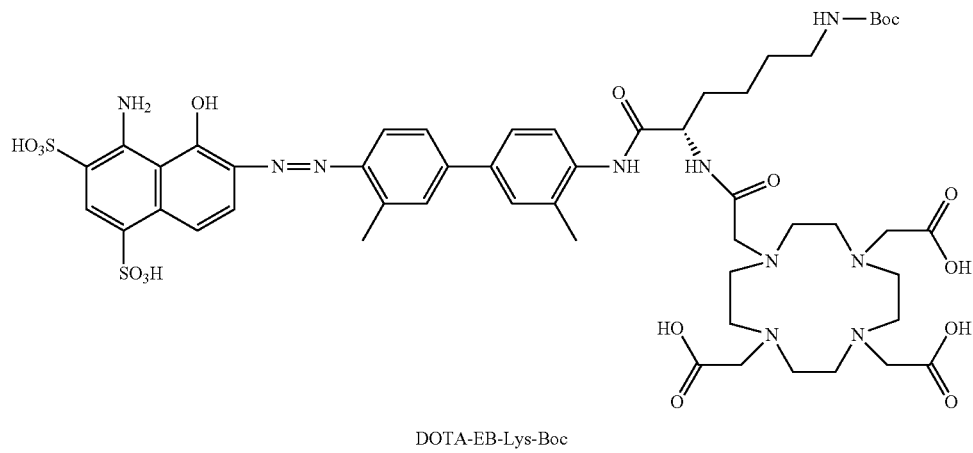 [SMILES: Cc1cc(-c2ccc(NC(=O)[C@H](CCCCNC(=O)OC(C)(C)C)NC(=O)CN3CCN(CC(=O)O)CCN(CC(=O)O)CCN(CC(=O)O)CC3)c(C)c2)ccc1N=Nc1ccc2c(S(=O)(=O)O)cc(S(=O)(=O)O)c(N)c2c1O]

DOTA-EB-Lys-Boc

Reaction between EB-Lys-Boc and DOTA-bis (t-Bu ester) was done similar to the conditions described above. Analytical HPLC system 2 confirmed purity >90% with a r.t. of 29.3 min and mass of 1167 [MH]⁻.

Step 4: Synthesis of Dota-Eb-Lys

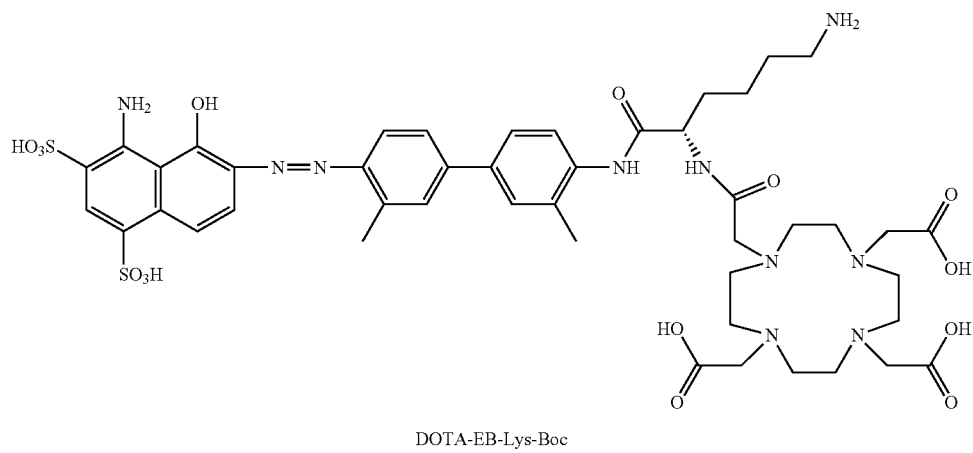 [SMILES: Cc1cc(-c2ccc(NC(=O)[C@H](CCCCN)NC(=O)CN3CCN(CC(=O)O)CCN(CC(=O)O)CCN(CC(=O)O)CC3)c(C)c2)ccc1N=Nc1ccc2c(S(=O)(=O)O)cc(S(=O)(=O)O)c(N)c2c1O]

DOTA-EB-Lys-Boc

Deprotection was done at RT using thioanisole: 1,2-ethanedithiol: anisole: TFA (5:3:2:90). Completion of deprotection was monitored by HPLC (r.t. of 17.1 min). TFA was removed by Argon flow before purification. DOTA-EB-Lys was purified on Biotage system. LC-MS analysis confirmed mass of 954 [MH]⁻.

Step 5: Synthesis of Dota-Maleimide-Eb (Dmeb)

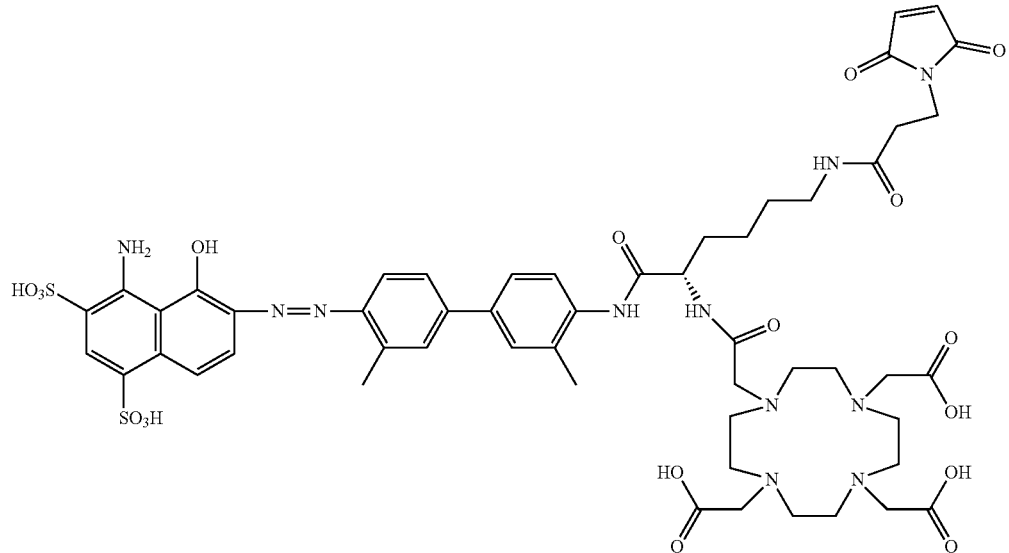 [SMILES: Cc1cc(-c2ccc(NC(=O)[C@H](CCCCNC(=O)CCN3C(=O)C=CC3=O)NC(=O)CN3CCN(CC(=O)O)CCN(CC(=O)O)CCN(CC(=O)O)CC3)c(C)c2)ccc1N=Nc1ccc2c(S(=O)(=O)O)cc(S(=O)(=O)O)c(N)c2c1O]

DOTA-EB-Lys was dissolved in 0.5 mL DMF. Then 1.26 eq of trimethylamine were added, followed by 1.26 eq of 3-(Maleimido) propionic acid N-hydroxysuccinimide ester in 0.2 mL DMF. The reaction was stirred for 2 h at RT. Purification was done on Higgins column. Analytical HPLC injection (system 2) showed purity >90% with a r.t. of 17.4 min and mass of 1105 [MH]$^-$.

Example 3: Synthesis of Psma-617-Sh

The t-Bu-PSMA-617-amine was purchased from CS Bio Inc. SATA (N-succinimidyl S-acetylthioacetate) was purchased from ThermoFisher Scientific. PSMA-617 was synthesized in three steps as follow.

Step 1: Synthesis of Psma-617-S-Acetyl

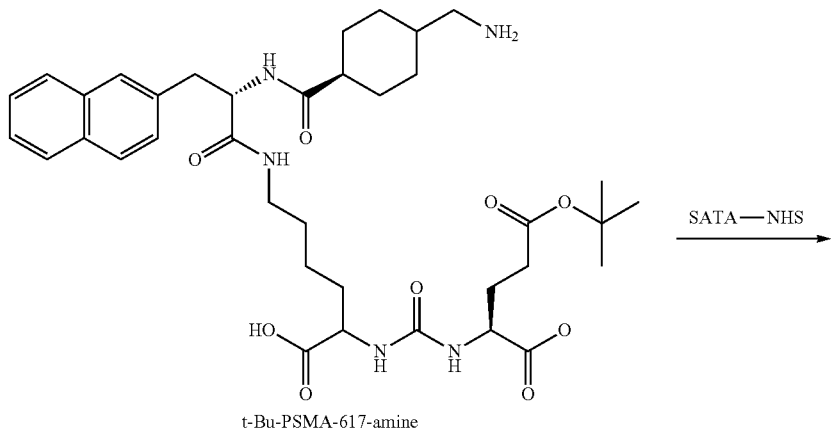

t-Bu-PSMA-617-amine

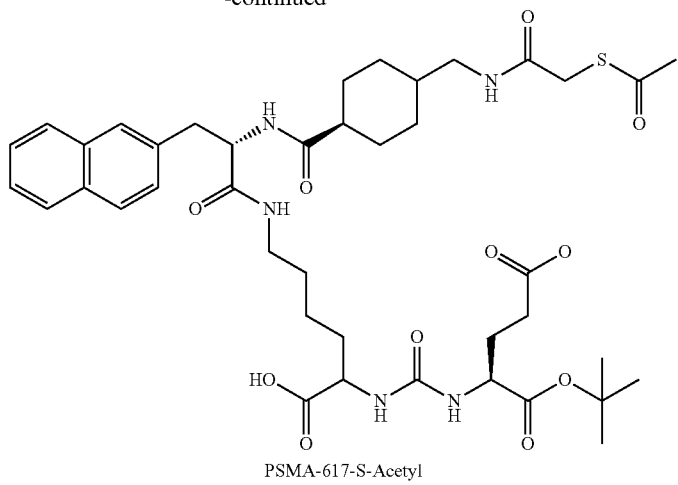
PSMA-617-S-Acetyl
t-Bu-PSMA-617-amine (65 mg, 1 eq) was dissolved in 1 mL of anhydrous DMSO. Then 1.1 eq (21 mg) of SATA in 0.4 mL DMSO was added, followed by addition of DIPEA, 5 eq (0.074 mL). The mixture was stirred at RT for 2-3 h and purified on Higgins column (C-18, 5 μm, 250×20 mm) using gradient system 1 and flow rate of 12 mL/min. The collected fractions were lyophilized. LC-MS: $[MH]^-=882.5$ (m/z), calc: 883.4.
Steps 2-3: Synthesis of Psma-617-Sh
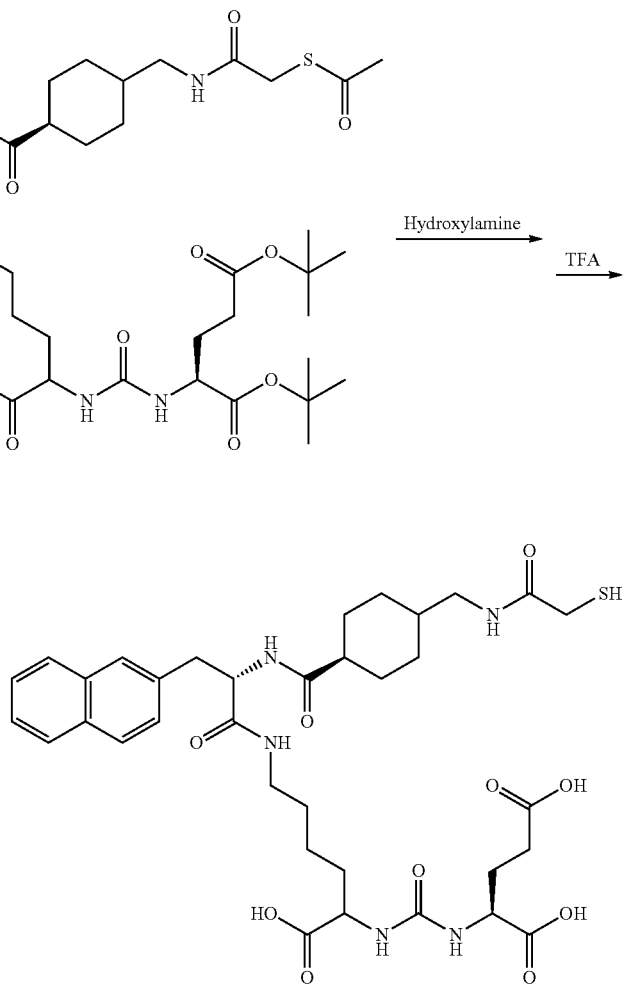

PSMA-S-Acetyl was deprotected using neat TFA for 10-20 min at RT. After deprotection was confirmed by analytical HPLC system 1, the TFA was evaporated to dryness. Then 70 mg of Hydroxylamine (HCl salt) and 20 mg of EDTA were added in 3 ml of borate buffer pH 9.4. The final pH of the mixture was around 6 as determined by pH paper. The mixture was stirred at RT for 1 h and purified on Higgins column as described above. The collected fractions were lyophilized. LC-MS: [MH]⁻=728.24 (m/z), calc: 729.3.

Example 4: Synthesis of Mcg-Sh

MCG-SH was prepared according to a procedure described in Banerjee S. R. et al. "Synthesis and Evaluation of Techmetium-99m- and Rhenium-Labeled Inhibitors of the Prostate-Specific Membrane Antigen (PSMA), J. Med. Chem. 2008, 51 (15), 4504-4517.

Example 5a: Synthesis of Dota-Maleimide-Eb-Psma-617

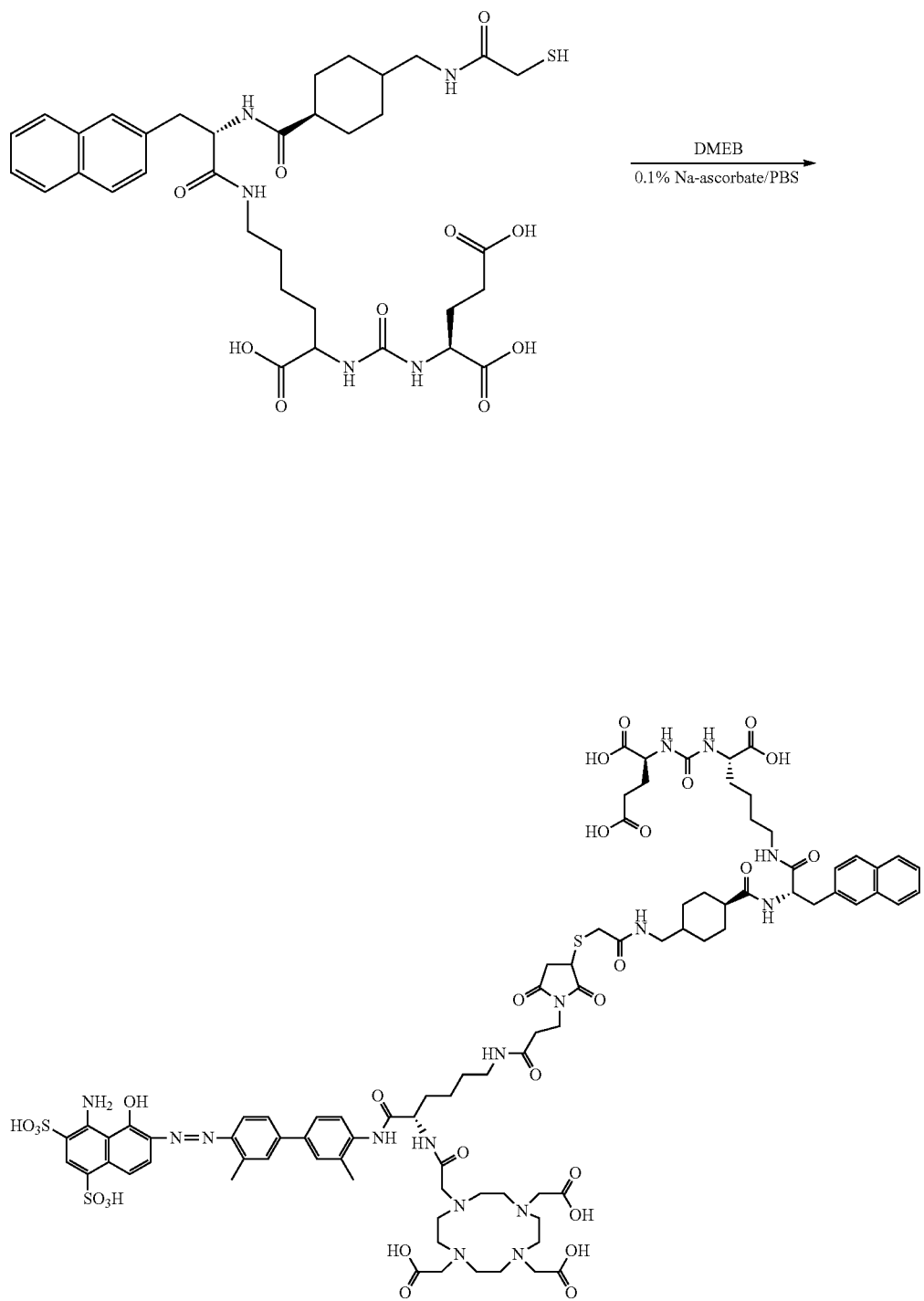

DOTA-maleimide-EB (DMEB, 23 mg, 1 eq) was dissolved in 2 mL degassed solution of 0.1% Na-ascorbate in PBS (w/v). PSMA-617-SH (14.6 mg, 1.05 eq) in 0.1 mL of DMSO was added. The solution was stirred at RT for 1-2 h and purified on Higgins column. The collected fractions were lyophilized to give 37 mg of EB-PSMA-617 with a chemical purity >95%. LC-MS: [MH]⁻=1936.3 (m/z), 967.6 (m/2).

Example 5B: Synthesis of Dota-Maleimide-Eb-Psma-617 Homologue

DOTA-maleimide-EB-PSMA-617 homologue was prepared by treatment of PSMA-617 homologue with DOTA-maleimide-EB in the presence of a solution of 0.1% Na-ascorbate in PBS, as described in Example 5A above.

PSMA-617 homologue was prepared by a reaction of t-Bu-PSMA-617-amine with 3-(tritylthio) propionic acid under conditions described in Step 1 of Example 3, followed by a solvolysis of the resulting trityl derivative with trifluoroacetic acid (TFA).

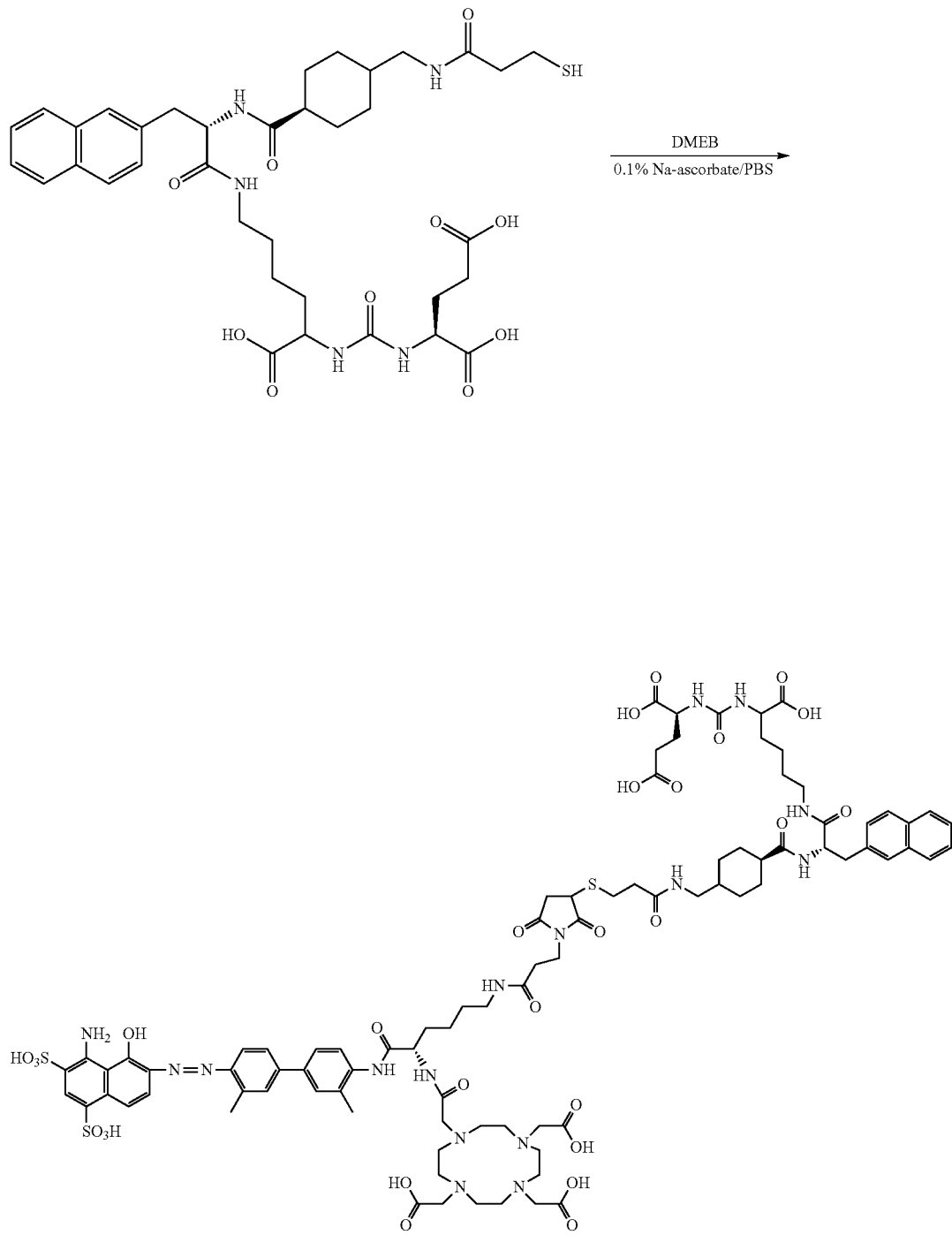

Example 6: Synthesis of Dota-Mcg
EB-MCG was synthesized by using MCG-SH from JHU and DOTA-maleimide. LC-MS: [MH]$^-$=1501.5 (m/z), 749.5 (m/2).
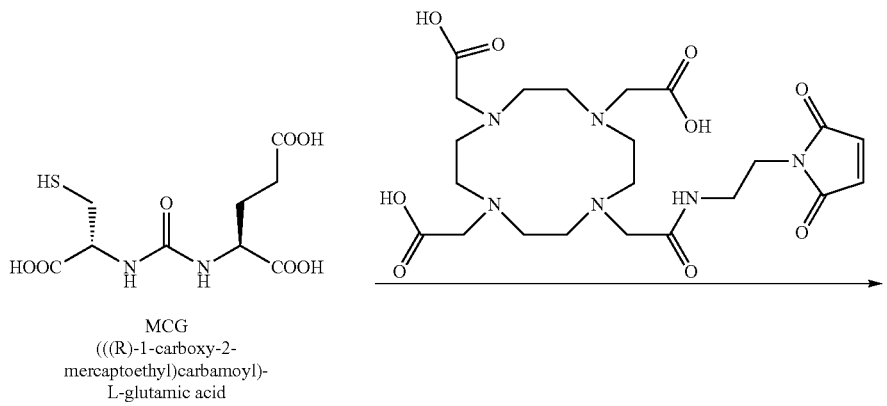
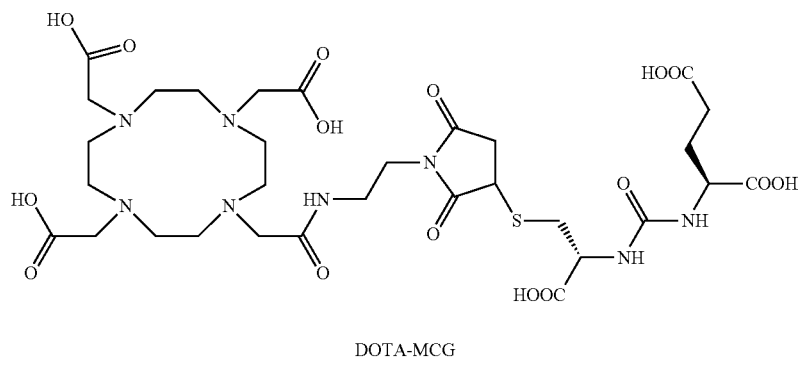
DOTA-MCG
Example 7: Synthesis of Eb-Mcg
EB-MCG was synthesized in the same manner as described above for EB-PSMA-617, using MCG-SH from JHU. LC-MS: [MH]$^-$=1501.5 (m/z), 749.5 (m/2).
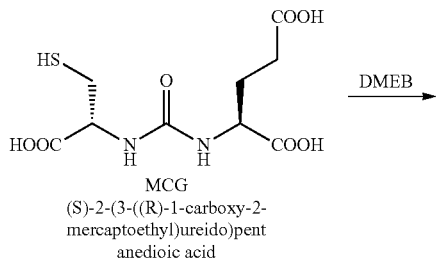

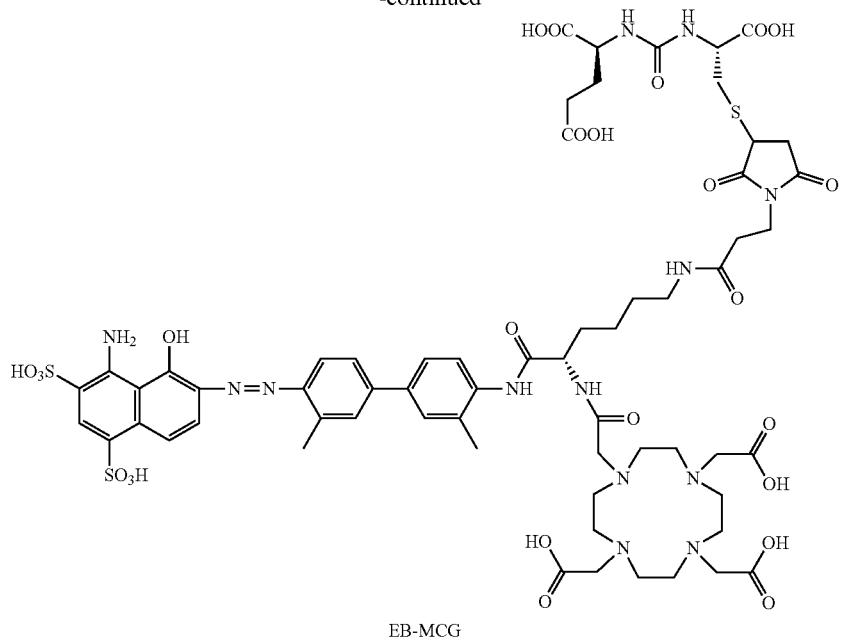

EB-MCG

Example 8: Labeling of Compounds 4-10 μL of either $^{86}YCl_3$, $^{90}YCl3$ or $^{177}LuCl_3$ were diluted with 0.5 mL 0.4 M ammonium acetate pH 5.6. Then 0.1 mg of the selected ligand (EB-PSMA-617, EB-MCG, DOTA-PSMA-617 or DOTA-MCG) was added and the reaction mixed for 30 min at 80° C. Purity of the products was assayed by radio-TLC (AR-2000 Bioscan scanner), using iTLC plates (Fisher) and 0.1 M Citric acid pH 5 as the developing solvent. $R_f$ of free radioisotope ~0.9; $R_f$ of the desired labeled ligand was ~0.1.

Example 9: Cell Culture

PSMA⁺PC3 PIP cells (human metastatic [bone] prostate carcinoma-provided to us by Dr. Martin Pomer, JHU) engineered to express high PSMA levels, and PSMA-PC3 (low PSMA levels) cells were cultured in RPMI 1640 medium supplemented with 10% FBS and Penicillin/Streptomycin (100 U/mL/100 μg/mL) at 37° C. in 5% CO2 in air.

Example 10: Cell Uptake and Internalization of $^{86}$Y-Eb-Psma-617

Twenty-four hours before the assay, $10^5$ PC3-PIP cells/well were distributed into 24-wells plate. Cells were washed with PBS X2 and then 18.5 KBq/well of $^{86}$Y-EB-PSMA-617 or $^{86}$Y-EB-MCGwere added in 0.5 mL of medium containing 1% (w/v) human serum albumin (HSA). At each indicated time point, the cells were washed X2 with PBS and lysed with 0.1 M NaOH. Internalization was measured after removal of membrane-bound tracer by 1 min incubation with 0.5 mL of acid buffer (50 mM glycine, 100 mM NaCl, pH 2.8), wash X2 and lysis. Radioactivity of cell lysate was measured by a γ-counter (Perkin Elmer). The cell uptake and internalization values were normalized as a percent of added radioactivity. Each time point was measured in triplicate. For blocking studies, 10 μg of unlabeled ligand was added to the well, along with the radioactivity.

Example 11: Histopathologic Staining after Targeted Radiotherapy

Tumor tissues from each group described above were collected at different time points and frozen or kept at room temperature in Z-FIX (Anatec Ltd). 10 μm-thick sections were mounted on slides using a cryo-microtome. Ki-67, TUNEL and H&E staining were done according to our previous work (see Chen et al. "Novel 'Add-On" Molecule Based on Evans Blue Confers Superior Pharmacokinetics and Transforms Drugs to theranostic Agents" Journal of Nuclear Medicine 2017, 58 (4), 590-597). Number of Ki67-positive nuclei was analyzed by visual counting on 5-6 fields of view per slide, 5 slides for each mouse and 3 mice per group. Quantification was done using Image J software (NIH).

Example 12: Tumor Model

Animal protocols were approved by the NIH Clinical Center Animal Care and Use Committee (ACUC). Male athymic nude/nude mice (5-6 weeks) (Envigo) were inoculated on their right shoulder with $5\times10^6$ cells of either; PC3-PIP or PC3 cells in Matrigel (Sigma) 1:1.

Example 13: Biodistribution

After the last scan at 48 h time point, tumor, heart, lung, liver, spleen, stomach, intestine, pancreas, kidney, muscle, bone and blood were collected from euthanized mice, weighed and measured in a gamma counter. Results are normalized as percentages of the injected dose per gram of tissue (% ID/g).

Example 14: Tumor Uptake of $^{86}$Y-Eb-Psma-617

PET assays were performed at 14-17 days post tumor cells inoculation when the tumor volume reached about 200-350 mm³. Mice were injected intravenously with 0.5 nmol (high specific activity) of either $^{86}$Y-EB-PSMA-617 (n=5, PC3-PIP; n=5, PC3) or $^{86}$Y-EB-MCG (n=5, PC3-PIP; n=5, PC3), and scanned for 10-20 min at 1, 4, 24 and 48 h post injection (p.i.). PET studies were acquired on Nanoscan PET/CT (Mediso) and Inveon (Siemens) scanners. Images were reconstructed using a 3D ordered subset expectation maximum algorithm, and ROI were drawn using ASIPRO (Siemens) and multiple by a calibration factor to give % injected dose/mL (mean or max values) in the organ (tumor and kidneys). The assumption is that the density of 1 mL is equal to 1 g of tissue (excluded for lung).

Examples 15-17: Tumor Uptake of $^{86}$Y-Eb-Mcg, $^{86}$Y-Eb-Psma-617, and $^{86}$Y-Eb-Mcg Tumor uptakes of $^{86}$Y-EB-MCG, $^{86}$Y-EB-PSMA-617, and $^{86}$Y-EB-MCG were determined according to the procedure described for $^{86}$Y-EB-PSMA-617 in the preceding example.

Example 18: Radiotherapy with Eb-Psma-617 in Mice

Tumor treatment studies were performed in PC3-PIP xenograft to evaluate the therapeutic efficacy of intravenous injection/s of $^{90}$Y-EB-PSMA-617, $^{177}$Lu-EB-PSMA-617 vs. saline and $^{90}$Y-DOTA-PSMA-617 or $^{177}$Lu-DOTA-PSMA-617. The study was commenced 7 days post inoculation of Pc3-PIP xenograft, when all the mice had tumor volume of about 100-150 mm$^3$. The mice were divided into several groups as followed; (1) saline (n=4), (2) 7.4 MBq $^{90}$Y-EB-PSMA-617 (n=6), (3) 3.7 MBq $^{90}$Y-EB-PSMA-617 (n=6), (3) 18.5 MBq $^{177}$Lu-EB-PSMA-617 (n=6), (4) 7.4 MBq $^{177}$Lu-EB-PSMA-617 (n=6), (5) 7.4 MBq $^{90}$Y-DOTA-PSMA-617 (n=6) and 18.5 MBq $^{177}$Lu-DOTA-PSMA-617 (n=6). The mice received a single injection at day 0 (start of treatment). All the living mice were monitored for 50 days. Mice body weight and tumor volume were monitored every 3-7 days throughout the experiment. The formula used for calculation of tumor volume was V=width$^2$×length/2.

Endpoint criteria defined by the institute ACUC was weight loss of more than 15%, a tumor volume >1800 mm$^3$, active ulceration of the tumor or abnormal behavior indicating pain or unease. These definitions were used for Kaplan-Meier analysis as well.

Example 19: Radiotherapy with Eb-Mcg and Dota-Mcg in Mice

Experiments with EB-MCG/DOTA-MCG derivatives were done similarly to the procedure described in the preceding example.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A compound of Formula I or a pharmaceutically acceptable ester, amide, solvate, or salt thereof, or a salt of such an ester or amide or a solvate of such an ester amide or salt,

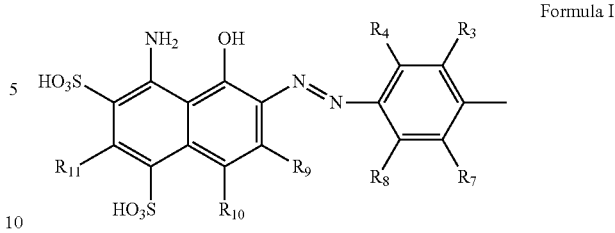

Formula I

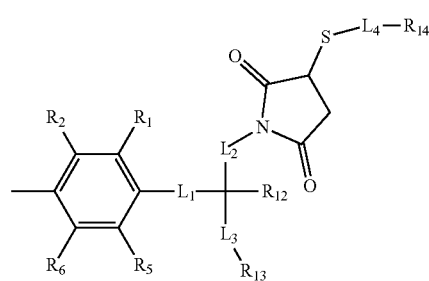

wherein:

$R_1$, $R_2$, $R_3$, $R_4$, $R_5$, $R_6$, $R_7$, $R_8$, $R_9$, $R_{10}$, and $R_{11}$ are independently selected from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy;

$R_{12}$ is hydrogen, $C_1$-$C_6$alkyl, or $C_1$-$C_6$haloalkyl;

$L_1$ is —(CH$_2$)$_m$— wherein m is an integer from 0 to 12, wherein each CH$_2$ is individually replaced with —O—, —NH(CO)—, or —(CO)—NH—, provided that no two adjacent CH$_2$ groups are replaced;

$L_2$ is —(CH$_2$)$_n$— wherein n is an integer from 0 to 12, wherein each CH$_2$ is individually replaced with —O—, —NH(CO)—, or —(CO)—NH—, provided that no two adjacent CH$_2$ groups are replaced;

$L_3$ is —(CH$_2$)$_p$— wherein p is an integer from 0 to 12, wherein each CH$_2$ is individually replaced with —O—, —NH(CO)—, or —(CO)—NH—, provided that no two adjacent CH$_2$ groups are replaced; and $L_4$ is a $C_1$-$C_{60}$ linking group, optionally including —O—, —S—, —S(O)—, —S(O)$_2$—, —N(R)—, —C(=O)—, —C(=O)O—, —OC(=O)—, —N(R)C(=O)—, —C(=O)N(R)—, —OC(=O)O—, —N(R)C(=O)O—, or —OC(=O)N(R)—, wherein each R is H or $C_1$-$C_6$ alkyl;

$R_{13}$ is a chelating group; and $R_{14}$ is a group capable of binding to prostate-specific membrane antigen (PSMA).

2. The compound of claim 1, wherein $L_4$ comprises —(CH$_2$)$_q$— wherein q is an integer from 0 to 12, wherein each CH$_2$ can be individually replaced with —O—, —NH(CO)—, or —(CO)—NH—, provided that no two adjacent CH$_2$ groups are replaced.

3. The compound of claim 1, wherein $L_1$ is —NH(CO)—, $R_1$ and $R_4$ are each methyl, and $R_2$, $R_3$, $R_5$, $R_6$, $R_7$, $R_8$, $R_9$, $R_{10}$, $R_{11}$, and $R_{12}$ are each hydrogen.

4. The compound of claim 1, wherein $R_{14}$ comprises

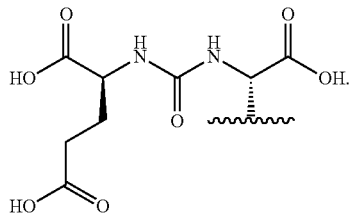

5. The compound of claim 1, wherein $R_{14}$ comprises

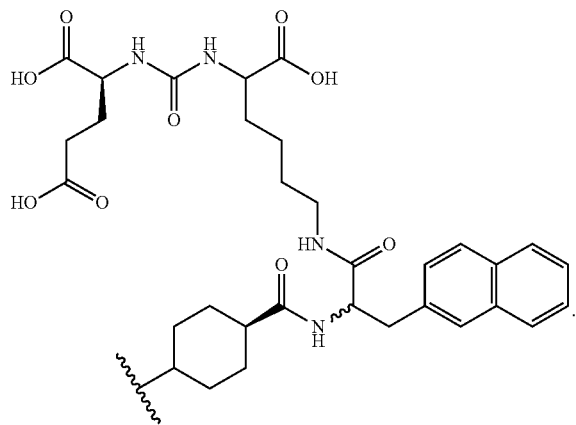

6. The compound of claim 1, wherein $R_{14}$ is

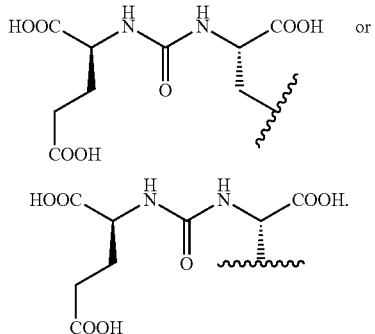 or

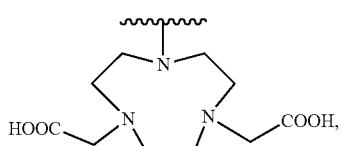

7. The compound of claim 1, wherein $R_{14}$ further comprises a radionuclide.

8. The compound of claim 7, wherein the radionuclide is $^{18}F$, $^{76}Br$, $^{124}I$, $^{125}I$, or $^{131}I$.

9. The compound of claim 1, wherein $R_{13}$ is selected from

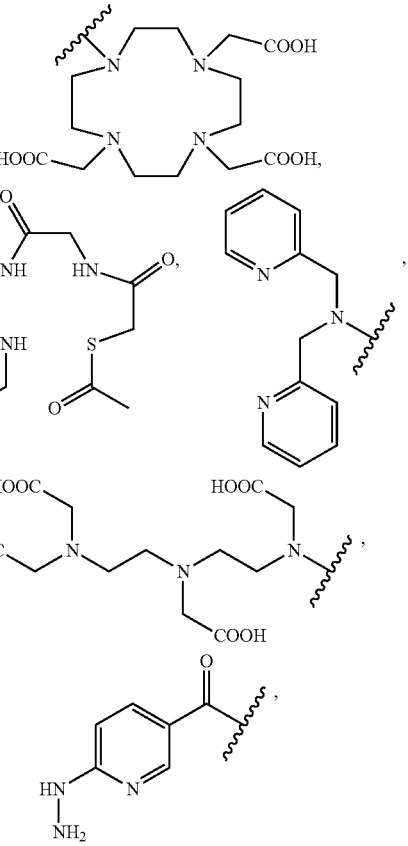

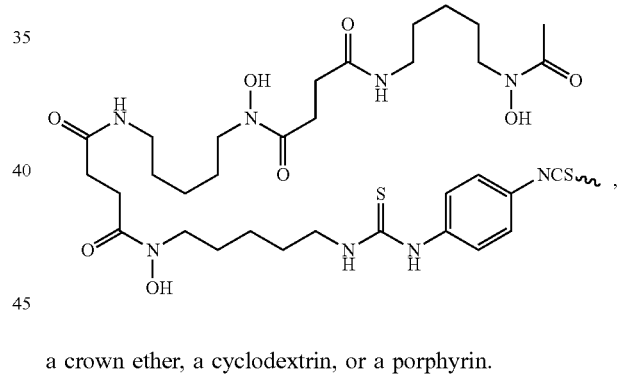

a crown ether, a cyclodextrin, or a porphyrin.

10. The compound of claim 1, wherein $R_{13}$ is

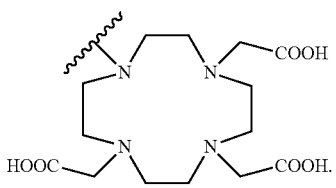 [SMILES: *N1CCN(CC(=O)O)CCN(CC(=O)O)CCN(CC(=O)O)CC1]

11. The compound of claim 1, wherein $R_{13}$ further comprises a radionuclide.

12. The compound of claim 11, wherein the radionuclide is $^{64}Cu$, $^{67}Cu$, $^{90}Y$, $^{86}Y$, $^{111}In$, $^{186}Re$, $^{188}Re$, $^{89}Zr$, $^{99}Tc$, $^{153}Sm$, $^{213}Bi$, $^{225}Ac$, $^{177}Lu$, or $^{223}Ra$.

13. The compound of claim 12, wherein the radionuclide is $^{86}Y$, $^{90}Y$, or $^{177}Lu$.

14. The compound of claim 1, wherein the compound of Formula II is a compound of Formula II:
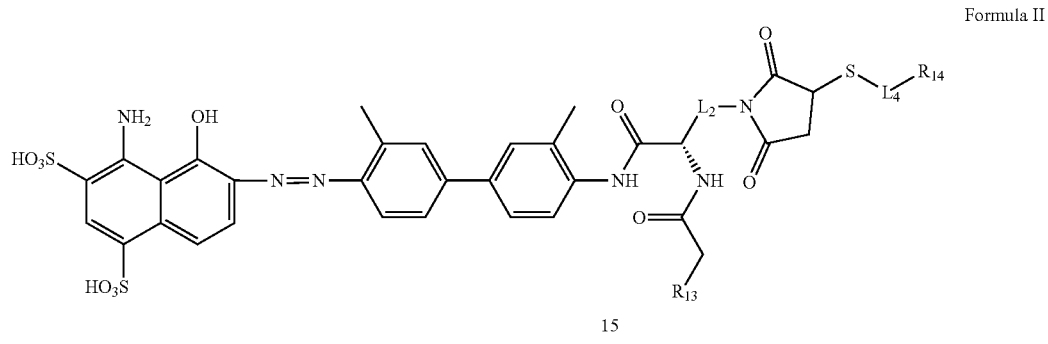
Formula II
wherein $L_2$, $L_4$, $R_{13}$, and $R_{14}$ are the same as in claim 1.
15. The compound of claim 1, wherein the compound is
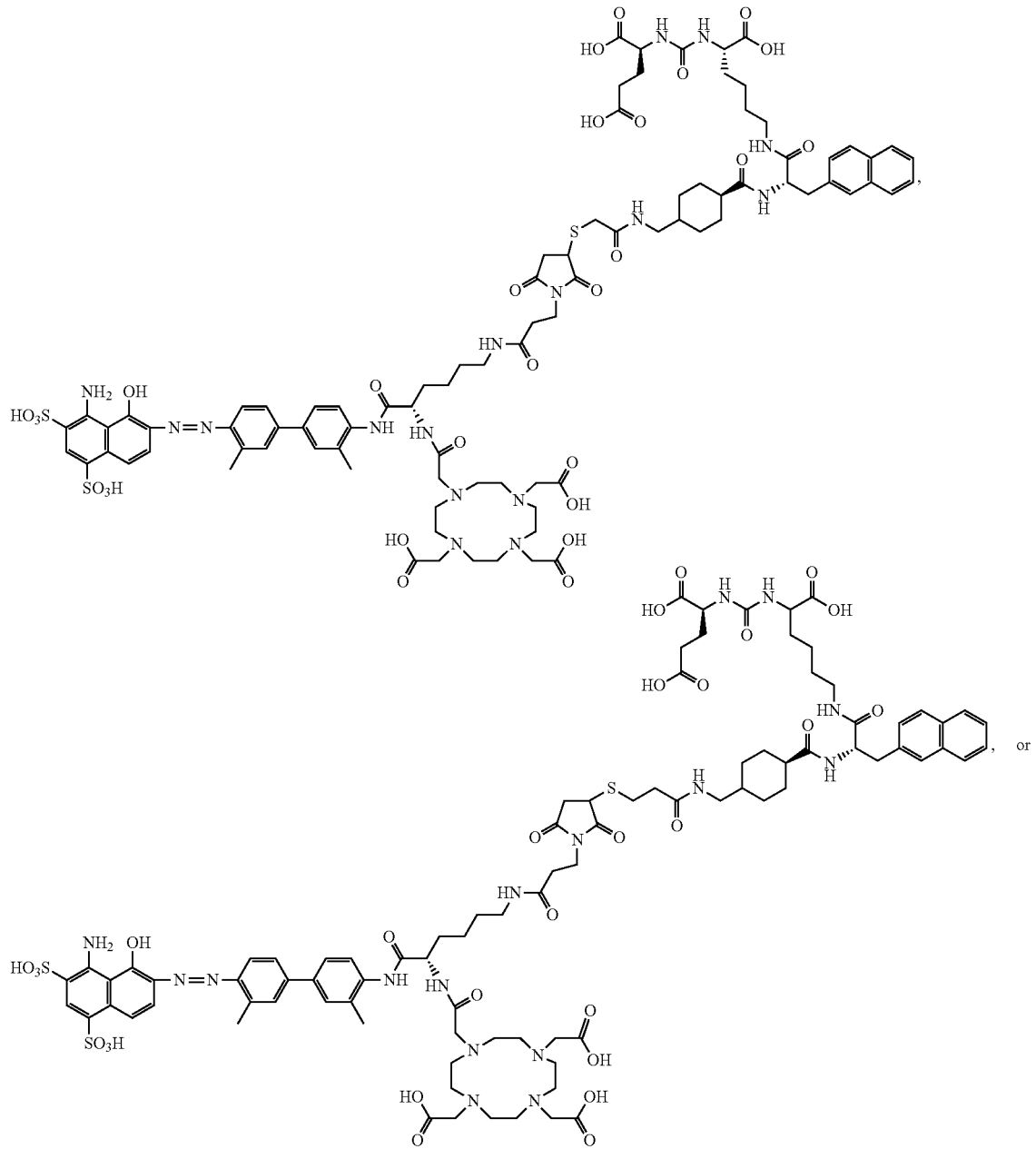

-continued

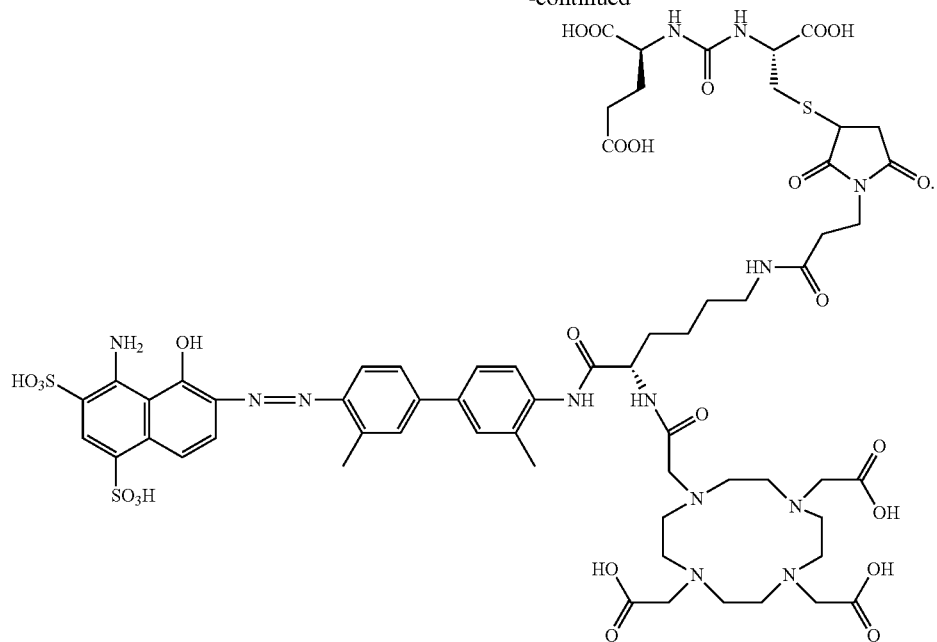

16. A pharmaceutical composition comprising the compound of claim 1 together with a pharmaceutically acceptable carrier.

17. The composition of claim 16, wherein the pharmaceutically acceptable carrier is selected from the group consisting of binders, buffering agents, coloring agents, diluents, disintegrants, emulsifiers, flavorants, glidants, lubricants, preservatives, stabilizers, surfactants, tableting agents, and wetting agents, and combinations thereof.

18. A method of treating prostate cancer in a mammal, comprising administering to said mammal a therapeutically effective amount of a compound of claim 1, optionally in combination with one or more additional active ingredients.

19. The method of claim 18, wherein the one or more additional active ingredients are selected from the one or more additional compounds may include additional therapeutic compounds, including anti-cancer therapeutic compounds such as doxorubicin, paclitaxel, docetaxel, cisplatin, camptothecin, temozolomide, avastin, Herceptin, Erbitux, and combinations thereof.

20. The compound of claim 1, wherein the compound is

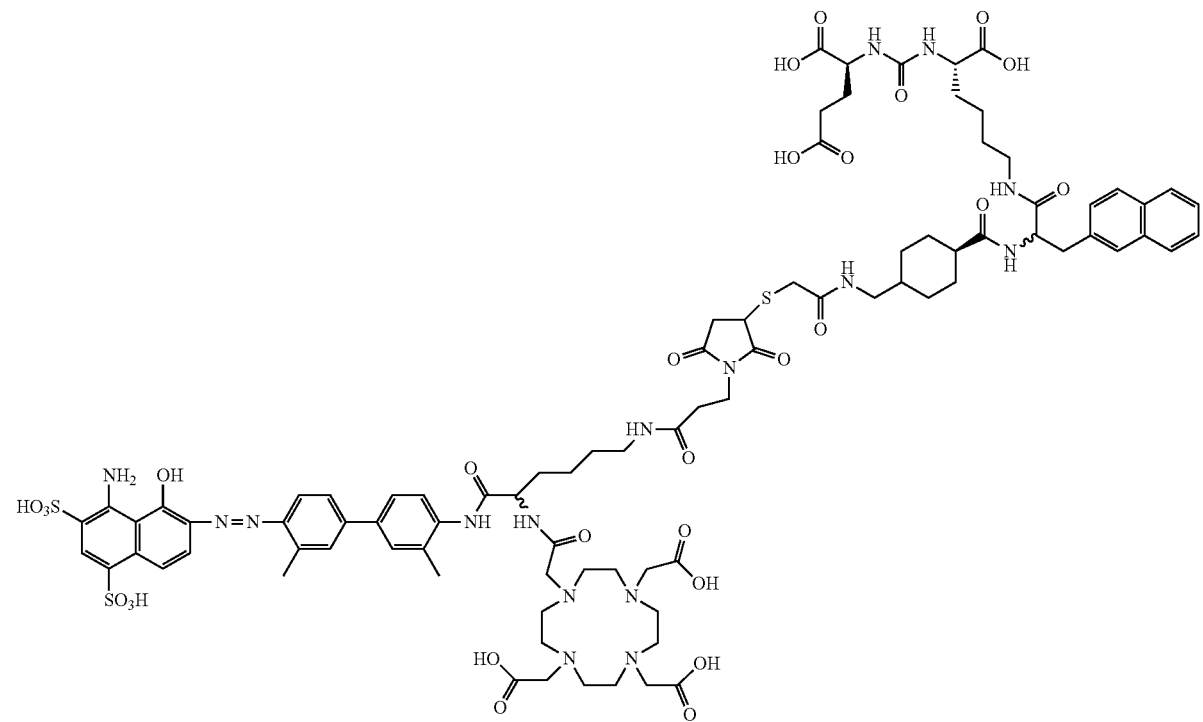

* * * * *